United States Patent
Park et al.

(10) Patent No.: US 12,326,449 B2
(45) Date of Patent: Jun. 10, 2025

(54) FIBRINOGEN BIOLOGICAL MATERIAL DETECTION SENSOR INCLUDING AN ERYTHROCYTE MEMBRANE COVERED METAL NANOPARTICLE AND FABRICATING METHOD THEREOF

(71) Applicant: KOREA UNIVERSITY RESEARCH AND BUSINESS FOUNDATION, SEJONG CAMPUS, Sejong-si (KR)

(72) Inventors: Jin Sung Park, Guri-si (KR); Seong Jae Jo, Seoul (KR); Joo Hyung Park, Jinju-si (KR); Won Seok Lee, Seoul (KR); Heon Jeong Lee, Seoul (KR); Dae Sung Yoon, Seoul (KR); Gyu Do Lee, Namyangju-si (KR); In Su Kim, Seoul (KR)

(73) Assignee: KOREA UNIVERSITY RESEARCH AND BUSINESS FOUNDATION, SEJONG CAMPUS, Sejong-si (KR)

( * ) Notice: Subject to any disclaimer, the term of this patent is extended or adjusted under 35 U.S.C. 154(b) by 1066 days.

(21) Appl. No.: 17/233,859

(22) Filed: Apr. 19, 2021

(65) Prior Publication Data
US 2021/0239693 A1    Aug. 5, 2021

Related U.S. Application Data

(63) Continuation of application No. PCT/KR2019/013737, filed on Oct. 18, 2019.

(30) Foreign Application Priority Data

Oct. 18, 2018 (KR) .................. 10-2018-0124126
Jan. 2, 2019 (KR) .................. 10-2019-0000054
Jul. 22, 2019 (KR) .................. 10-2019-0088035

(51) Int. Cl.
*G01N 33/556* (2006.01)
*G01N 21/55* (2014.01)
(Continued)

(52) U.S. Cl.
CPC ......... *G01N 33/556* (2013.01); *G01N 27/127* (2013.01); *G01N 33/553* (2013.01); *G01N 33/743* (2013.01); *G01N 33/86* (2013.01)

(58) Field of Classification Search
CPC .......... G01N 33/54346; G01N 33/743; G01N 21/552; G01N 33/553; G01N 33/86;
(Continued)

(56) References Cited

U.S. PATENT DOCUMENTS 4,869,826 A * 9/1989 Wang .................. B01J 20/3204
                                                               210/198.2
5,288,610 A * 2/1994 Shibata ............ G01N 33/56966
                                                                 436/829
(Continued)

FOREIGN PATENT DOCUMENTS

JP       2005-521733 A     7/2005
KR   10-2012-0033875 A     4/2012
(Continued)

OTHER PUBLICATIONS

Steck, T. L. et al, Methods in Enzymology 1974, 31, 172-180. (Year: 1974).*
(Continued)

*Primary Examiner* — Arlen Soderquist
(74) *Attorney, Agent, or Firm* — Sughrue Mion, PLLC

(57) ABSTRACT

Provided is a biomaterial detection sensor. The biomaterial detection sensor comprises a substrate and a detection probe including a metal nanoparticle deposited on the substrate,
(Continued)

and an erythrocyte membrane conformally covering the metal nanoparticle, wherein the detection probe may selectively react with fibrinogen.

7 Claims, 62 Drawing Sheets

(51) Int. Cl.
  *G01N 27/12* (2006.01)
  *G01N 33/553* (2006.01)
  *G01N 33/74* (2006.01)
  *G01N 33/86* (2006.01)

(58) Field of Classification Search
  CPC ............... G01N 33/556; G01N 27/127; G01N 2333/75; G01N 2333/575
  USPC ........................................... 422/82.02, 82.05
  See application file for complete search history.

(56) References Cited

U.S. PATENT DOCUMENTS

| | | | |
|---|---|---|---|
| 5,527,712 A * | 6/1996 | Sheehy | G01N 33/533 436/805 |
| 5,919,576 A * | 7/1999 | Hui | A61L 27/3604 428/545 |
| 2003/0157732 A1* | 8/2003 | Baker | G01N 21/658 436/171 |
| 2003/0170687 A1* | 9/2003 | Chilkoti | G01N 33/553 435/5 |
| 2004/0048354 A1* | 3/2004 | Darashkevitch | G01N 33/54326 435/252.3 |
| 2007/0275369 A1* | 11/2007 | Groves | G01N 33/542 435/5 |
| 2009/0069193 A1* | 3/2009 | Flemming | G01N 33/553 506/13 |
| 2009/0082216 A1* | 3/2009 | Cohn | B82Y 40/00 73/851 |
| 2009/0117666 A1* | 5/2009 | Mpock | G01N 33/86 436/501 |
| 2010/0009862 A1* | 1/2010 | Nakahara | G01N 33/582 506/13 |
| 2010/0167946 A1* | 7/2010 | Shaw | G01N 33/54313 506/13 |
| 2010/0256005 A1* | 10/2010 | Petrik | G01N 33/54393 506/18 |
| 2011/0097819 A1* | 4/2011 | Groves | G01N 33/567 436/503 |
| 2013/0040850 A1* | 2/2013 | Sigal | G01N 33/56983 435/7.25 |
| 2013/0337066 A1* | 12/2013 | Zhang | A61P 35/00 424/234.1 |
| 2015/0177180 A1 | 6/2015 | Davis | |
| 2016/0116490 A1* | 4/2016 | Knutson | G01N 33/6854 435/7.1 |
| 2016/0136106 A1* | 5/2016 | Zhang | A61K 31/4709 424/490 |
| 2016/0341747 A1* | 11/2016 | Ewert | G01N 33/86 |
| 2017/0095510 A1* | 4/2017 | Lee | A61K 35/18 |
| 2019/0195867 A1* | 6/2019 | Rheinstadter | G01N 33/49 |
| 2021/0011033 A1* | 1/2021 | Xu | G01N 33/725 |
| 2021/0116448 A1* | 4/2021 | Yoon | G01N 33/68 |

FOREIGN PATENT DOCUMENTS

| | | |
|---|---|---|
| KR | 10-2014-0143140 A | 12/2014 |
| KR | 10-1570149 B1 | 11/2015 |
| KR | 10-2015-0139639 A | 12/2015 |
| KR | 10-2018-0090063 A | 8/2018 |

OTHER PUBLICATIONS

Rao, N. M. et al, Biophysical Journal 1997, 73, 3066-3077. (Year: 1997).*
Hubbard, J. B. et al, Biophysical Chemistry 1998, 75, 163-176. (Year: 1998).*
Jiang, Z.-L. et al, Analytica Chimica Acta 2006, 571, 200-205. (Year: 2006).*
Tang, D. et al, Biosensors and Bioelectronics 2007, 22, 1116-1120. (Year: 2007).*
De Oliveira, S. et al, Biochimica et Biophysica Acta 2012, 1818, 481-490. (Year: 2012).*
Poon, K. W. C. et al, Analyst 2012, 137, 1807-1814. (Year: 2012).*
Kim, H.-M. et al, European Journal of Inorganic Chemistry 2012, 5343-5349. (Year: 2012).*
Gao, W. et al, Advanced Materials 2013, 25, 3549-3553. (Year: 2013).*
Chen, Y.-Y. et al, Analyst 2014, 139, 5977-5982 with 20 pages of supplementary information. (Year: 2014).*
Dietz, P. et al, ChemElectroChem 2014, 1, 200-206 200. (Year: 2014).*
Alatraktchi, F. A. et al, Sensors 2014, 14, 22128-22139. (Year: 2014).*
Hu, C.-M. J. et al, Nature 2015, 526, 118-121 with 13 pages of online content. (Year: 2015).*
Saleem, W. et al, Biosensors and Bioelectronics 2016, 86, 522-529 with 11 pages of supplementary information. (Year: 2016).*
Kroll, A. V. et al, Bioconjugate Chemistry 2017, 28, 23-32. (Year: 2017).*
Regmi, A. et al, Applied Physics Letters 2017, 111, paper 082106, 5 pages. (Year: 2017).*
Chen, H.-W. et al, ACS Applied Materials & Interfaces 2017, 9, 39953-39961. (Year: 2017).*
Kim, I. et al, Biosensors and Bioelectronics 2018, 102, 617-623 with 16 pages of supplementary material. (Year: 2018).*
Fang, R. H. et al, Advanced Materials 2018, 30, 1706759. (Year: 2018).*
Shao, J. et al, ACS Nano 2018, 12, 4877-4885. (Year: 2018).*
Singh, P. et al, International Journal of Molecular Sciences 2018, 19, paper 1979, 16 pages. (Year: 2018).*
Subramanian Balamurugan et al., "Nanostructure shape effects on response of plasmonic aptamer sensors", J. Mol. Recognit., 2013, pp. 402-407, vol. 26.
Azrul Syafiq Zainol Abidin et al., "Current and Potential Developments of Cortisol Aptasensing towards Point-of-Care Diagnostics (POTC)", Sensors, 2017, pp. 1-13, vol. 17, No. 1180.
Krishnendu Saha et al., "Gold Nanoparticles in Chemical and Biological Sensing", Chem. Rev., 2012, pp. 2739-2779, vol. 112.
Joohyung Park et al., "Ultrasensitive detection of fibrinogen using erythrocyte membrane-draped electrochemical impedance biosensor", Sensors and Actuators B: Chemical, 2019, pp. 296-303, vol. 293.
Clotilde Ribauta et al., "Electrochemical impedance spectroscopy to study physiological changes affecting the red blood cell after invasion by malaria parasites", Biosensors and Bioelectronics, 2009, pp. 2721-2725, vol. 24.
International Search Report of PCT/KR2019/013737 dated Jan. 22, 2020 [PCT/ISA/210].

* cited by examiner

[Fig. 1]
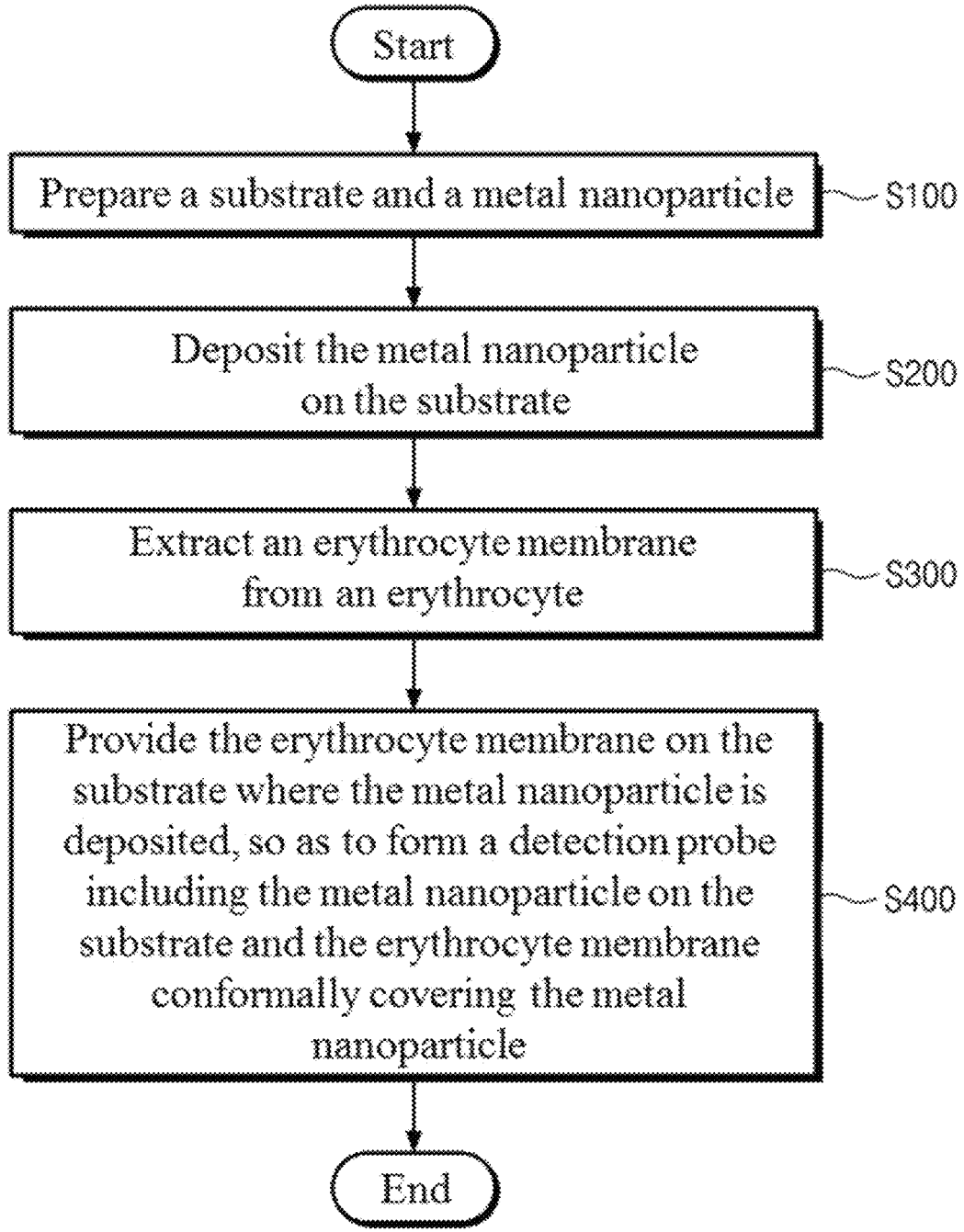

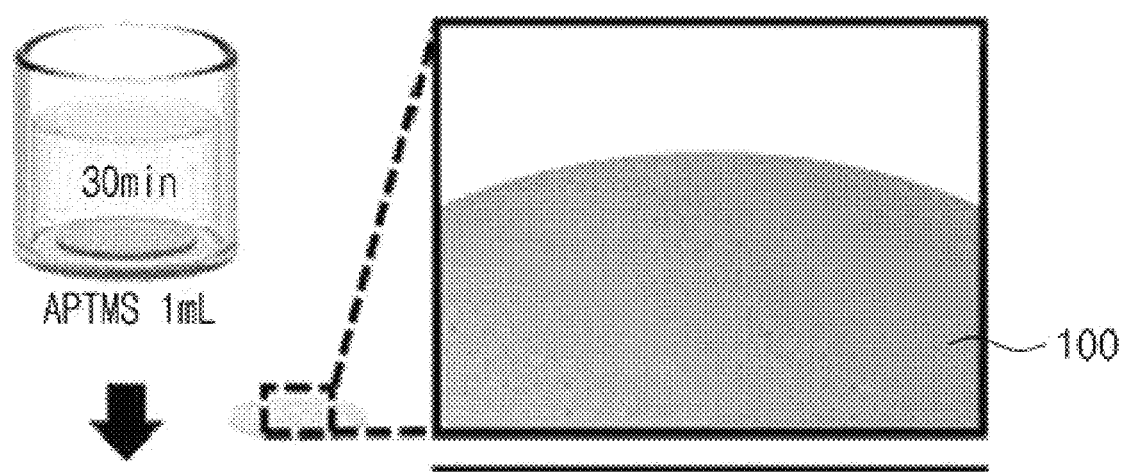

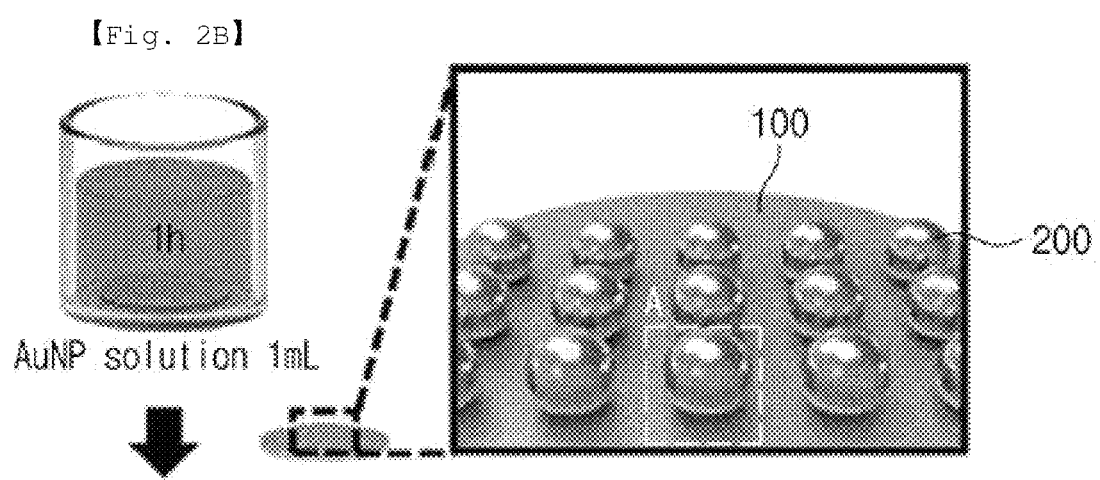

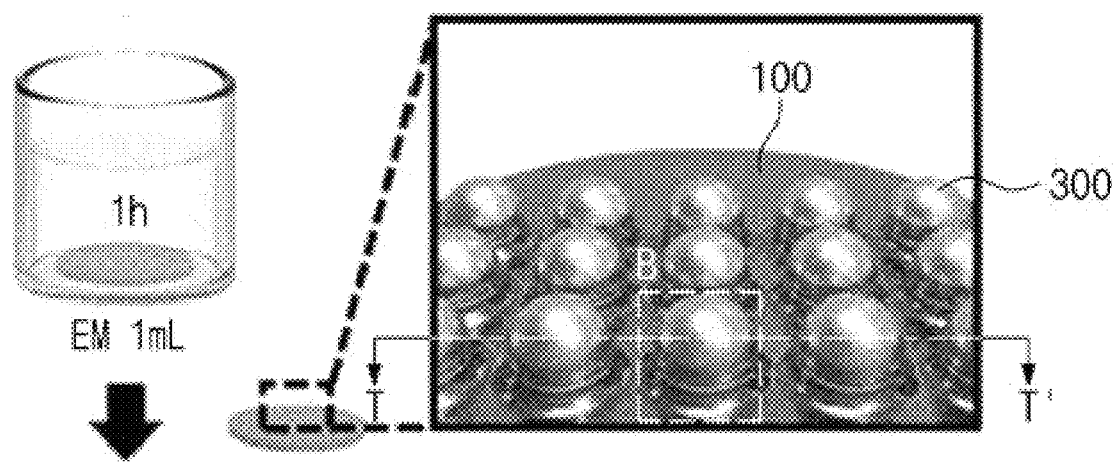
[Fig. 2C]

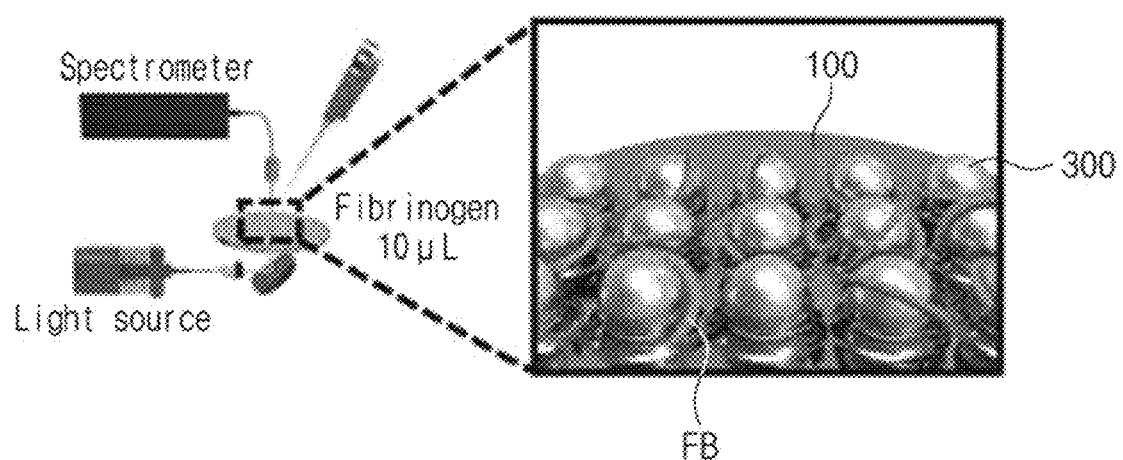
[Fig. 2D]

[Fig. 3A]
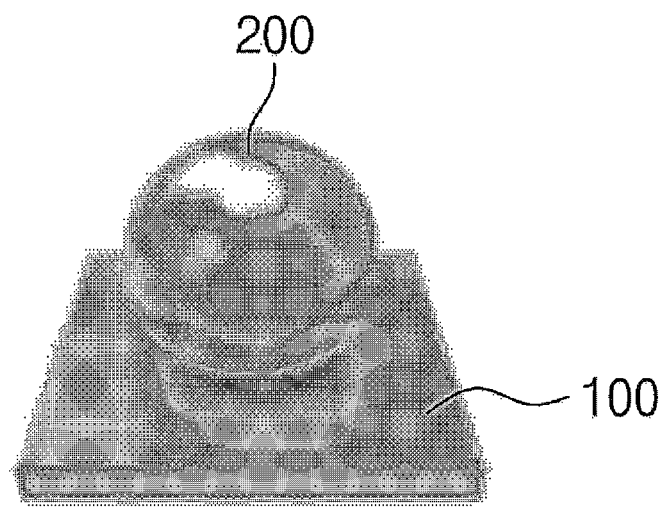

[Fig 3B]
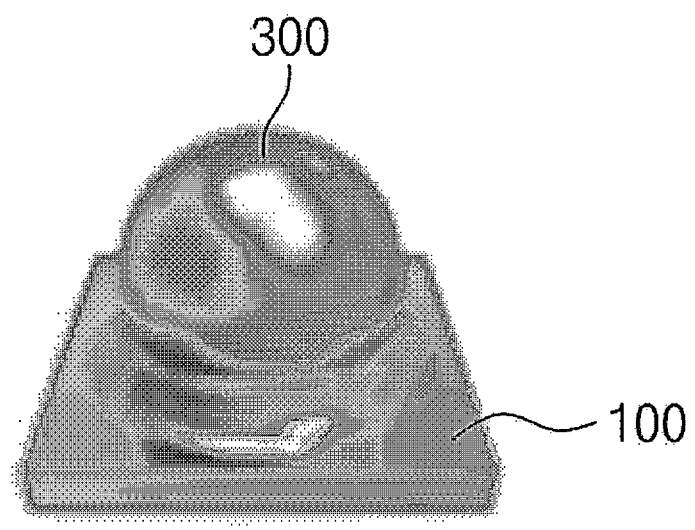

[Fig. 4]
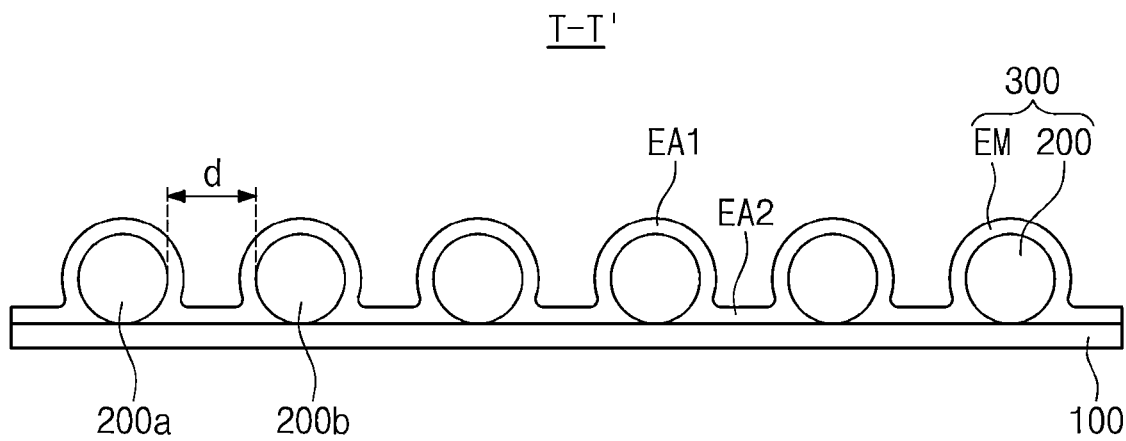

[Fig. 5]
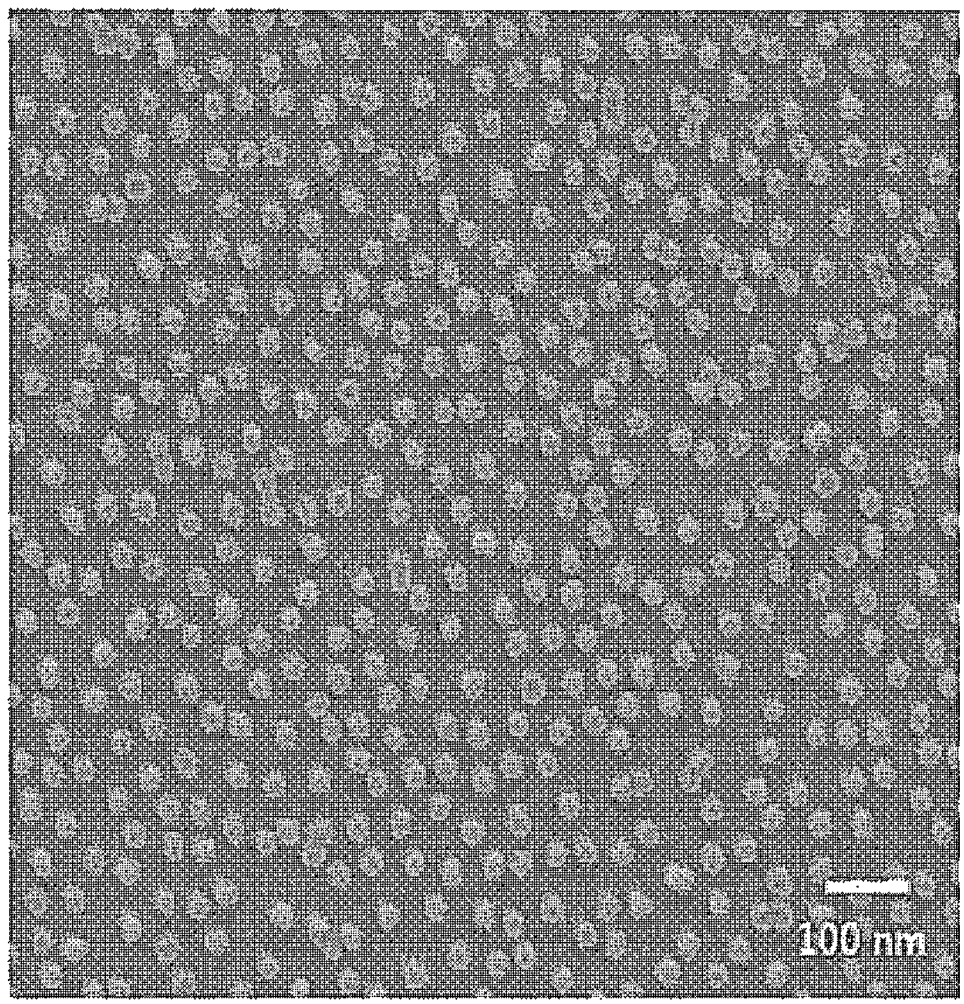

[Fig. 6A]
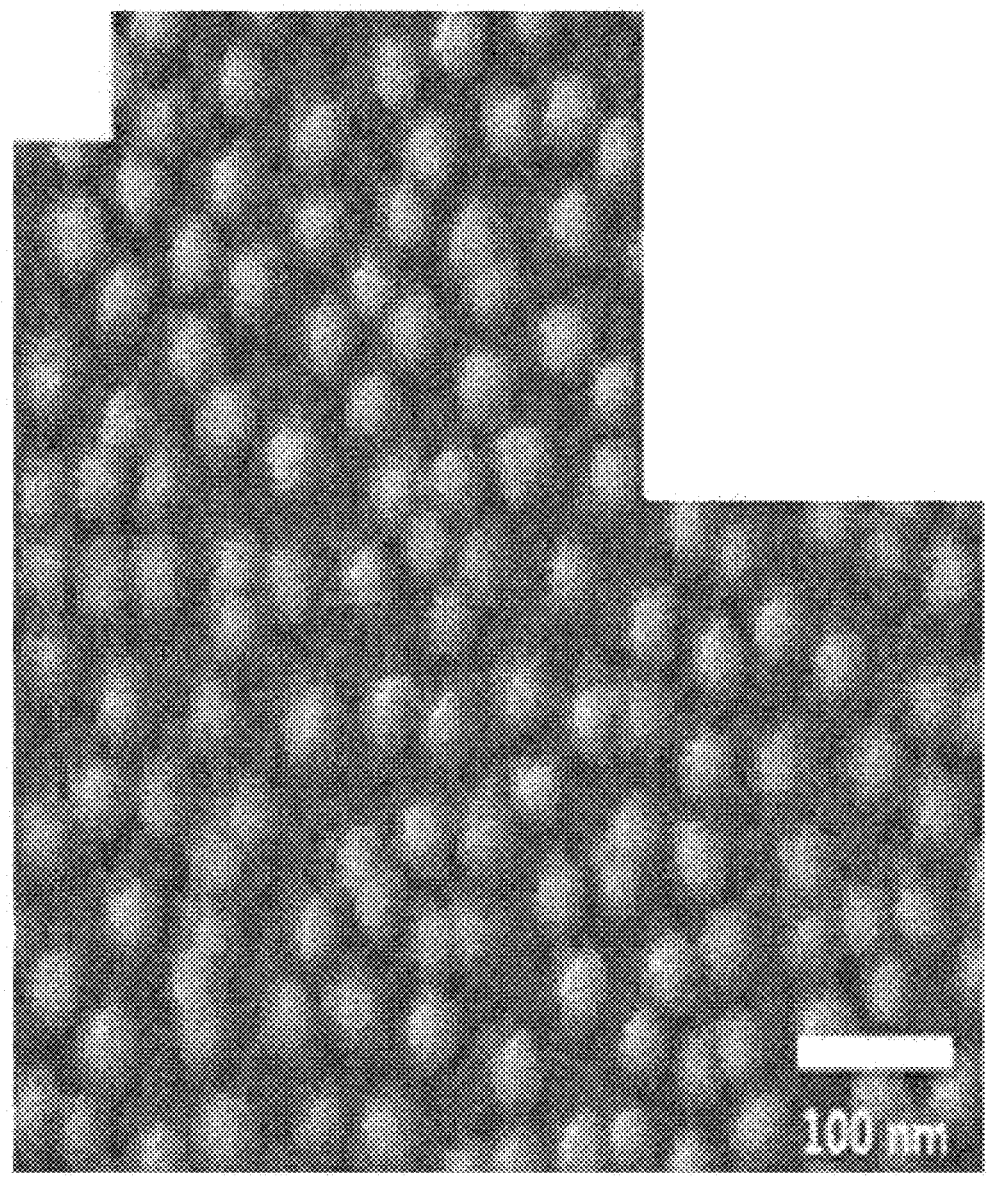

[Fig. 6B]
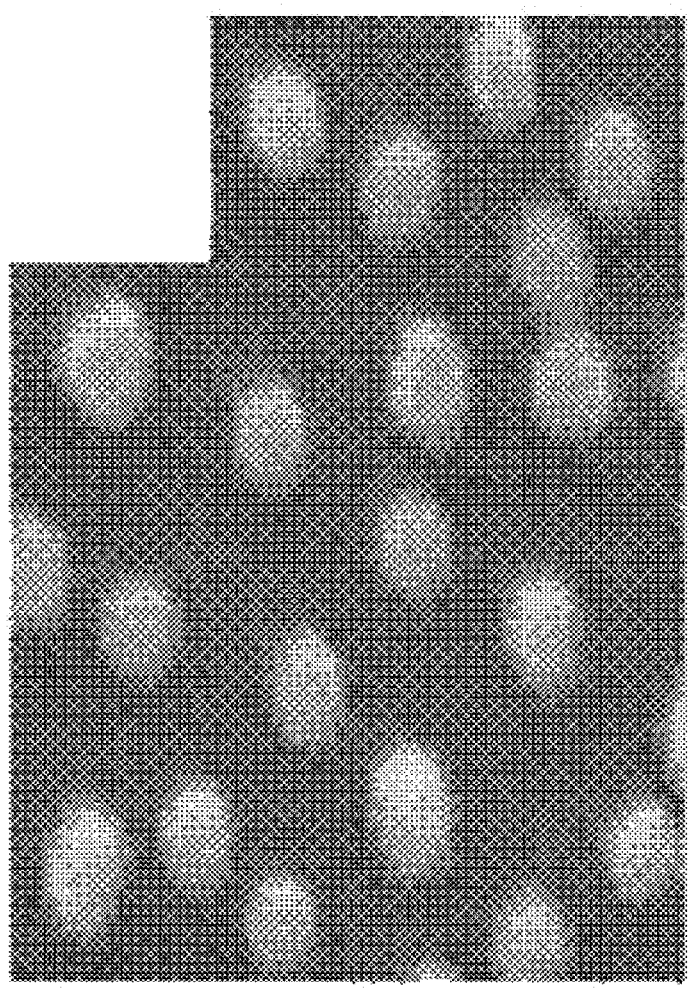

[Fig. 7A]
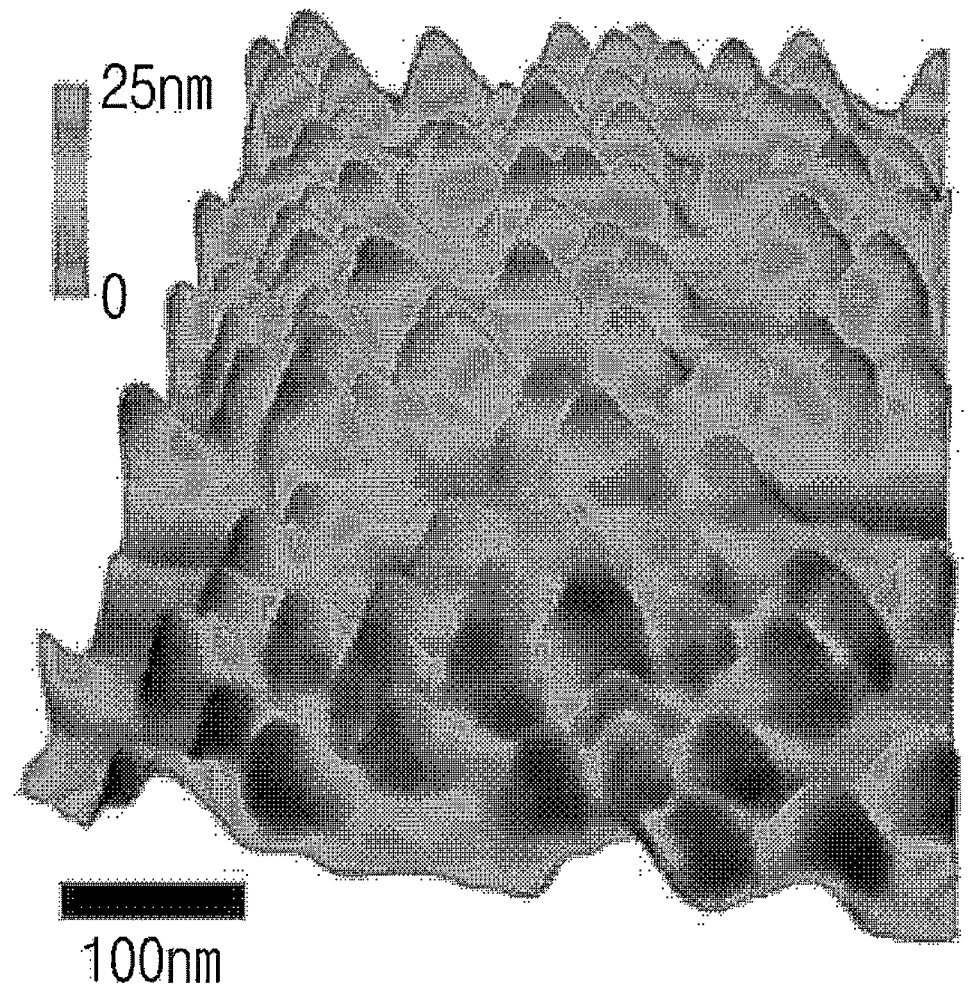

【Fig. 7B】
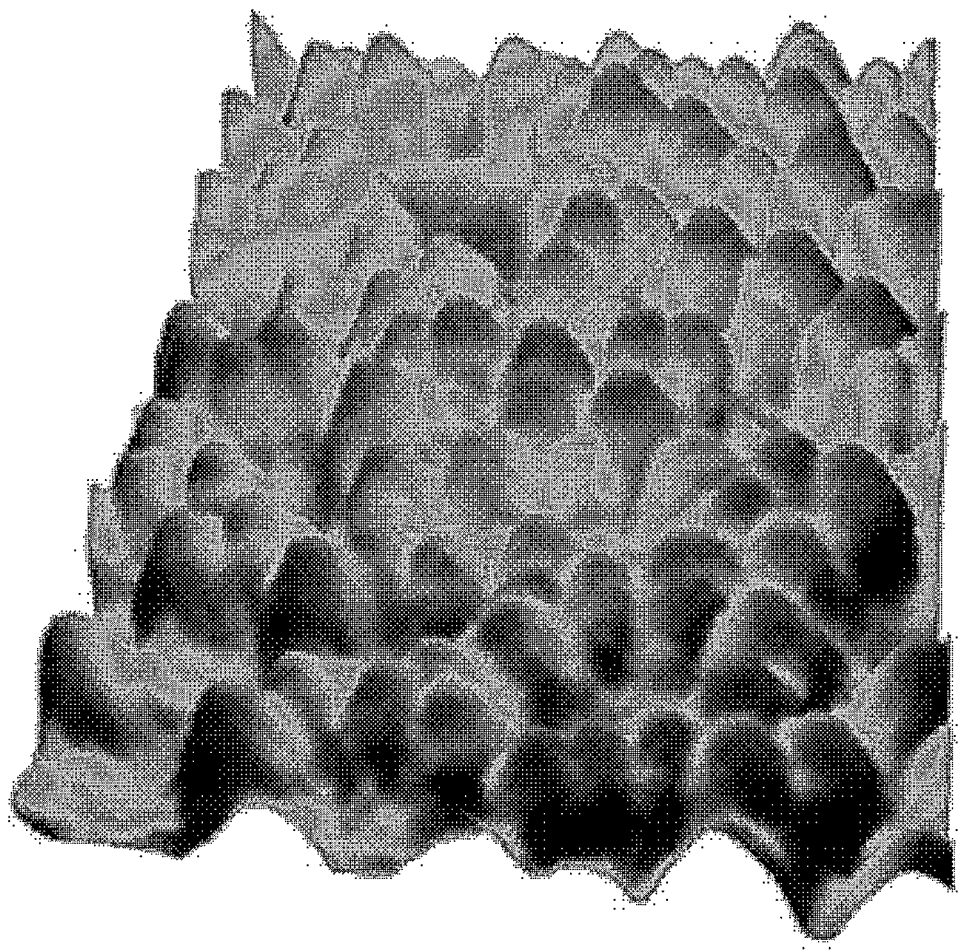

[Fig. 8A]
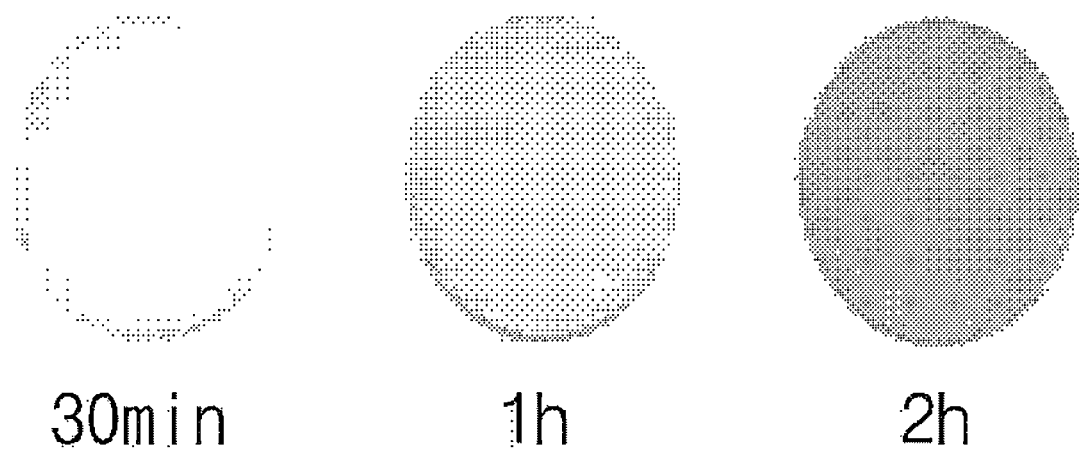

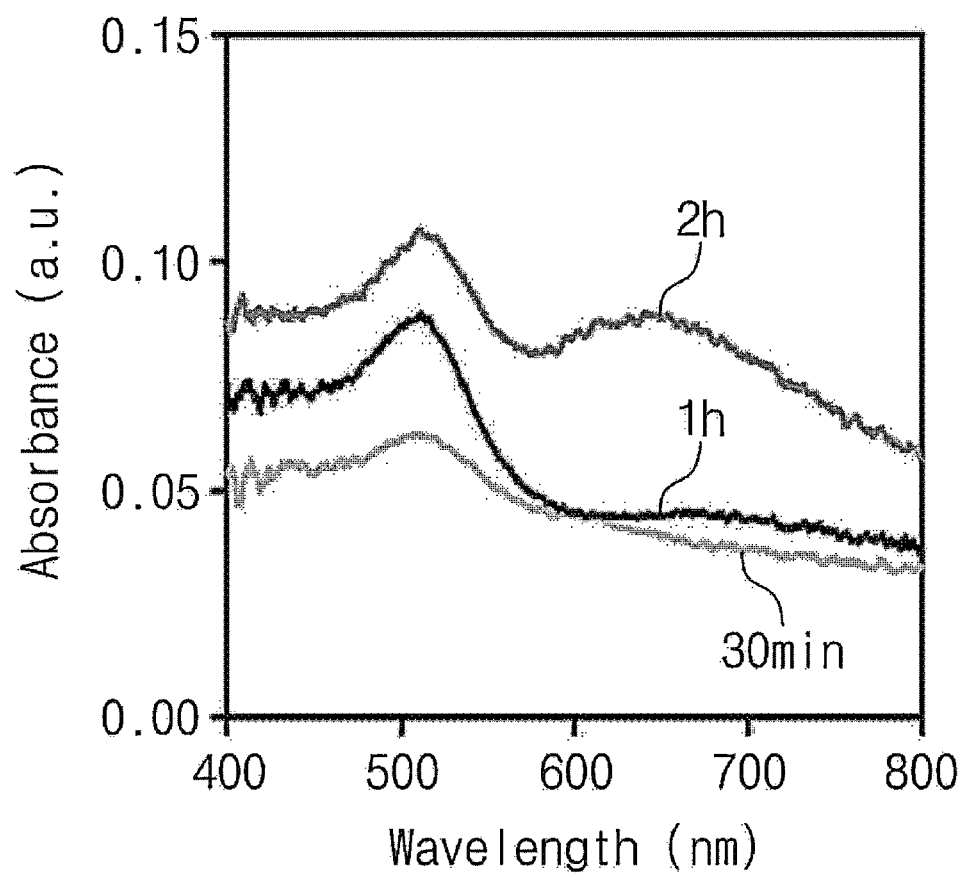
[Fig. 8B]

[Fig. 9A]

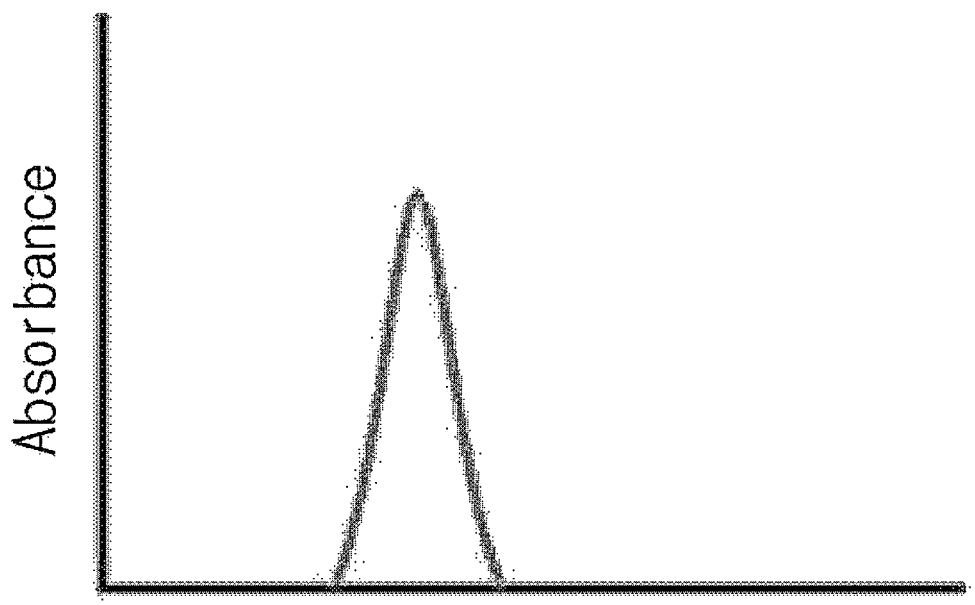
[Fig. 9B]

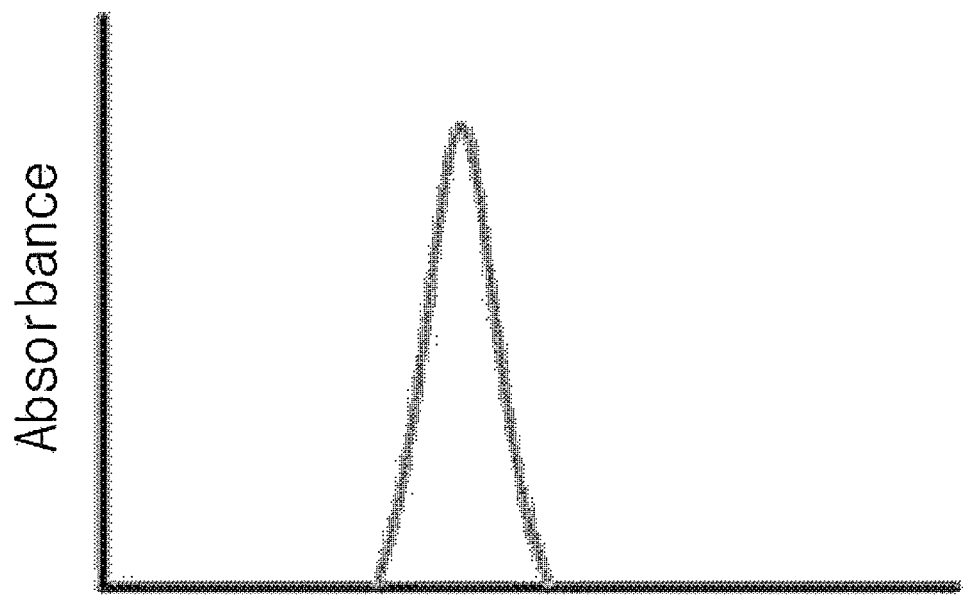
[Fig. 9C]

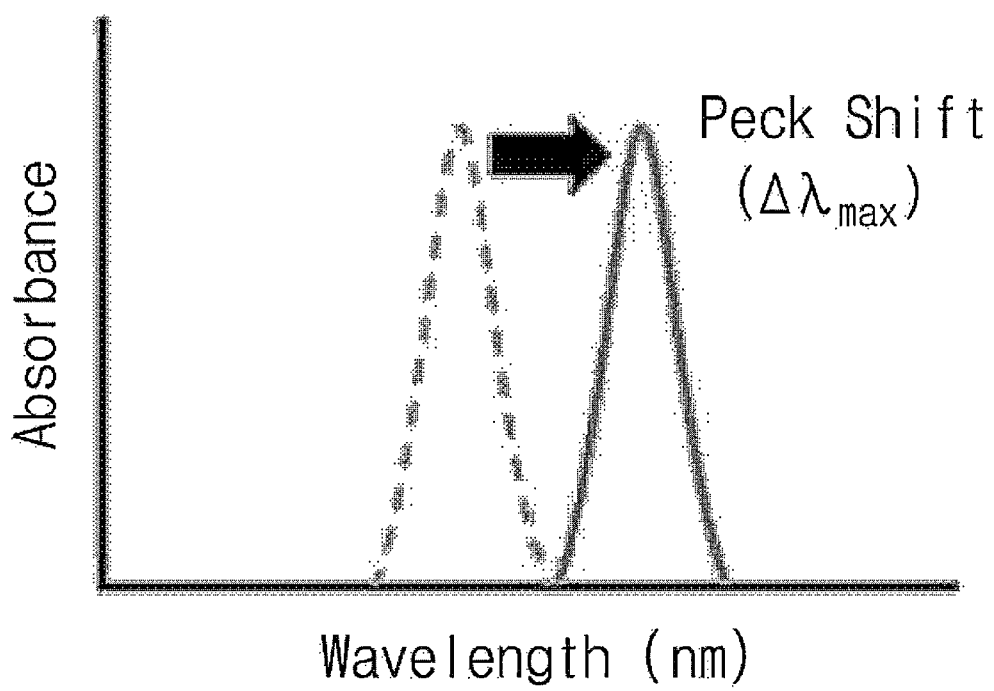
[Fig. 9D]

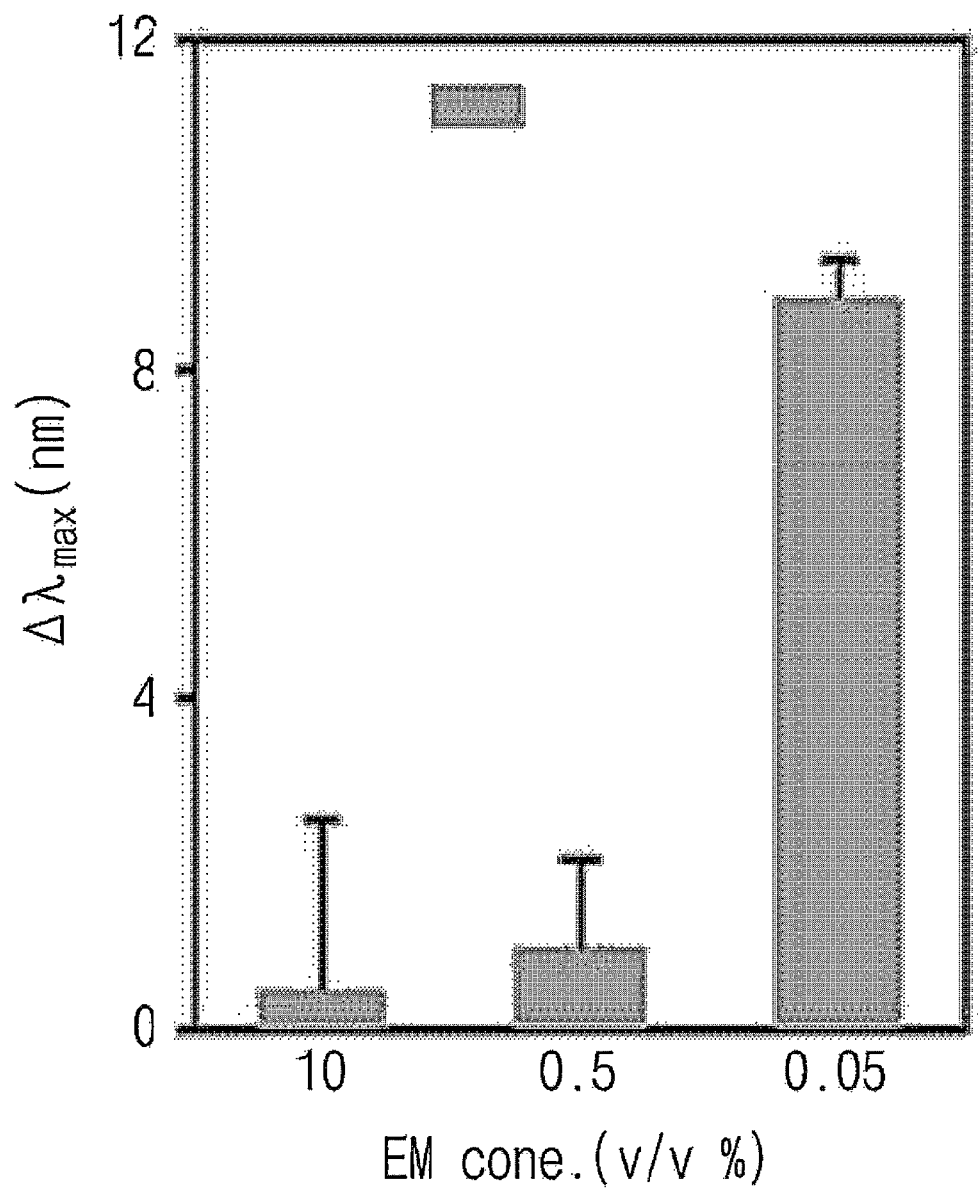
[Fig. 10A]

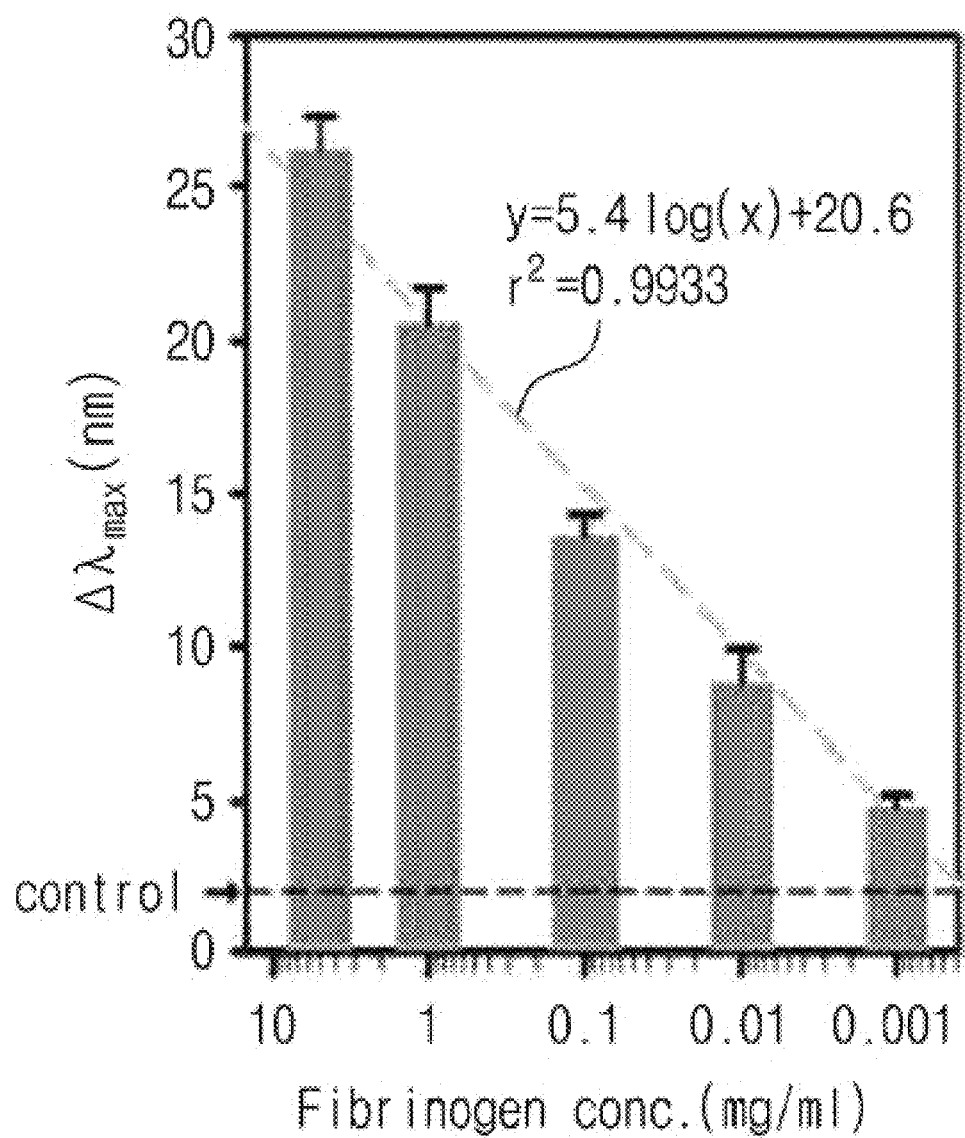
[Fig. 10B]

[Fig. 11A]
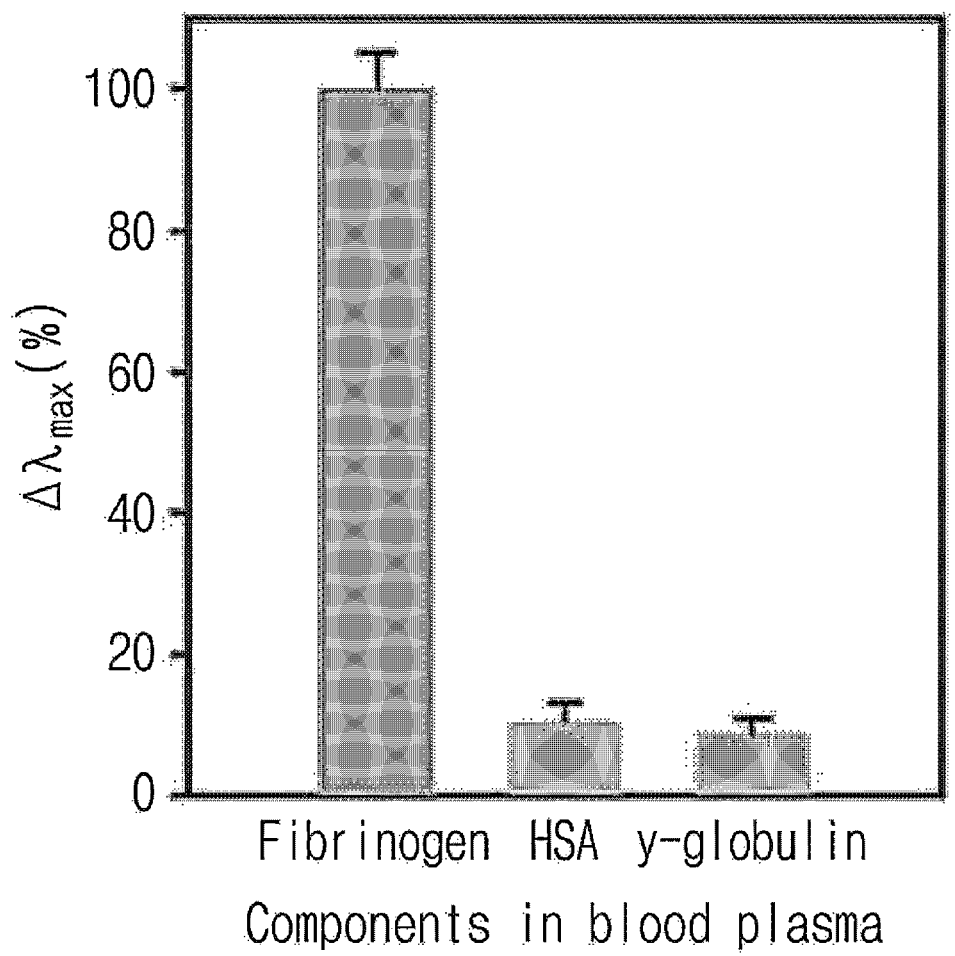

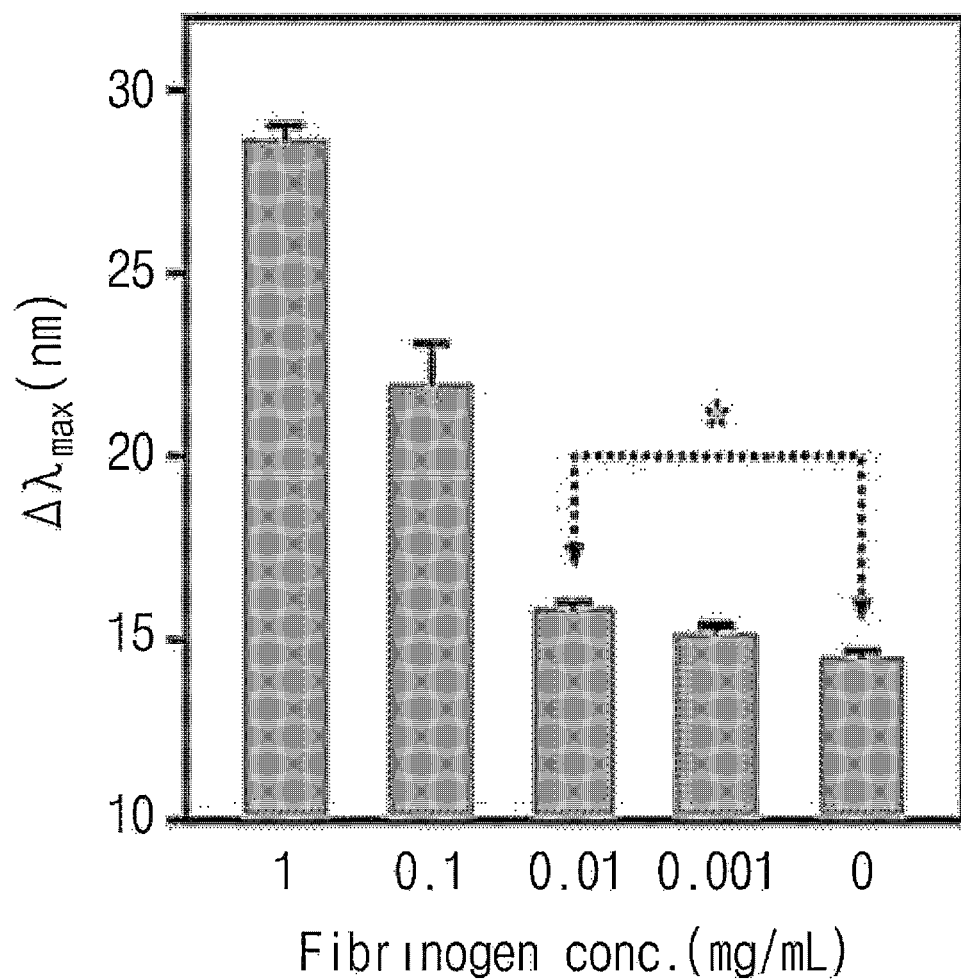
[Fig. 11B]

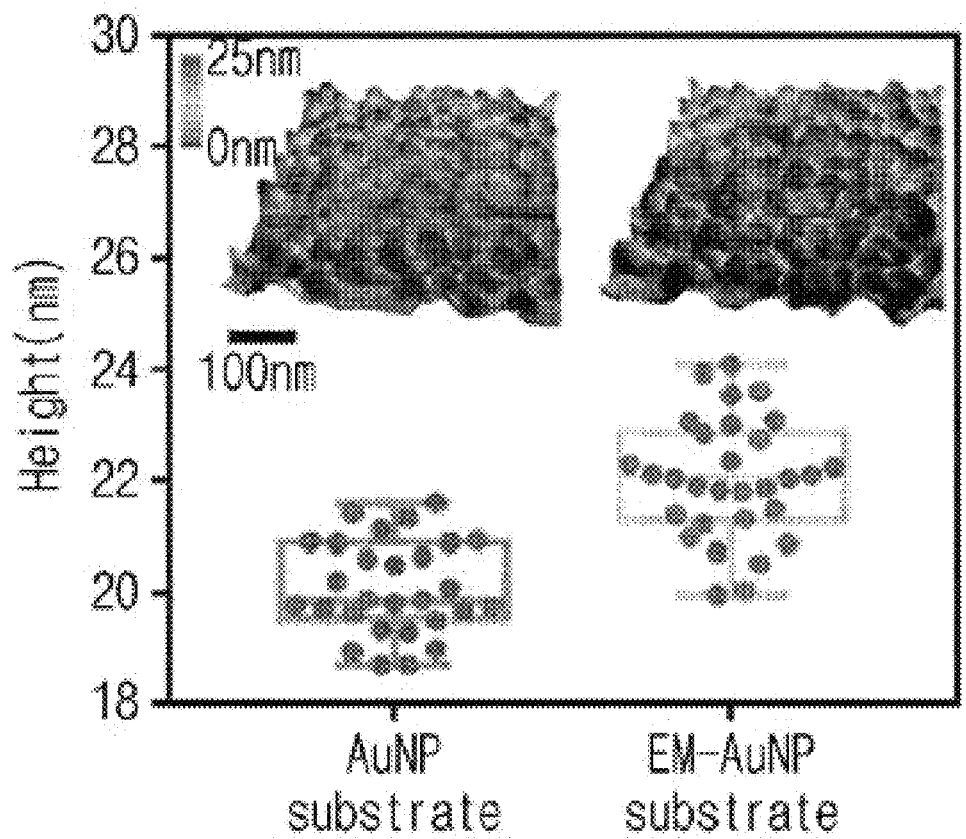
[Fig. 12A]

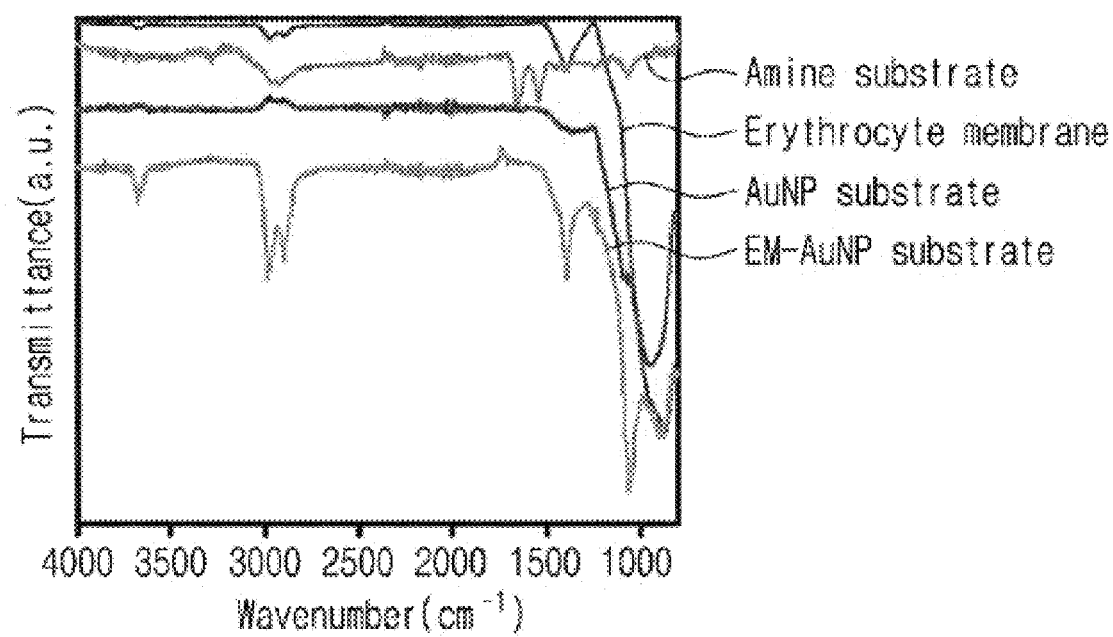
[Fig. 12B]

[Fig. 12C]
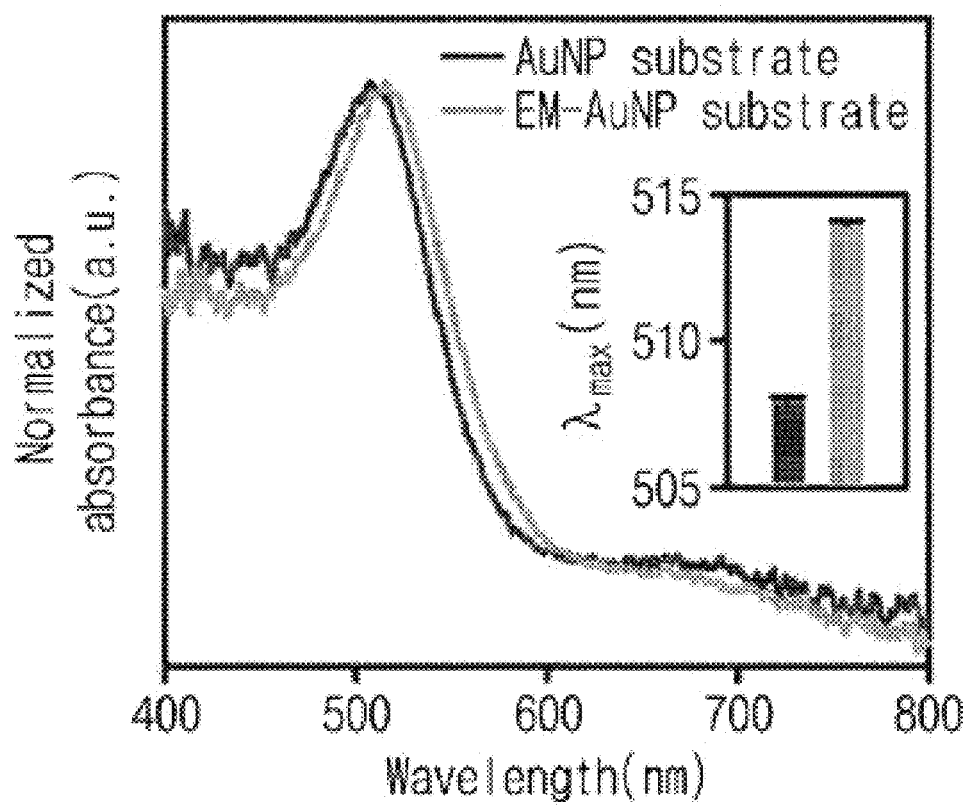

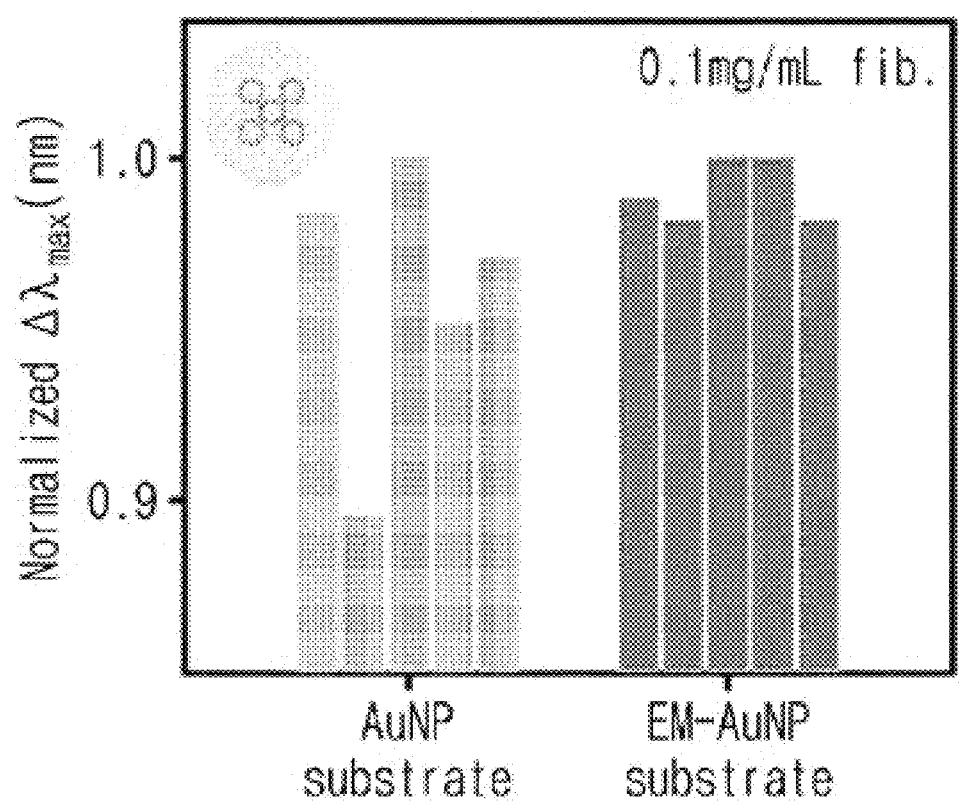
[Fig. 12D]

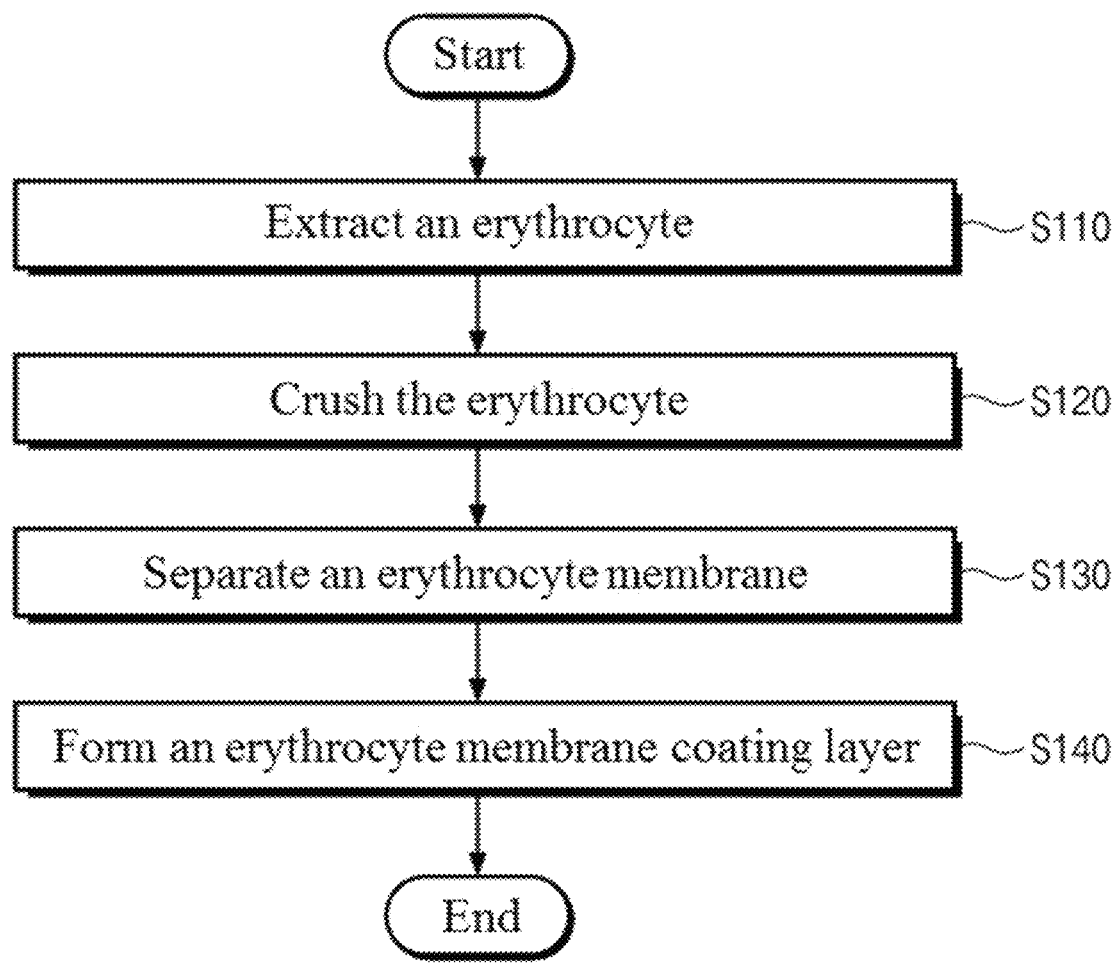
[Fig. 13]

[Fig. 14]
S140

[Fig. 15A]
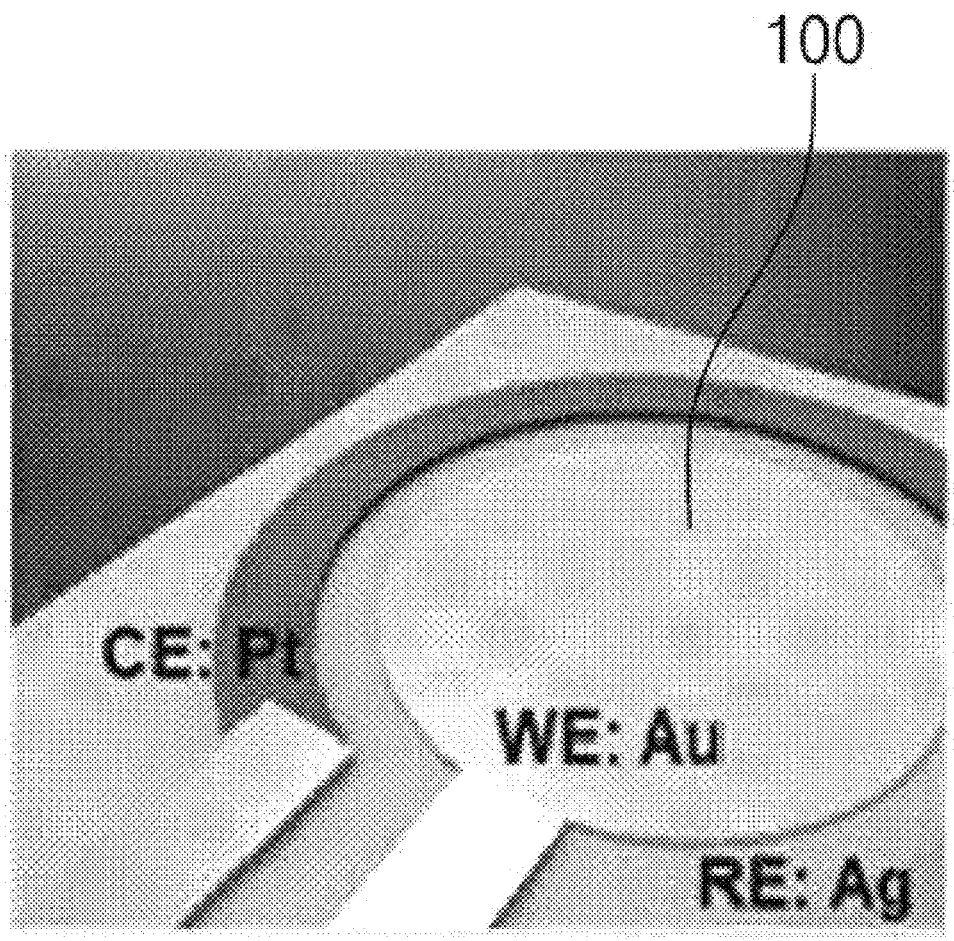

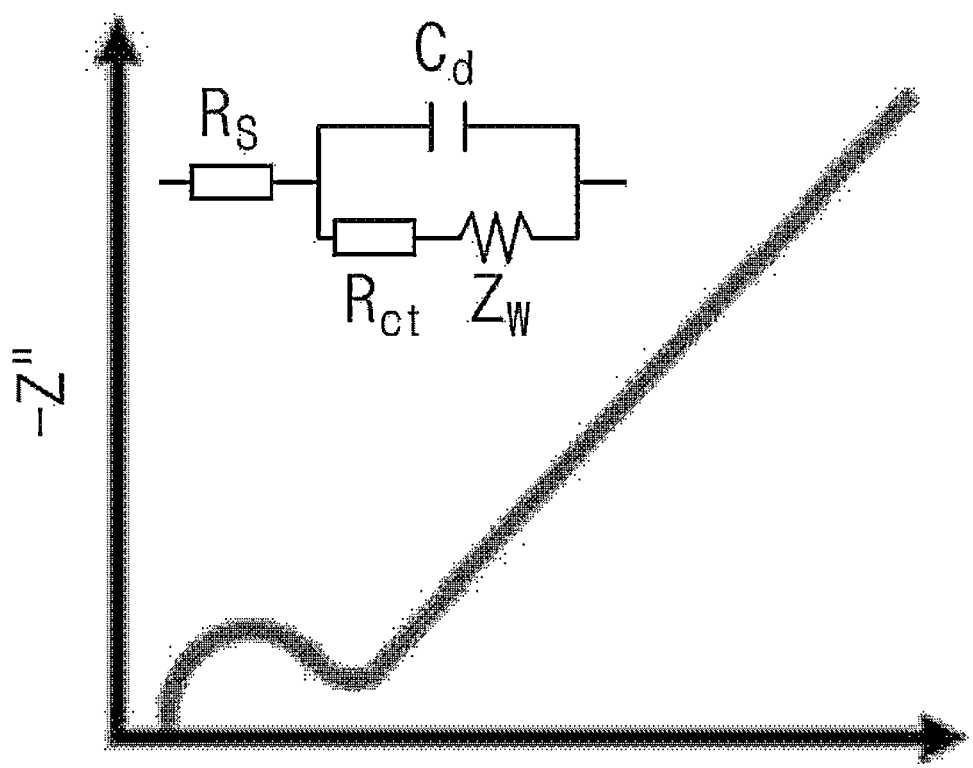
[Fig. 15B]

【Fig. 16】
S140
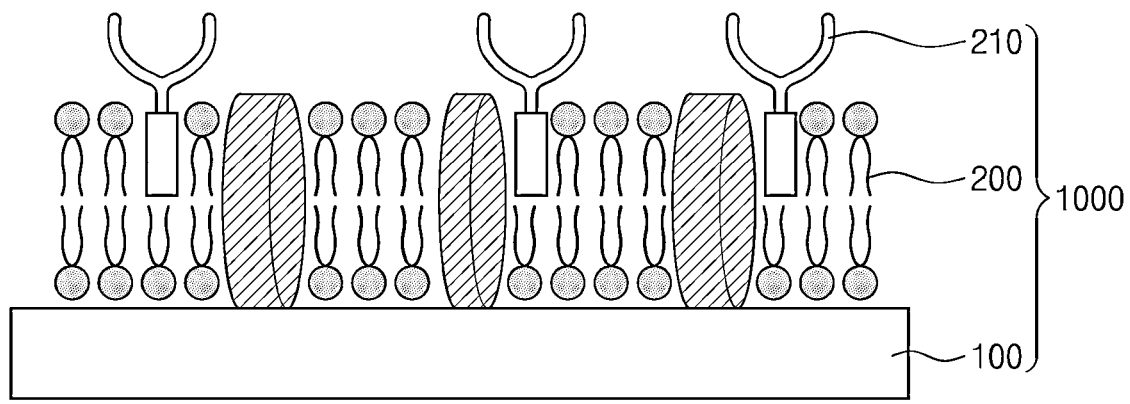

[Fig. 17A]
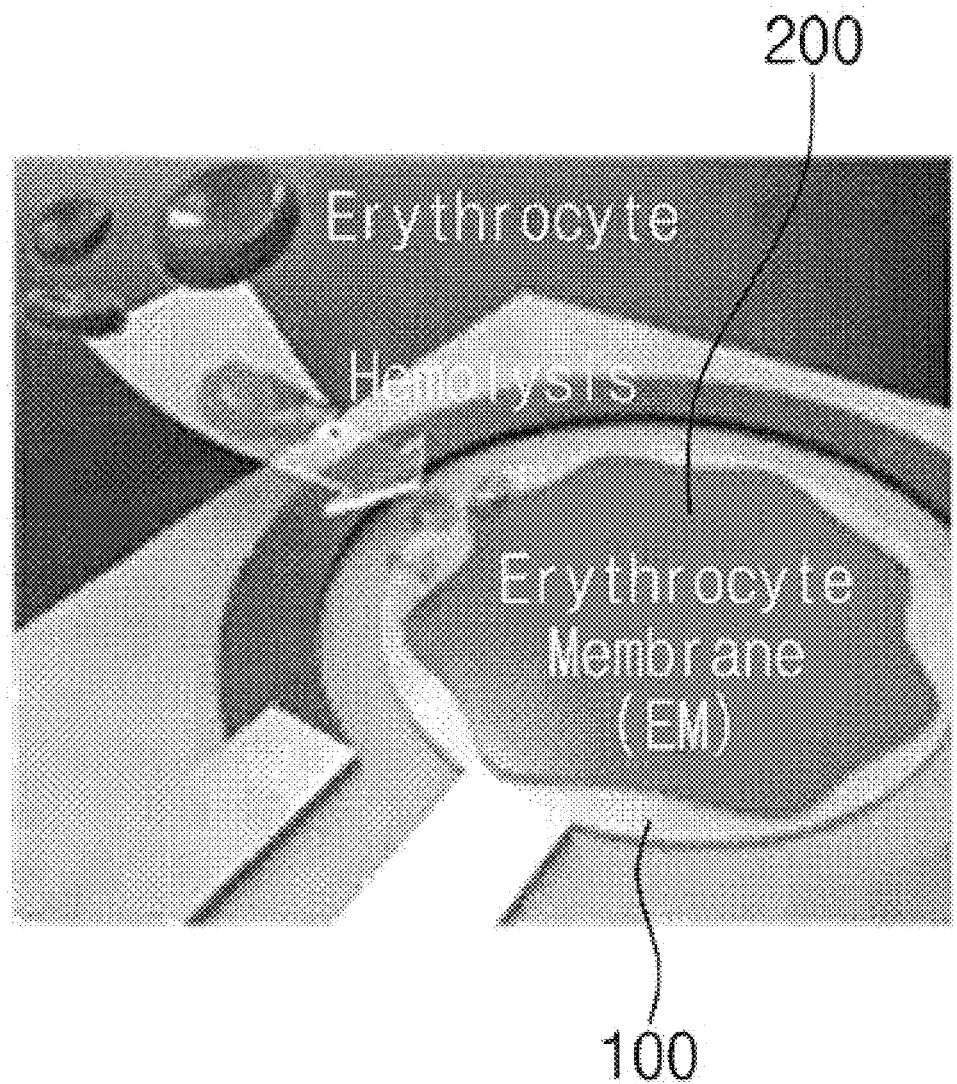

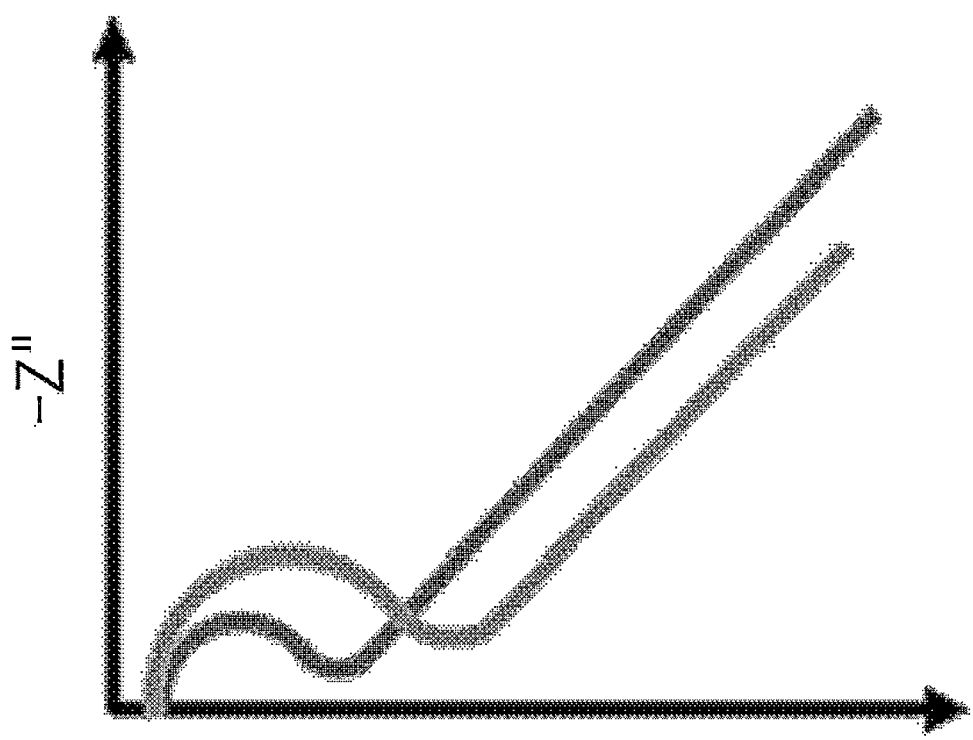
[Fig. 17B]

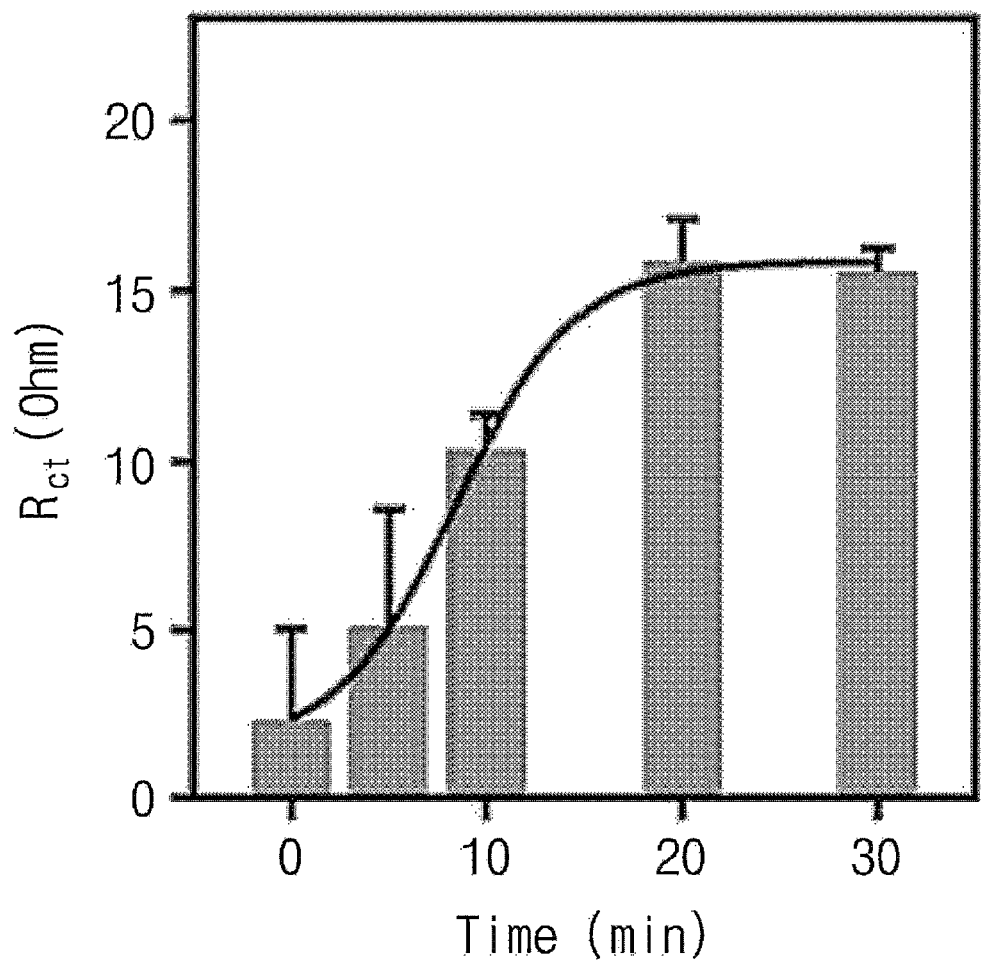
[Fig. 18]

[Fig. 19]
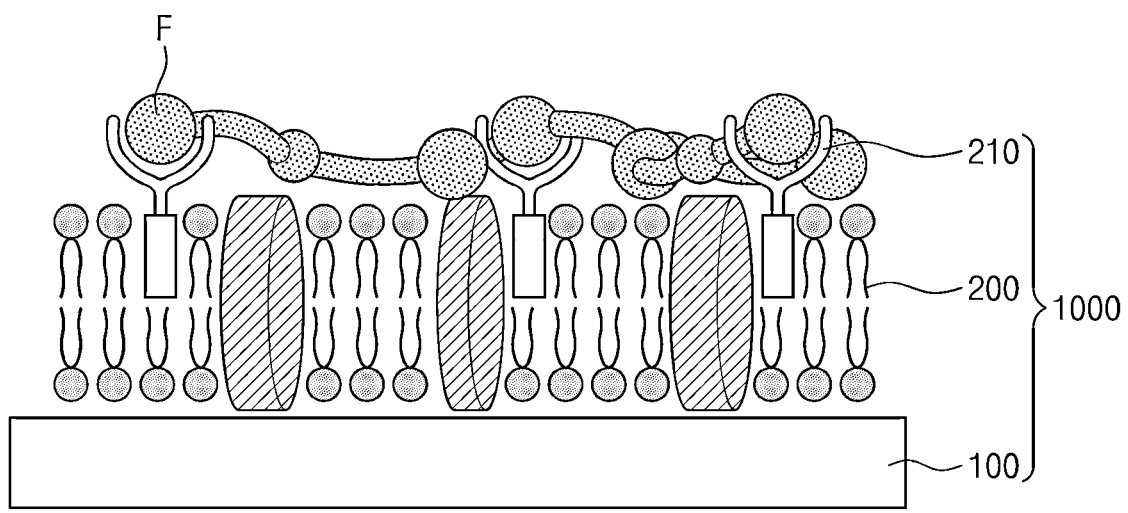

[Fig. 20A]
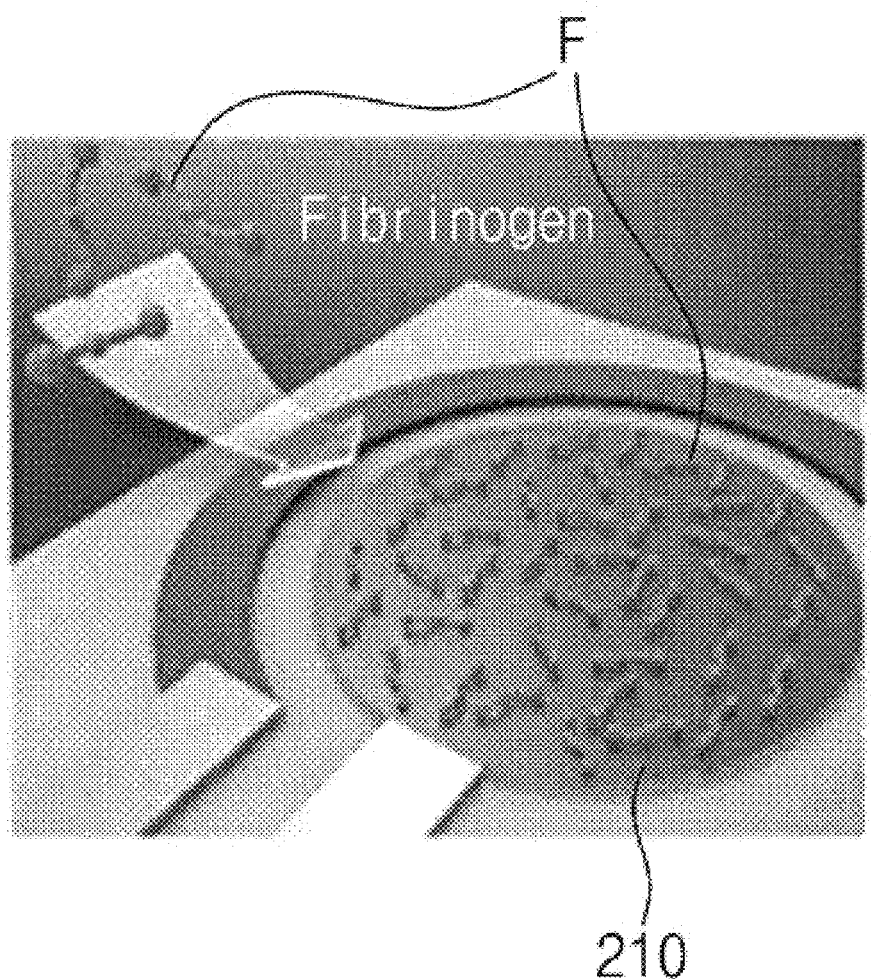

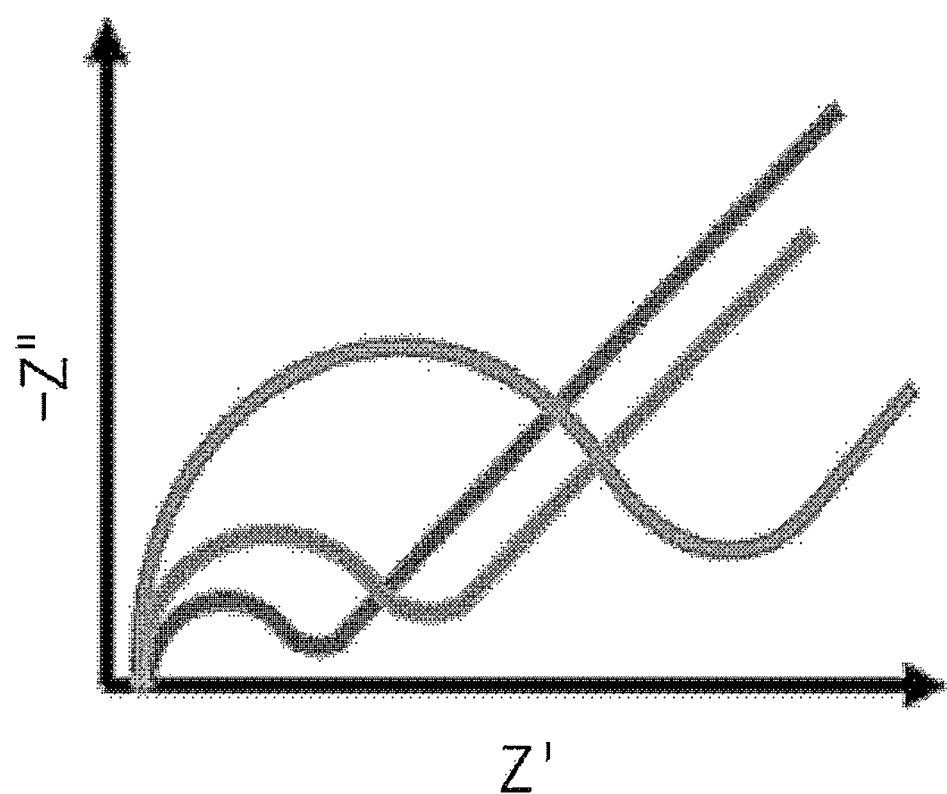
[Fig. 20B]

[Fig. 21A]
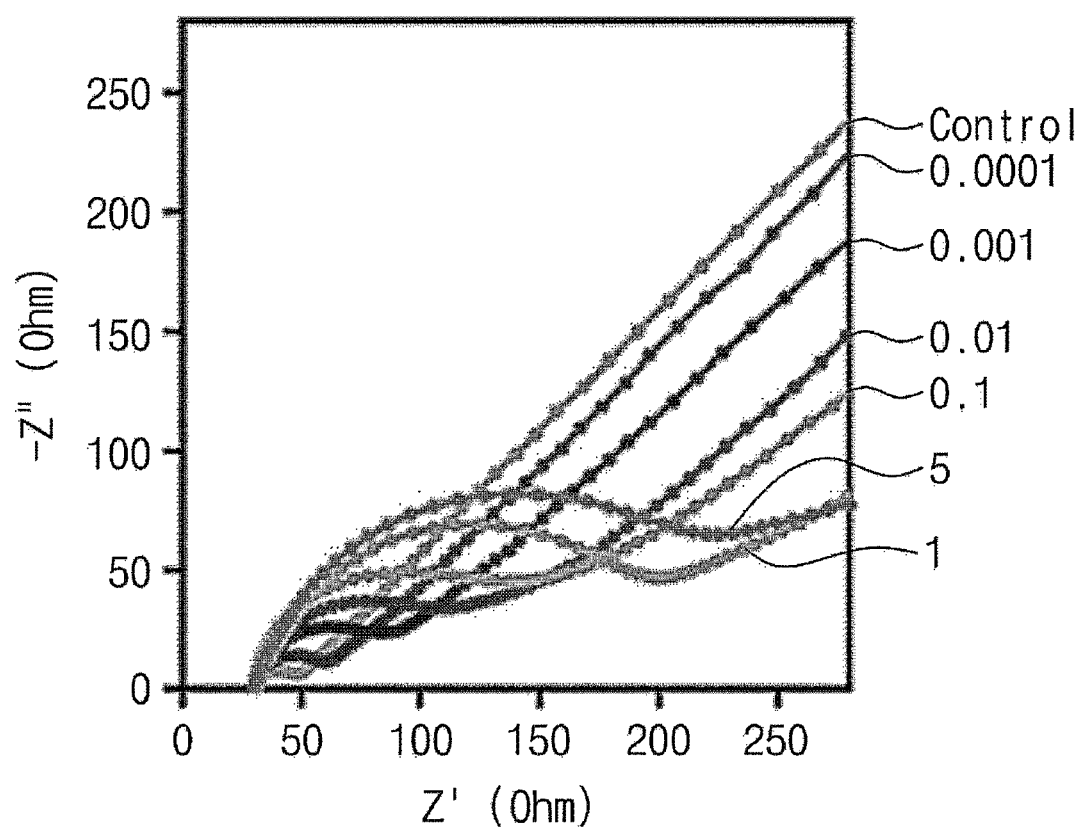

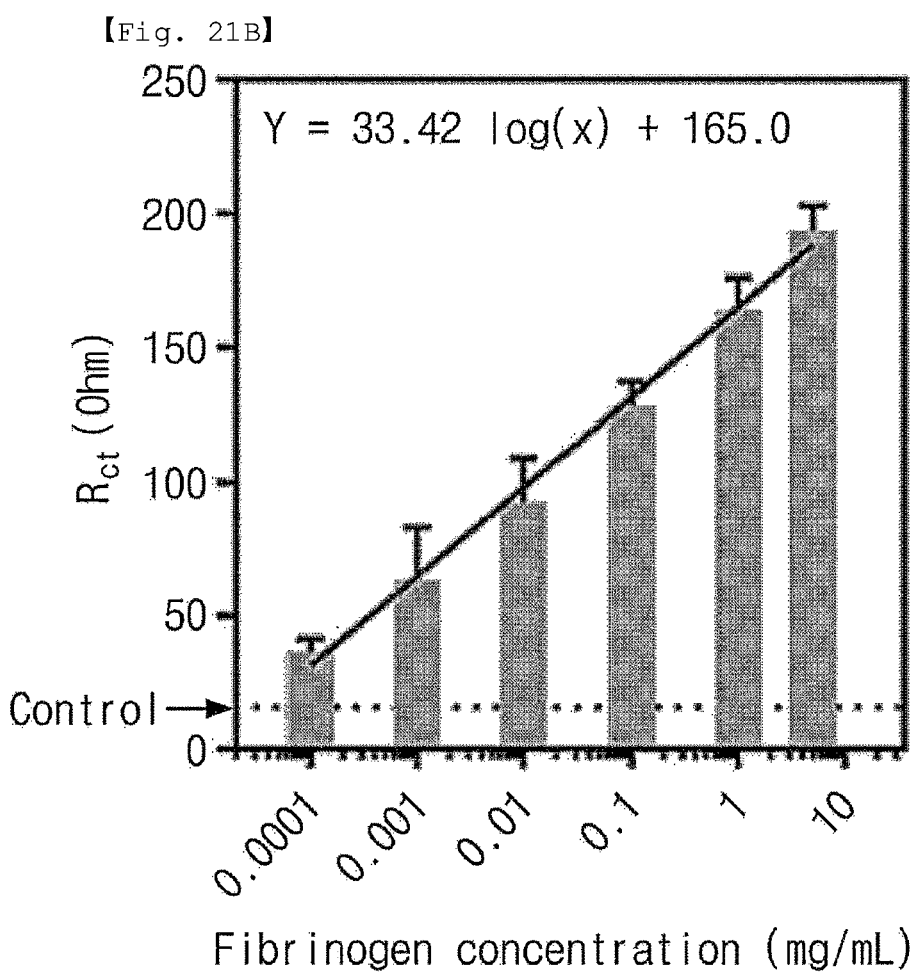
[Fig. 21B]

[Fig. 22]
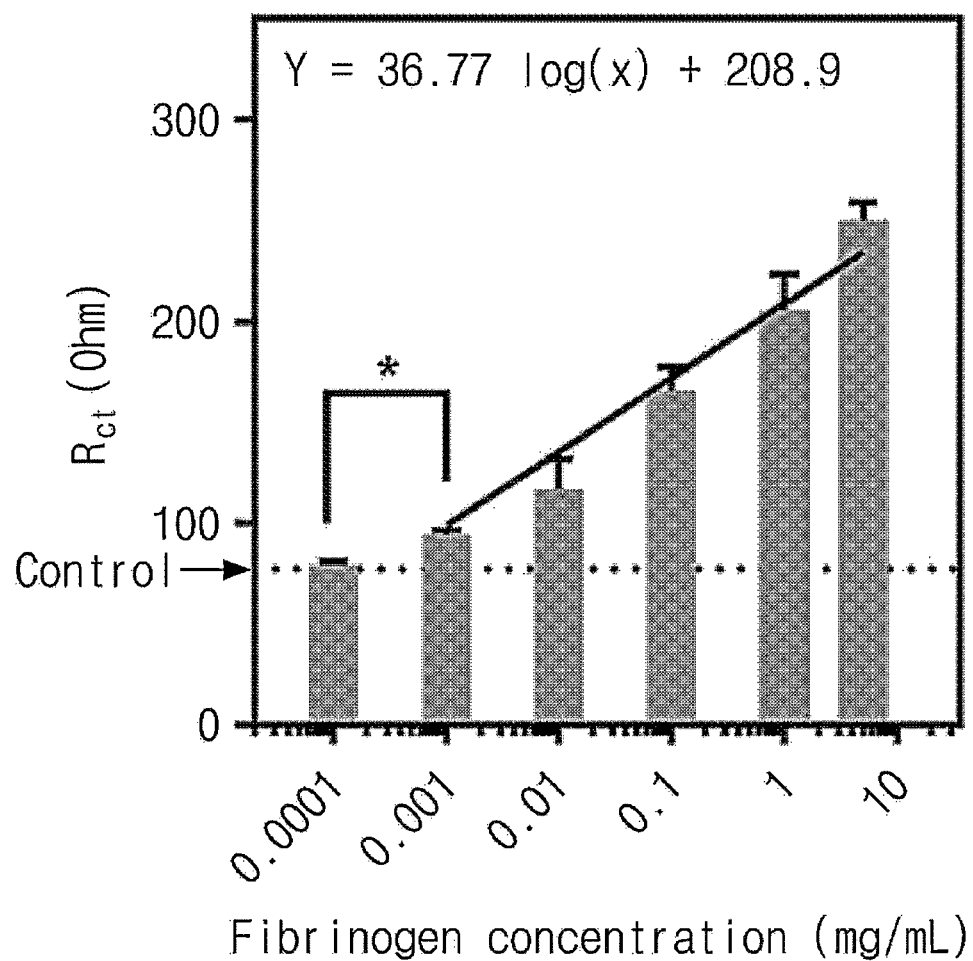

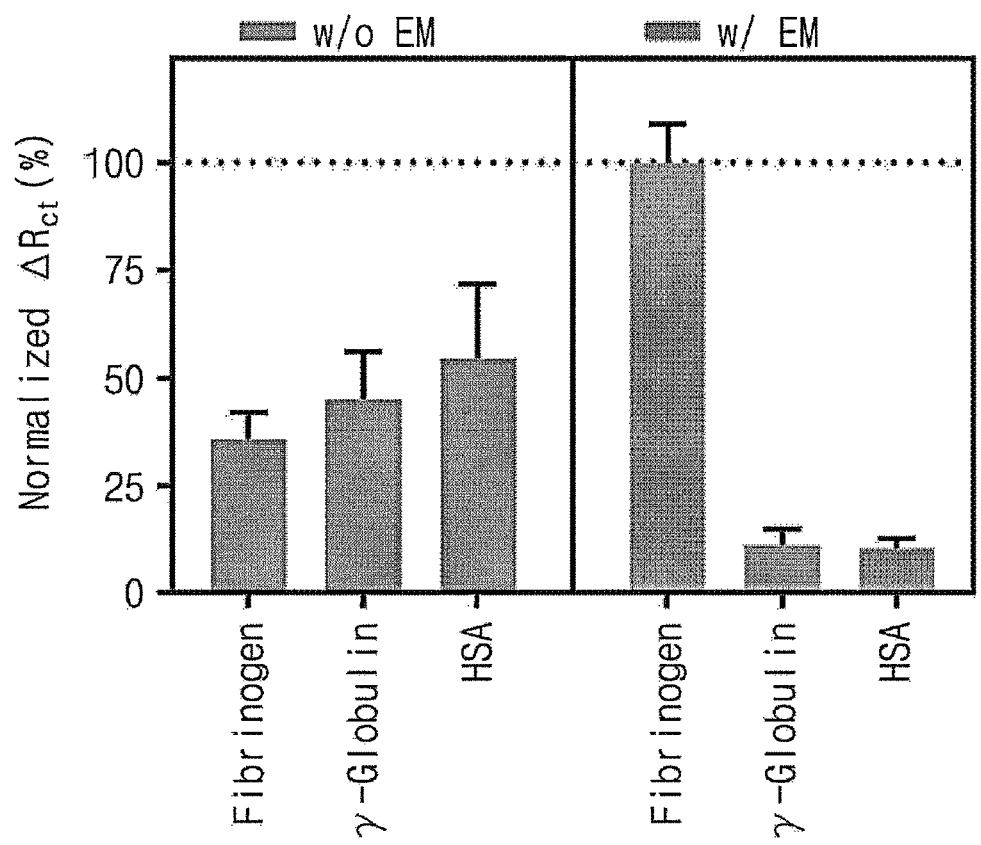
[Fig. 23]

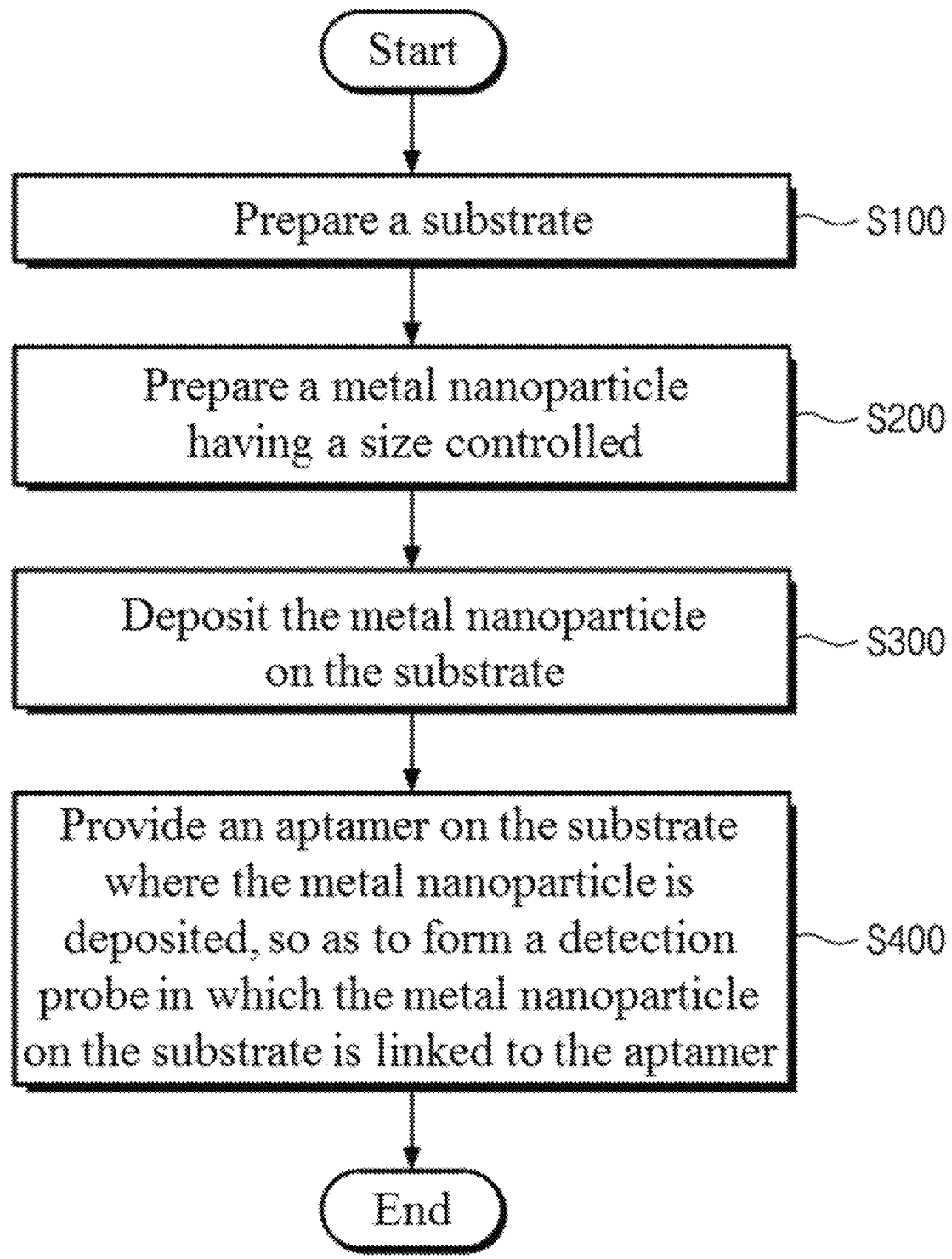
[Fig. 24]

[Fig. 25]
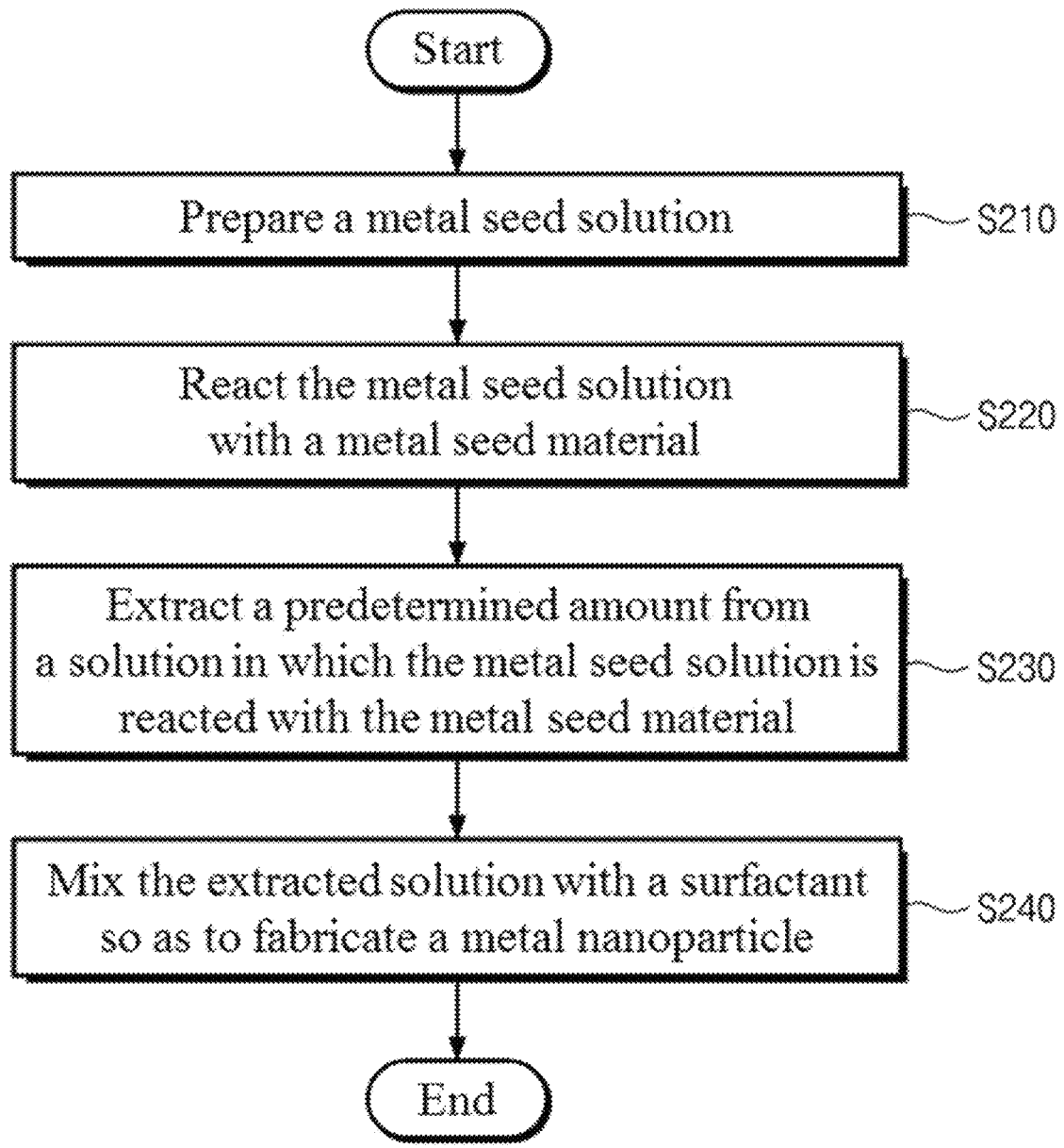

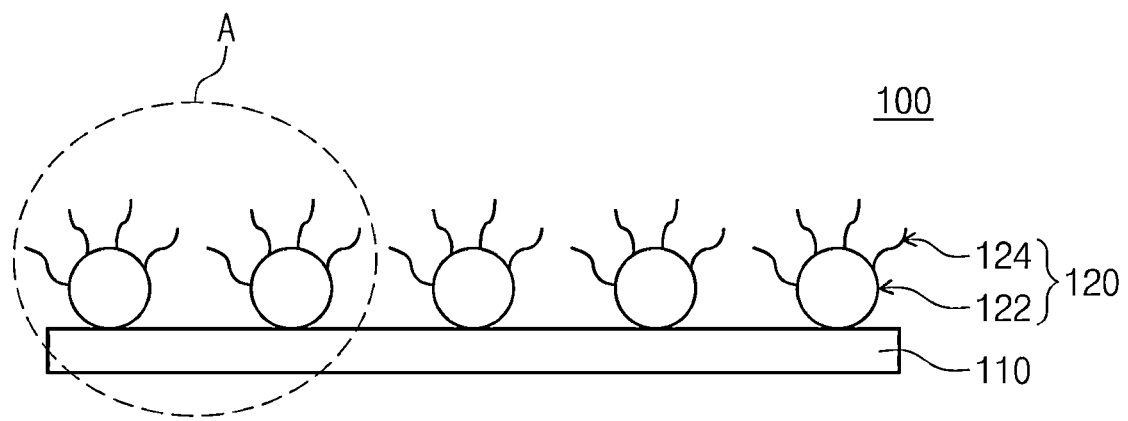
[Fig. 26]

[Fig. 27]
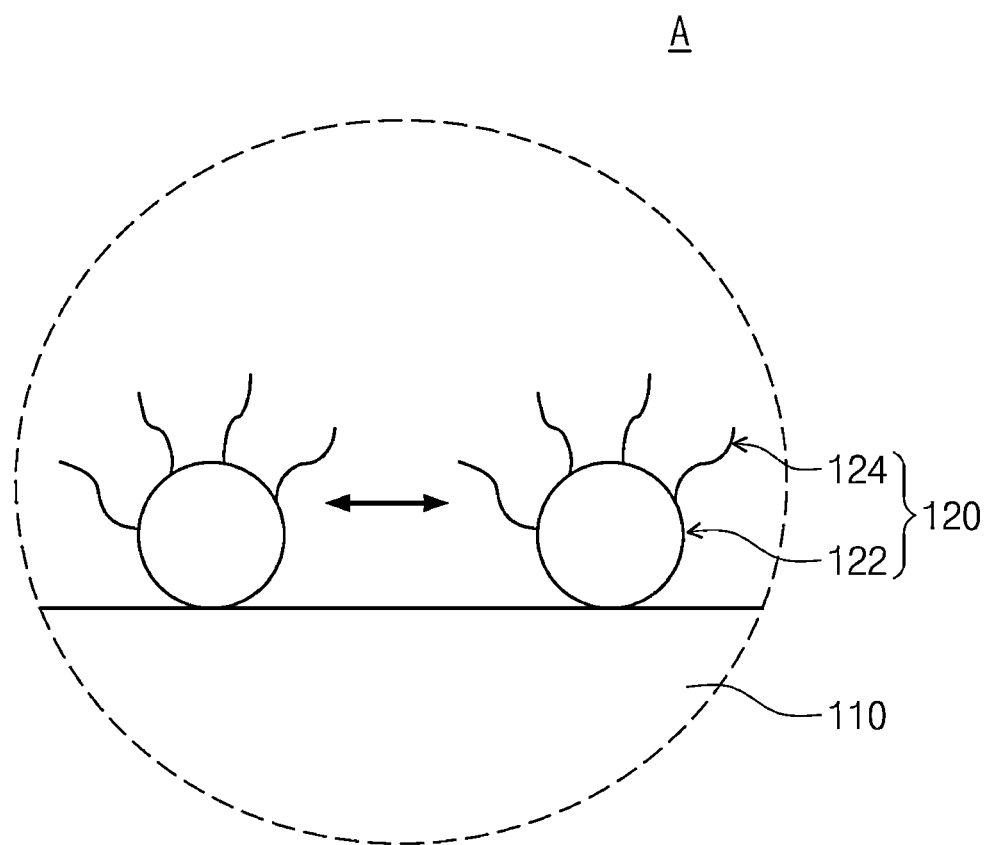

[Fig. 28A]
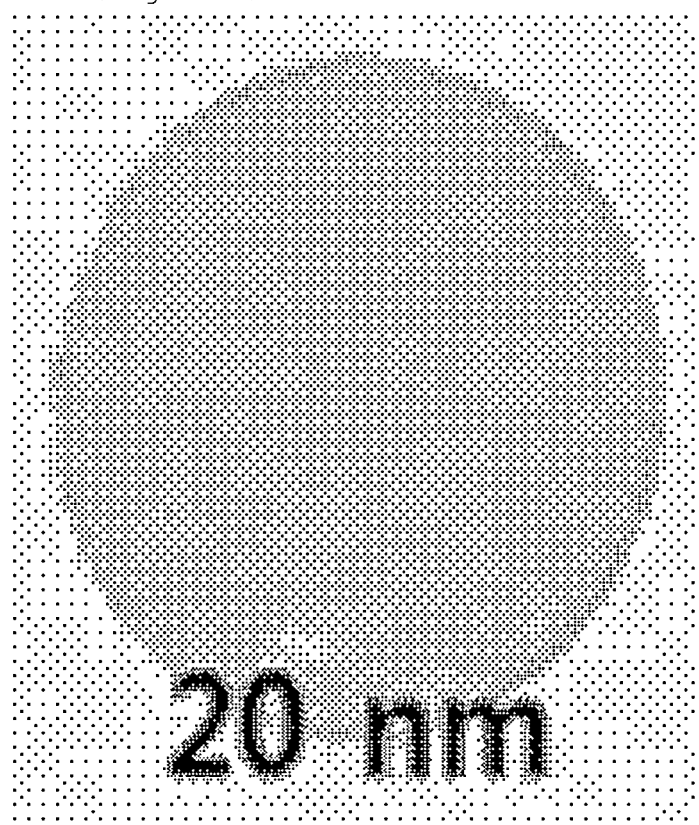

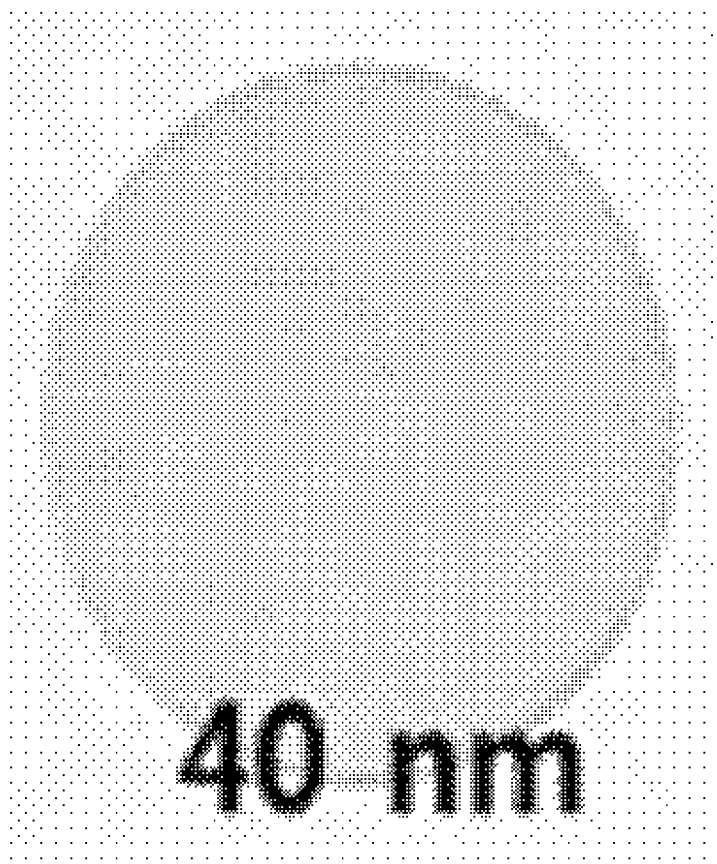
[Fig. 28B]

[Fig. 28C]
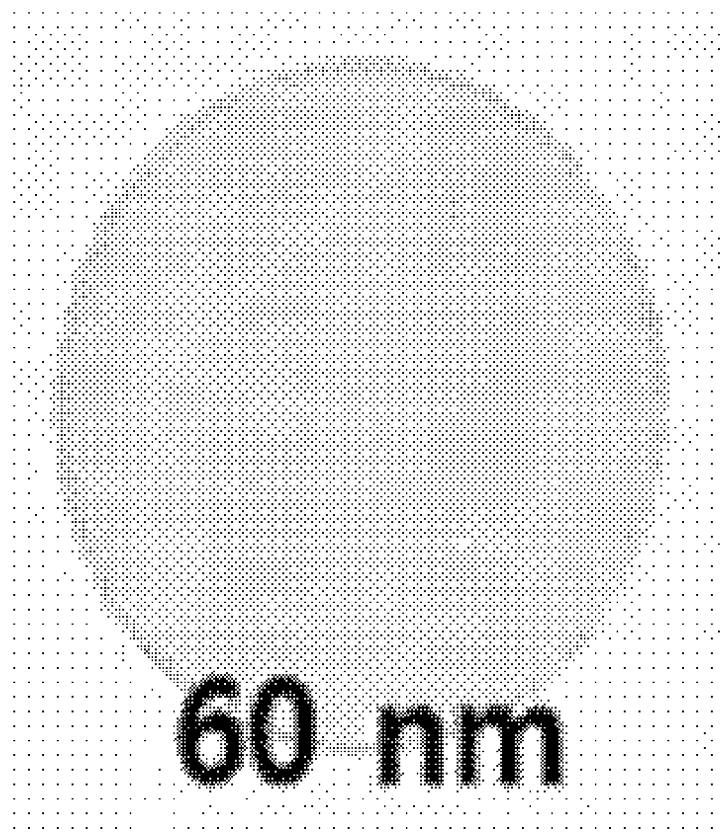

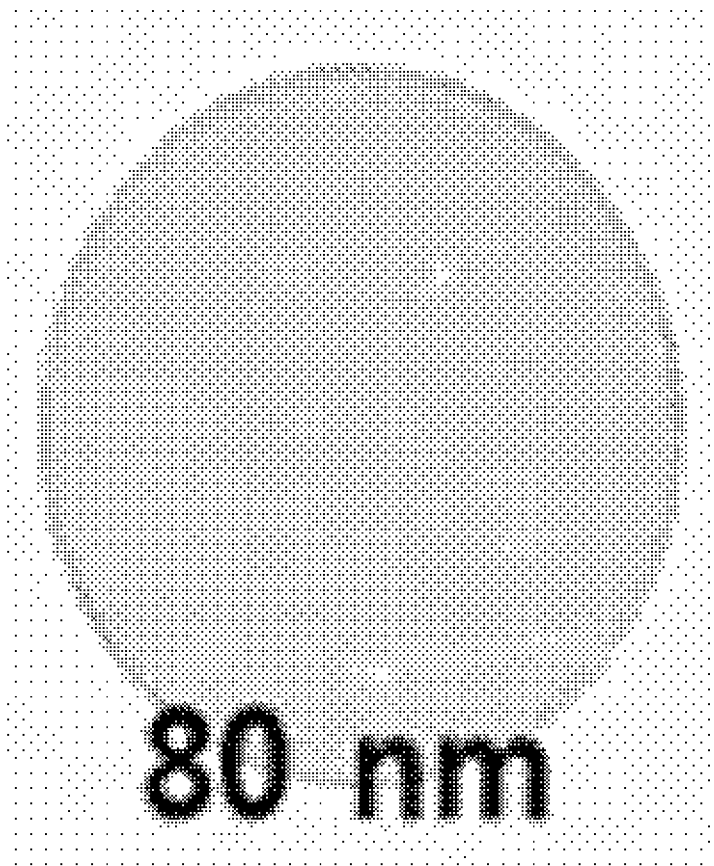
[Fig. 28D]

[Fig. 29A]
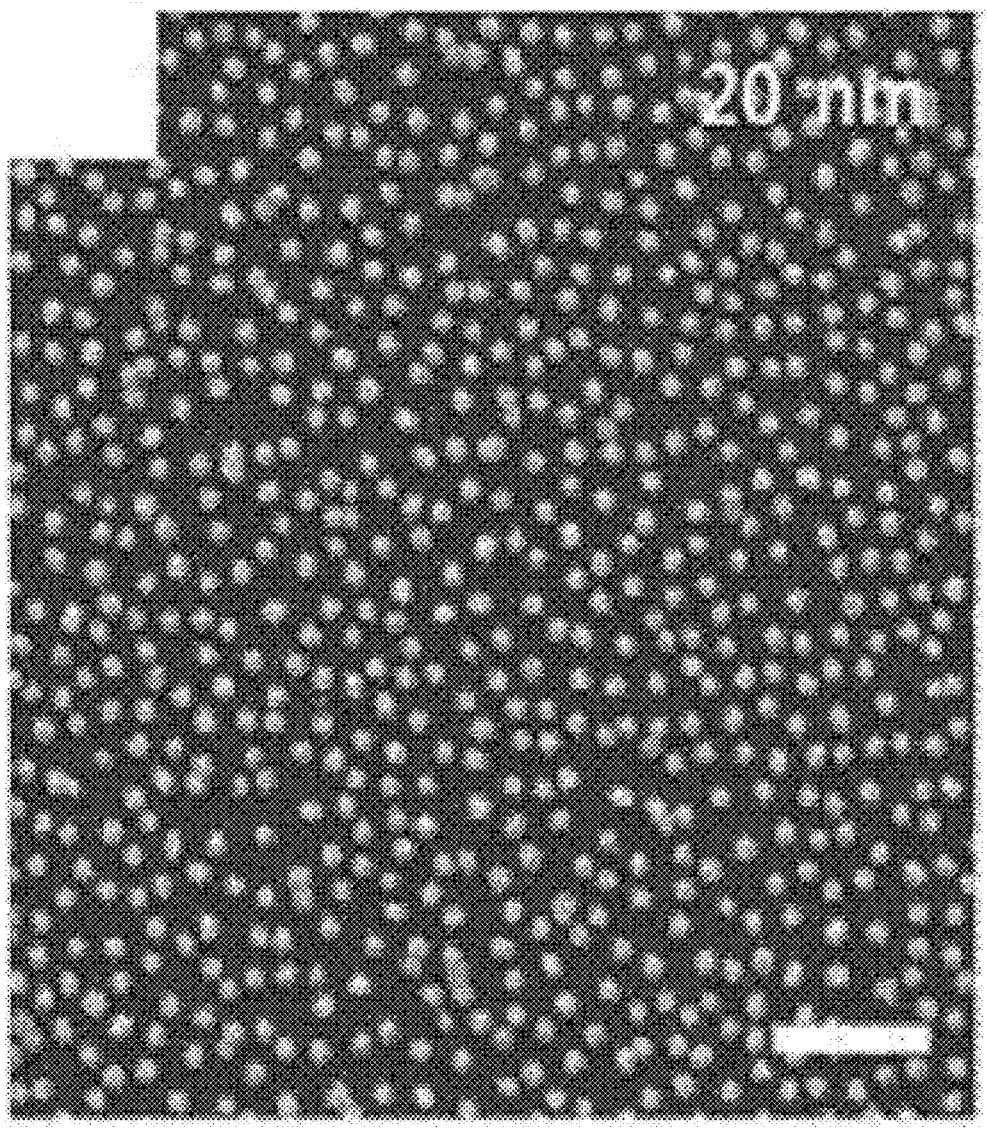

[Fig. 29B]
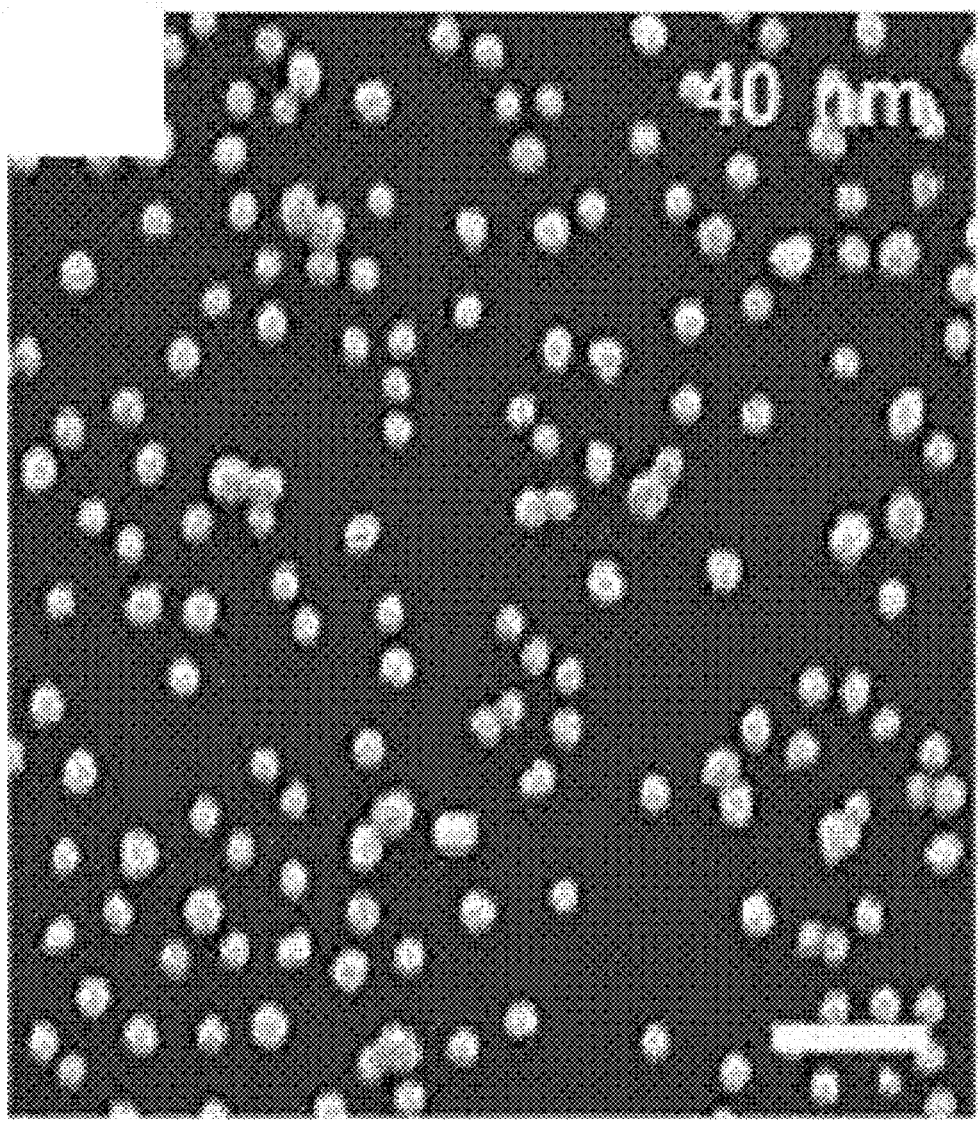

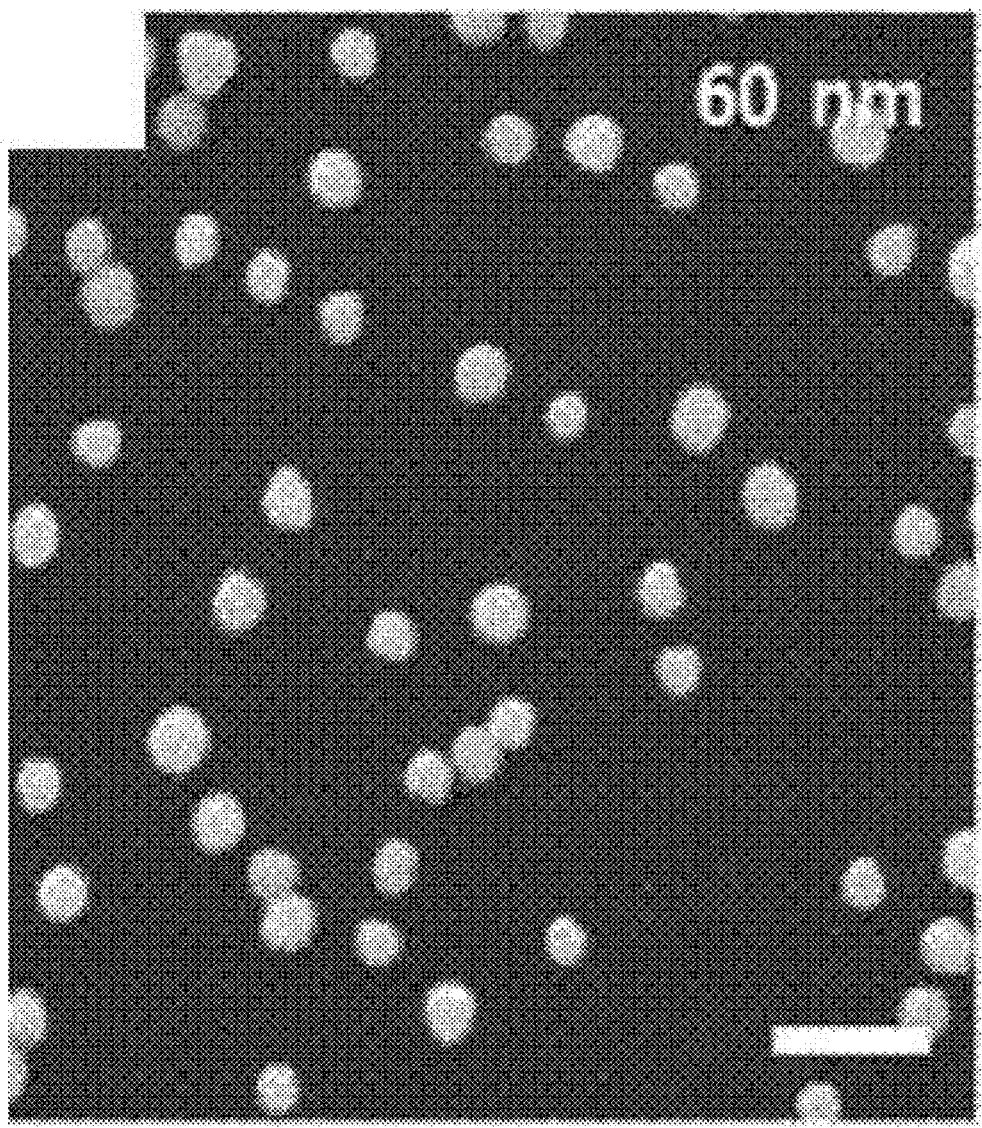
[Fig. 29C]

[Fig. 29D]
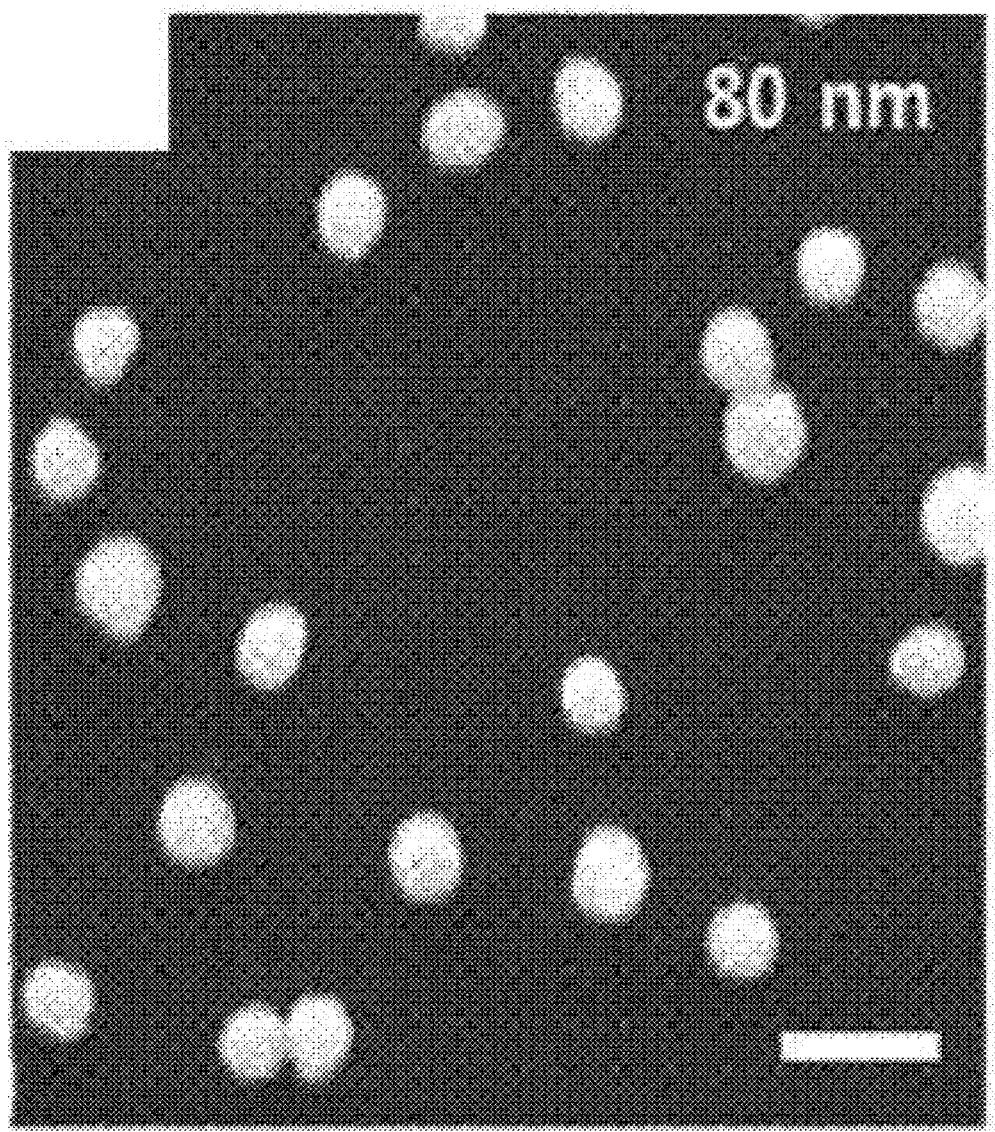

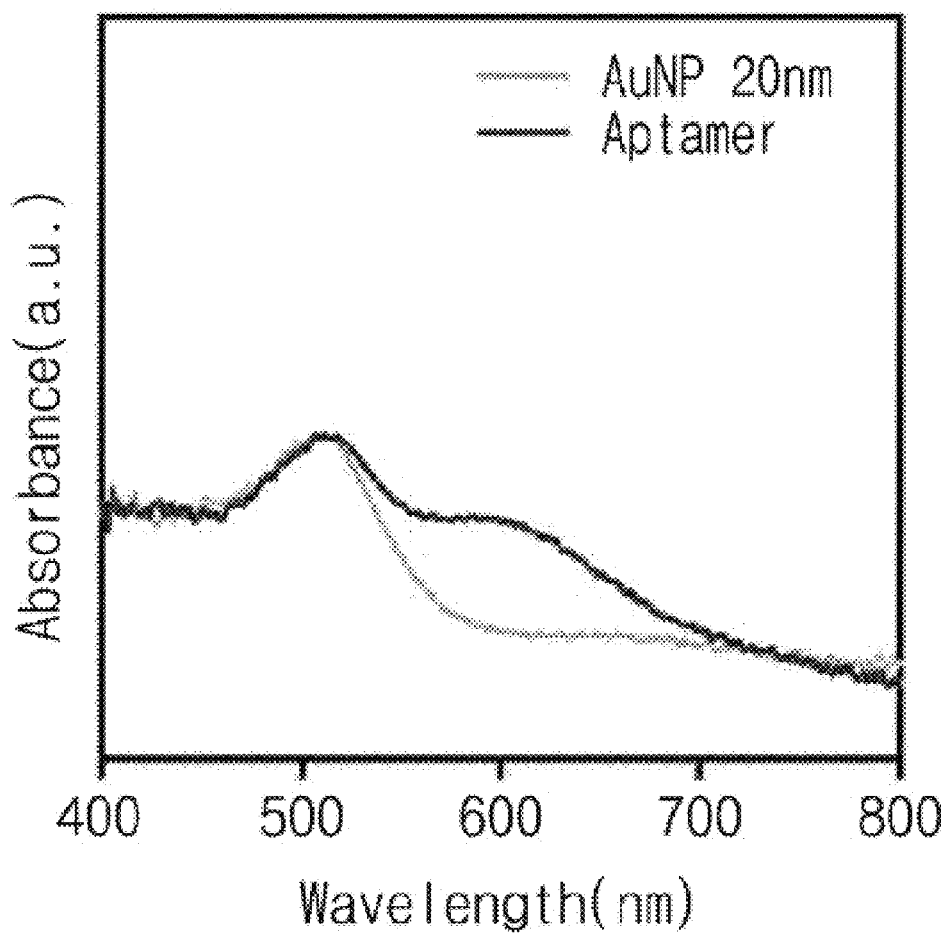
[Fig. 30A]

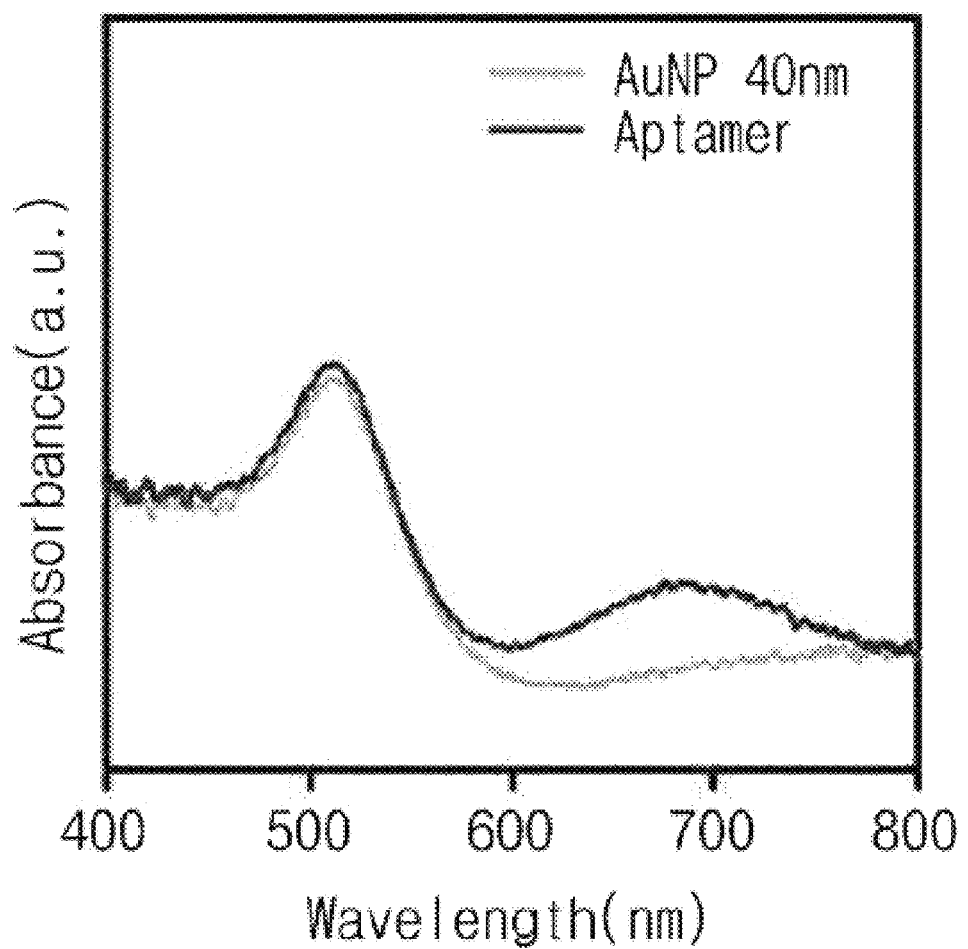
[Fig. 30B]

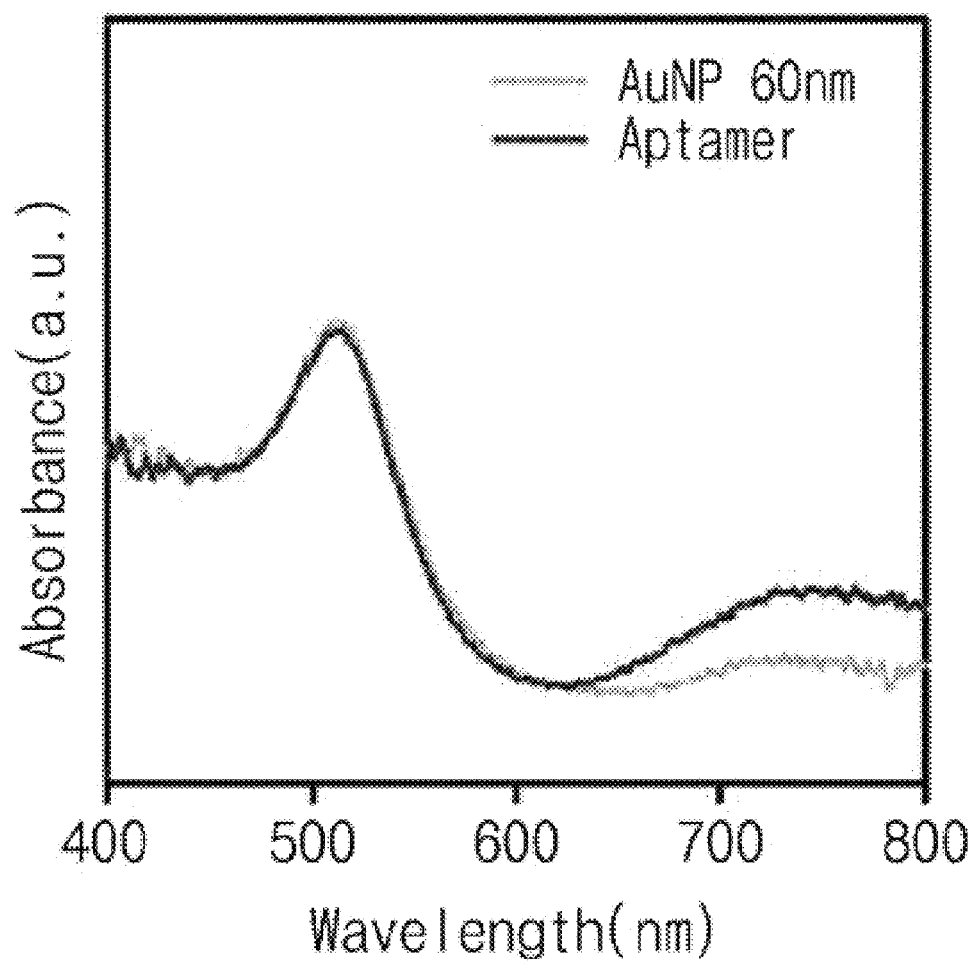
[Fig. 30C]

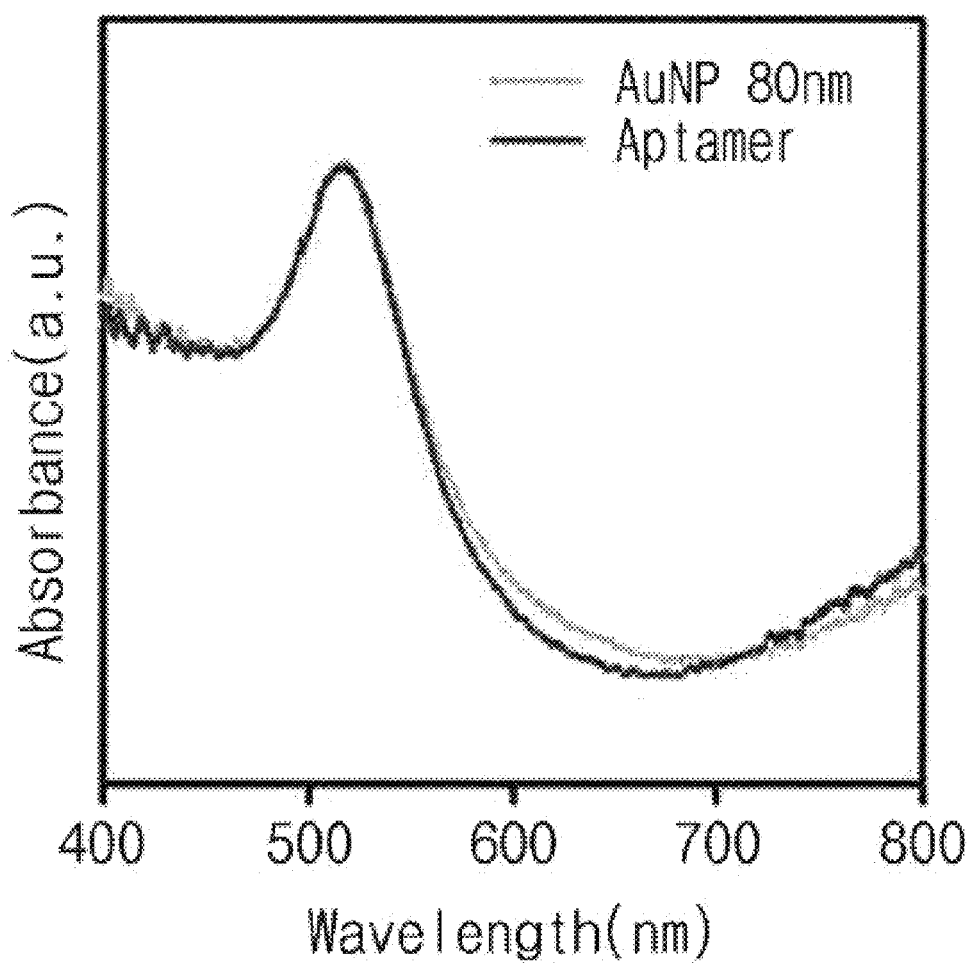
[Fig. 30D]

[Fig. 31A]
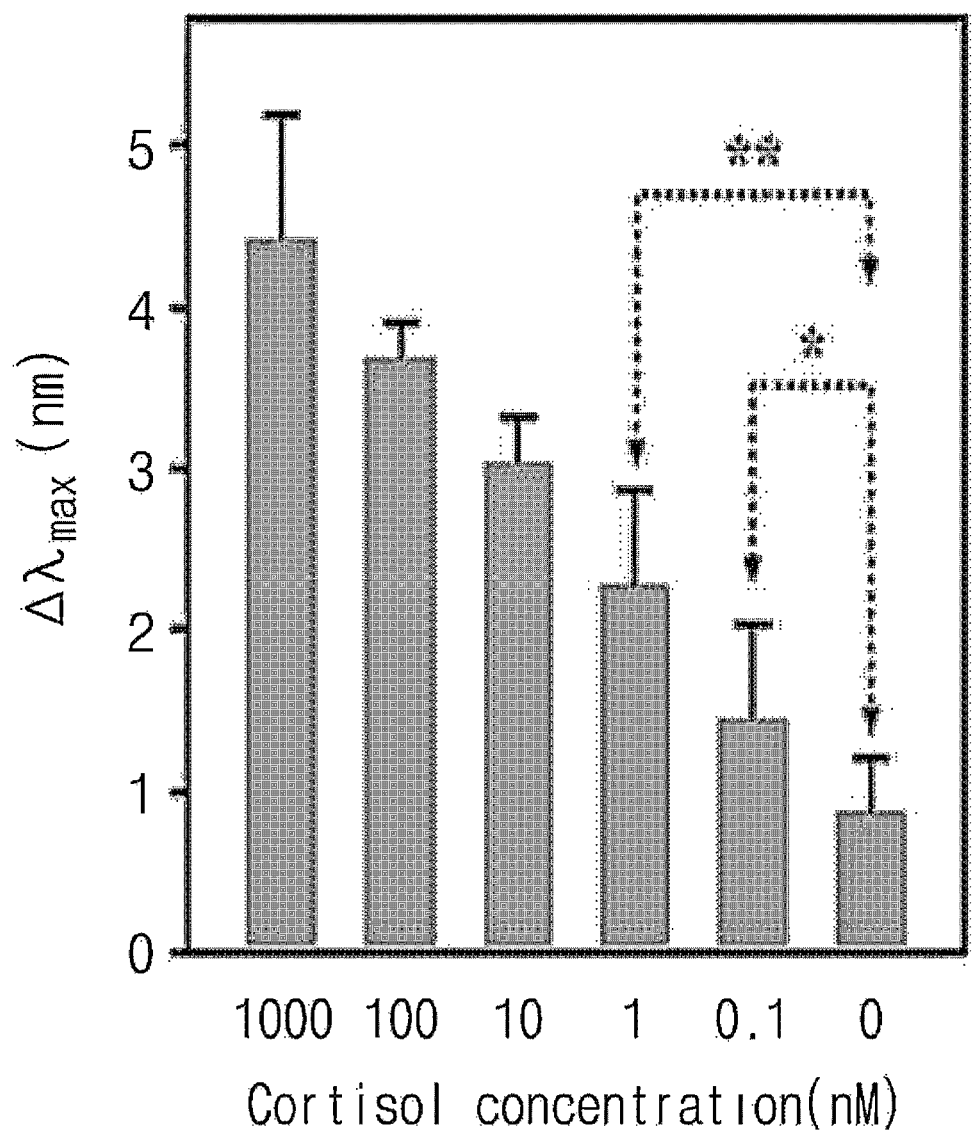

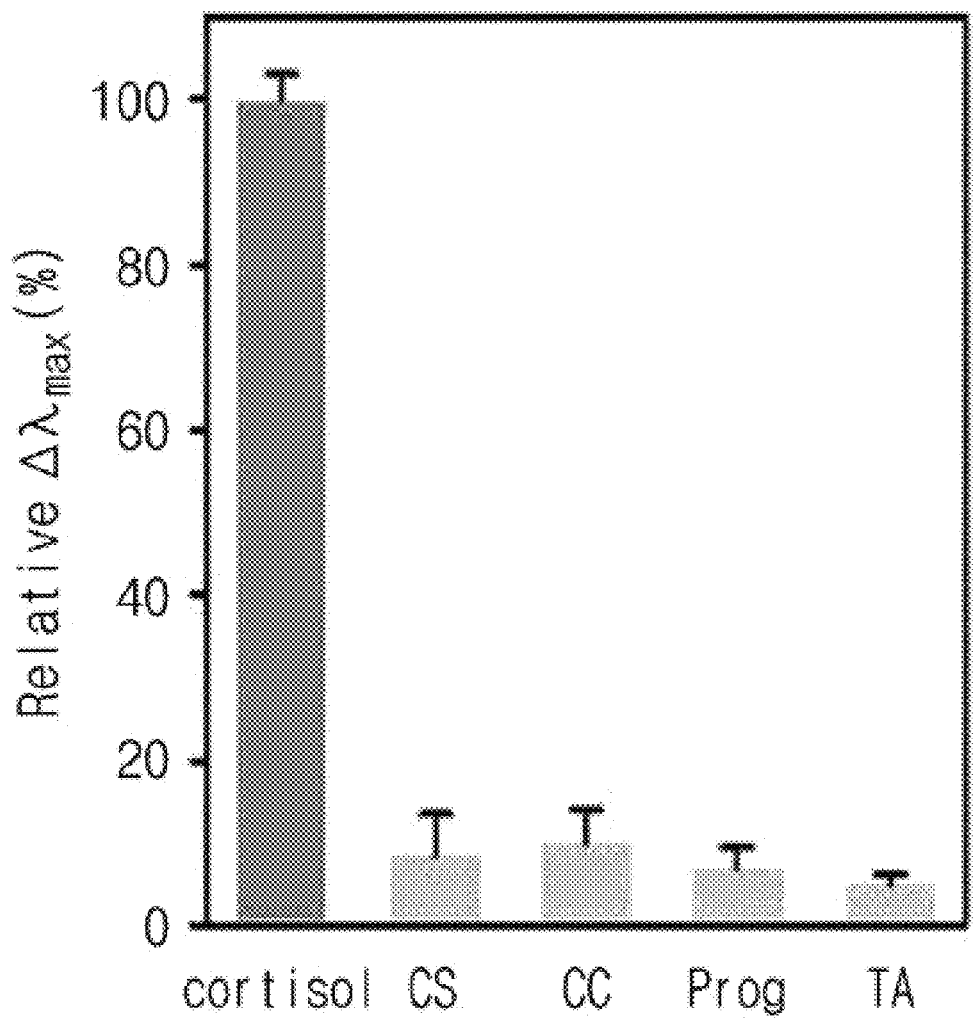

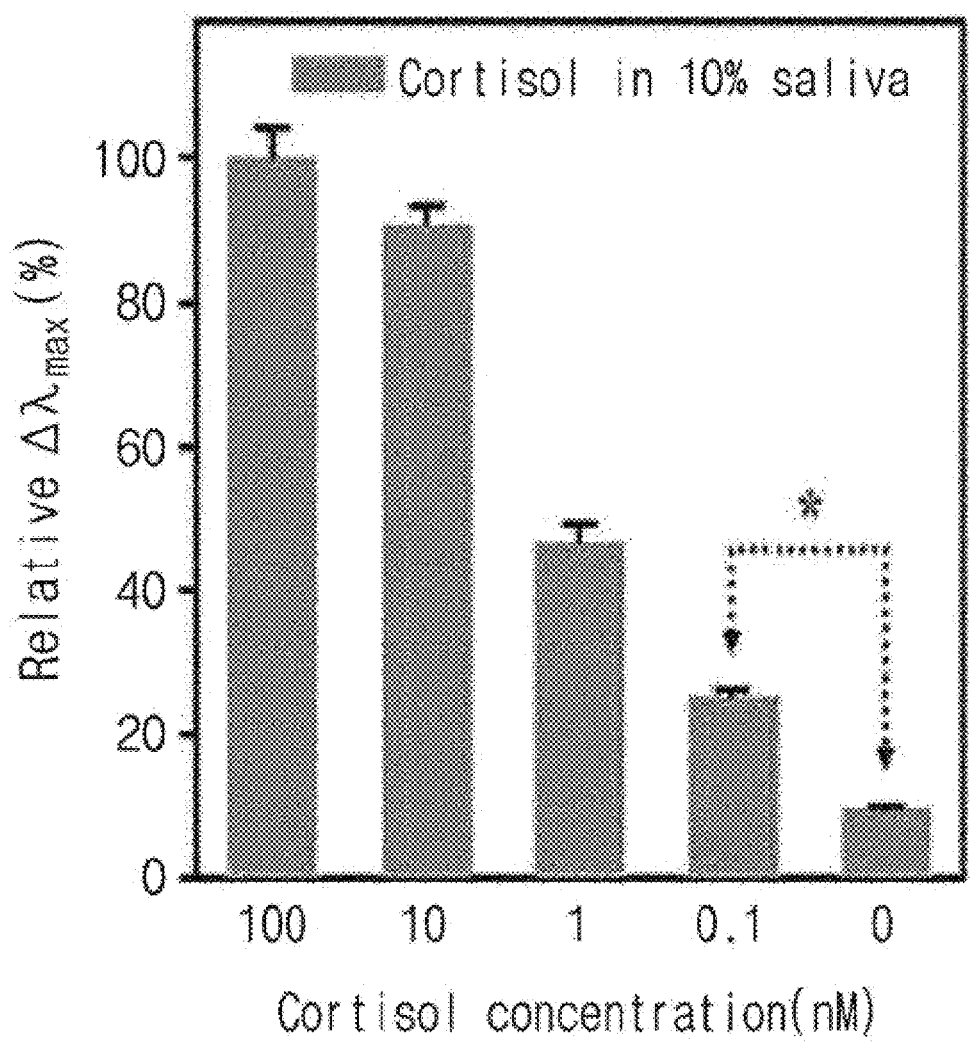
[Fig. 32A]

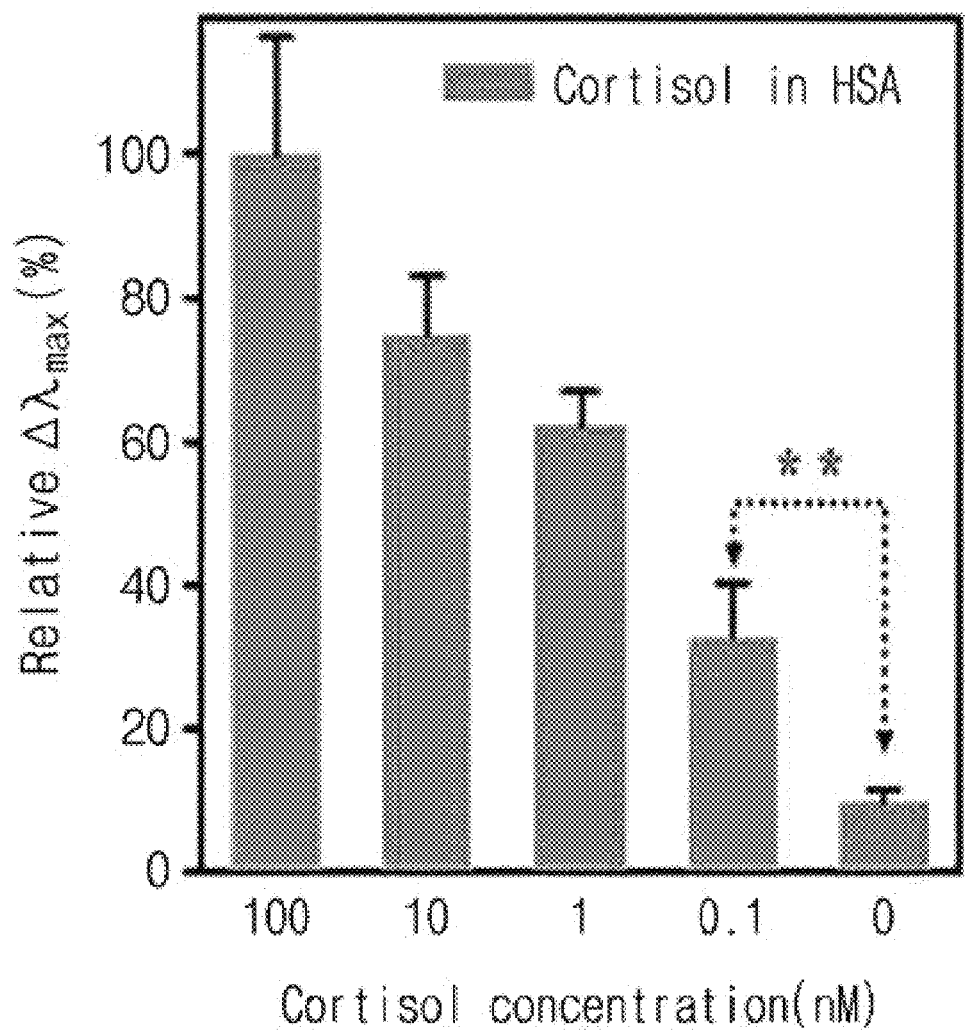
[Fig. 32B]

FIBRINOGEN BIOLOGICAL MATERIAL DETECTION SENSOR INCLUDING AN ERYTHROCYTE MEMBRANE COVERED METAL NANOPARTICLE AND FABRICATING METHOD THEREOF

TECHNICAL FIELD

The present invention relates to a biomaterial detection sensor and a method for fabricating the same and, more specifically, to a fibrinogen detection sensor and a method for fabricating the same, and a bio-stress hormone detection sensor and a method for fabricating the same.

BACKGROUND ART

Among biomaterials, fibrinogen is a soluble protein which is produced in the liver and present in plasma. Fibrinogen turns into insoluble fibrin through an enzyme thrombin, in which the fibrin forms blood clots and thus plays a central role in blood coagulation reactions. Fibrinogen is generally present in plasma at a concentration of about 1.5 to 4.0 g/L. If fibrinogen is present at a level higher than this concentration, cardiovascular disease occurs, and if fibrinogen is present at a level lower than this concentration, hemophilia occurs.

In the case of a prothrombin time test, which is a conventional fibrinogen test method, there is a problem in that the results may vary depending on various conditions such as a blood collection method, a sample storage condition, a sample culture time, a culture temperature, etc. In addition, other test methods, such as enzyme immunoassay, radioimmunoassay, immune turbidity assay, etc., require a specific marker such as an antibody, etc., and there is a problem in that it is difficult to test all of the large areas of excess and deficiency even if the specific marker is used.

Furthermore, among various indicators related to depression, cortisol, which is a representative biomaterial, has a concentration that varies in the body over time and may be analyzed to be used as an index for diagnosing depression. Cortisol is detected in all bodily fluids such as saliva, blood, sweat, etc., but an amount of cortisol detected is too small to be precisely analyzed, and thus many studies have been conducted to analyze cortisol.

An enzyme-linked immunospecific assay (ELISA) is used as a representative method for detecting cortisol in the related art, and this method indirectly detects cortisol by using a reaction of horseradish peroxidase (HRP) and 3,3', 5,5'-tetramethylbenzidine (TMB). More specifically, if a stop solution is added after reacting the HRP and TMB, the resulting mixture turns yellow, but turns more pale yellow as an amount of cortisol increases, which is then compared with a reference solution to detect a concentration of cortisol. In the above-described enzyme-linked immunospecific assay (ELISA), a cortisol antibody is used to immobilize cortisol, and the antibody is also used to detect cortisol in many studies such as colorimetric method, fluorescence analysis, electrophoresis, crystal oscillator balance, surface plasmon resonance, etc. However, many problems have been reported with regard to the methods of detecting cortisol using the antibody, and thus various studies on a method of detecting cortisol without using the antibody have been continuously conducted.

Accordingly, the present inventors have invented a biomaterial detection sensor and a method for fabricating the same so as to solve the above-described problems.

DISCLOSURE

Technical Problem

One technical object of the present invention is to provide a fibrinogen detection sensor selectively reacting with fibrinogen and a method for fabricating the same.

Another technical object of the present invention is to provide a fibrinogen detection sensor with enhanced detection accuracy for fibrinogen and a method for fabricating the same.

Still another technical object of the present invention is to provide a fibrinogen detection sensor with enhanced detection sensitivity for fibrinogen and a method for fabricating the same.

Still another technical object of the present invention is to provide a fibrinogen detection sensor selectively binding to fibrinogen and a method for fabricating the same.

Still another technical object of the present invention is to provide a fibrinogen detection sensor, which is simple and efficient by predicting a concentration of fibrinogen through measurement of charge-transfer resistance values, and a method for fabricating the same.

Still another technical object of the present invention is to provide a fibrinogen detection sensor, which is efficient by simply detecting both deficiency and excess of fibrinogen, and a method for fabricating the same.

Still another technical object of the present invention is to provide a bio-stress hormone detection sensor selectively reacting with cortisol and a method for fabricating the same.

Still another technical object of the present invention is to provide a bio-stress hormone detection sensor with enhanced sensing efficiency (sensitivity) for cortisol and a method for fabricating the same.

Still another technical object of the present invention is to provide a bio-stress hormone detection sensor capable of sensing cortisol from saliva and blood and a method for fabricating the same.

The technical objects of the present invention are not limited to the above.

Technical Solution

First Embodiment

To solve the above technical objects, the present invention may provide a fibrinogen detection sensor.

According to one embodiment, the fibrinogen detection sensor may include a substrate and a detection probe having a metal nanoparticle deposited on the substrate, and an erythrocyte membrane conformally covering the metal nanoparticle, in which the detection probe may selectively react with fibrinogen.

According to one embodiment, a plurality of detection probes may be disposed on the substrate, in which, among the plurality of detection probes, a distance between first and second metal nanoparticles adjacent to each other before reacting with the fibrinogen may be the same as a distance between the first and second metal nanoparticles after reacting with the fibrinogen.

According to one embodiment, the erythrocyte membrane may conformally cover both the substrate and the metal nanoparticle.

According to one embodiment, one region of the erythrocyte membrane may be disposed to be spaced apart from the substrate by a predetermined distance with the metal nanoparticle interposed therebetween, and the other region of the erythrocyte membrane may be disposed to come into direct contact with the substrate.

According to one embodiment, the erythrocyte membrane may have the metal nanoparticle fixed on the substrate.

According to one embodiment, a thickness of the erythrocyte membrane may be 2 nm or less.

According to one embodiment, the fibrinogen detection sensor may be configured to sense the fibrinogen at a concentration of 0.001 mg/mL or more.

According to one embodiment, the fibrinogen detection sensor may be configured to linearly sense the fibrinogen in a concentration range of 0.001 to 10 mg/mL.

According to one embodiment, the metal nanoparticle may include a gold (Au) nanoparticle.

According to one embodiment, a local surface plasmon resonance signal of the substrate may vary if the detection probe selectively reacts with the fibrinogen.

To solve the above technical objects, the present invention may provide a method for fabricating a fibrinogen detection sensor.

According to one embodiment, the method for fabricating the fibrinogen detection sensor may include: preparing a substrate and a metal nanoparticle; depositing the metal nanoparticle on the substrate; extracting an erythrocyte membrane from an erythrocyte; and providing the erythrocyte membrane on the substrate where the metal nanoparticle is deposited, so as to form a detection probe including the metal nanoparticle on the substrate and the erythrocyte membrane conformally covering the metal nanoparticle.

According to one embodiment, the extracting of the erythrocyte membrane may include separating blood plasma from whole blood and crushing an erythrocyte in the plasma to remove cytoplasm therefrom.

According to one embodiment, a concentration of the erythrocyte membrane provided on the substrate where the metal nanoparticle is deposited may be 0.05 v/v % or less.

Second Embodiment

To solve the above technical objects, the present invention may provide a method for fabricating a fibrinogen detection sensor.

According to one embodiment, the method for fabricating the fibrinogen detection sensor may include: extracting an erythrocyte from blood; crushing the extracted erythrocyte; separating an erythrocyte membrane from the crushed erythrocyte; and providing the erythrocyte membrane on an electrode so as to form an erythrocyte membrane coating layer having a fibrinogen receptor.

According to one embodiment, the forming of the erythrocyte membrane coating layer may be performed at a predetermined temperature for 20 minutes or longer.

According to one embodiment, the erythrocyte membrane coating layer may be formed of a single erythrocyte membrane.

According to one embodiment, the extracting and the separating may be performed through centrifugation.

To solve the above technical objects, the present invention may provide the fibrinogen detection sensor.

According to one embodiment, the fibrinogen detection sensor may include an electrode and an erythrocyte membrane coating layer formed on the electrode and made of an erythrocyte membrane having a fibrinogen receptor, in which the biomaterial detection sensor may provide a charge transfer resistance value that varies depending on a reaction of fibrinogen to the fibrinogen receptor.

According to one embodiment, the erythrocyte membrane coating layer may be formed of a single erythrocyte membrane.

According to one embodiment, the charge transfer resistance value may linearly vary depending on a fibrinogen concentration in a fibrinogen concentration range of 0.1 to 5000 μg/mL including deficiency and excess of fibrinogen.

According to one embodiment, a change in the charge transfer resistance may be detected in a fibrinogen concentration of 0.049 μg/mL or more.

According to one embodiment, the fibrinogen receptor may be inhibited from non-specifically binding to proteins other than fibrinogen.

Third Embodiment

To solve the above technical objects, the present invention may provide a biohormone detection sensor.

According to one embodiment, the biohormone detection sensor may include a substrate and a detection probe having a metal nanoparticle deposited on the substrate, and an aptamer linked to the metal nanoparticle, in which the detection probe may selectively react with cortisol.

According to one embodiment, the metal nanoparticle may include a gold (Au) nanoparticle, in which a reactivity between the detection probe and the cortisol may be controlled depending on a size of the metal nanoparticle.

According to one embodiment, a size of the metal nanoparticle may be 80 nm or more.

According to one embodiment, a size of the aptamer may be 85 mer.

According to one embodiment, a plurality of detection probes may be disposed on the substrate, in which the plurality of detection probes may be spaced apart from each other, respectively.

According to one embodiment, the biohormone detection sensor may be configured to sense the cortisol at a concentration of 1 nM or more.

According to one embodiment, a local surface plasmon resonance signal of the substrate may vary if the detection probe selectively reacts with the cortisol.

To solve the above technical objects, the present invention may provide a method for fabricating a biohormone detection sensor.

According to one embodiment, the method for fabricating the biohormone detection sensor may include: preparing a substrate; preparing a metal nanoparticle having a size controlled; depositing the metal nanoparticle on the substrate; and providing an aptamer on the substrate where the metal nanoparticle is deposited, so as to form a detection probe in which the metal nanoparticle on the substrate is linked to the aptamer.

According to one embodiment, the preparing of the metal nanoparticle having a size controlled may include: preparing a metal seed solution; reacting the metal seed solution with a metal seed material; extracting a predetermined amount from a solution in which the metal seed solution is reacted with the metal seed material; and mixing the extracted solution with a surfactant so as to fabricate a metal nanoparticle.

According to one embodiment, the reacting of the metal seed solution with the metal seed material, the extracting, and the mixing with the surfactant may be formed as a unit process, and the unit process is repeated a plurality of times.

According to one embodiment, as the number of repeating the unit process increases, a size of the metal nanoparticle may increase.

According to one embodiment, the metal seed material may include hydrogen tetrachloroauric(III) acid ($HAuCl_4$), and the surfactant may include trisodium citrate.

Advantageous Effects

According to a first embodiment of the present invention, a fibrinogen detection sensor may include a substrate and a detection probe having a metal nanoparticle deposited on the substrate, and an erythrocyte membrane conformally covering the metal nanoparticle, in which the detection probe may selectively react with fibrinogen. In addition, a local surface plasmon resonance signal of the substrate may vary if the detection probe selectively reacts with the cortisol. Accordingly, the fibrinogen detection sensor according to the above embodiment may detect fibrinogen with high sensitivity through a simple method for measuring a change in the local surface plasmon resonance signal without an additional marker.

According to a second embodiment of the present invention, a method for preparing a fibrinogen detection sensor may include: extracting an erythrocyte from blood; crushing the extracted erythrocyte; separating an erythrocyte membrane from the crushed erythrocyte; and providing the erythrocyte membrane on an electrode so as to form an erythrocyte membrane coating layer having a fibrinogen receptor.

According to the embodiment of the present invention, the fibrinogen detection sensor fabricated through the above method for preparing the fibrinogen detection sensor may include an electrode, and an erythrocyte membrane coating layer formed on the electrode and made of an erythrocyte membrane having a fibrinogen receptor.

Accordingly, the fibrinogen detection sensor may detect fibrinogen selectively binding to the fibrinogen receptor.

In addition, the fibrinogen detection sensor may provide a charge transfer resistance value that varies depending on a reaction of fibrinogen, in which the charge transfer resistance value may linearly vary depending on a fibrinogen concentration in a fibrinogen concentration range of 0.1 to 5000 μg/mL.

Accordingly, the fibrinogen detection sensor may have an advantage of being simple and efficient by predicting a concentration of fibrinogen simply through measurement of charge-transfer resistance values.

In addition, the fibrinogen detection sensor may be efficient by simply detecting both deficiency and excess of fibrinogen even without using a separate device for detecting deficiency or excess of fibrinogen.

According to a third embodiment of the present invention, a biohormone detection sensor may include a substrate and a detection probe having a metal nanoparticle deposited on the substrate, and an aptamer linked to the metal nanoparticle. Accordingly, the biohormone detection sensor according to the above embodiment may be configured to react with cortisol so as to easily sense the cortisol even from saliva, blood and the like. Furthermore, in the biohormone detection sensor according to the above embodiment, a size of the metal nanoparticle may be controlled to be 80 nm or more. Accordingly, cortisol sensing efficiency of the biohormone detection sensor may be improved.

DESCRIPTION OF DRAWINGS

FIG. 1 is a flowchart for explaining a method for fabricating a fibrinogen detection sensor according to a first embodiment of the present invention.

FIGS. 2A to 2D are views showing a process of fabricating a fibrinogen detection sensor according to a first embodiment of the present invention.

FIGS. 3A and 3B are enlarged views showing A and B of FIGS. 2B and 2C.

FIG. 4 is a sectional view showing T-T' of FIG. 2C.

FIG. 5 is a picture showing a substrate where gold particles are deposited according to a first embodiment of the present invention.

FIGS. 6A to 7B are pictures showing a fibrinogen detection sensor according to a first embodiment of the present invention.

FIGS. 8A and 8B are pictures and graphs showing property changes according to a deposition time of gold nanoparticles in a process of fabricating a fibrinogen detection sensor according to a first embodiment of the present invention.

FIGS. 9A to 9D are graphs showing a measured surface plasmon resonance signal of each step in a process of fabricating a fibrinogen detection sensor according to a first embodiment of the present invention.

FIGS. 10A to 12D are graphs showing a property of a fibrinogen detection sensor according to a first embodiment of the present invention.

FIG. 13 is a flowchart for explaining a method for fabricating a fibrinogen detection sensor according to a second embodiment of the present invention.

FIGS. 14 to 23 are views for explaining S140 of the present invention.

FIG. 24 is a flowchart for explaining a method for fabricating a biohormone detection sensor according to a third embodiment of the present invention.

FIG. 25 is a flowchart for explaining a step of preparing metal nanoparticles in a method for fabricating a biohormone detection sensor according to a third embodiment of the present invention.

FIG. 26 is a view showing a biohormone detection sensor according to a third embodiment of the present invention.

FIG. 27 is an enlarged view showing A of FIG. 26.

FIGS. 28A to 28D are general pictures showing a biohormone detection sensor according to a third embodiment of the present invention.

FIGS. 29A to 29D are optical pictures showing a biohormone detection sensor according to a third embodiment of the present invention.

FIGS. 30A to 30D are graphs showing a local surface plasmon resonance signal of a biohormone detection sensor according to a third embodiment of the present invention.

FIGS. 31A and 31B are graphs showing a performance and a selective binding of a biohormone detection sensor according to a third embodiment of the present invention.

FIGS. 32A and 32B are graphs showing a property of a biohormone detection sensor according to a third embodiment of the present invention.

MODE FOR INVENTION

Hereinafter, preferred embodiments of the present invention will be described in detail with reference to the accompanying drawings. However, the technical spirit of the present invention is not limited to the embodiments, but may be realized in different forms. The embodiments introduced herein are provided to sufficiently deliver the spirit of the present invention to those skilled in the art so that the disclosed contents may become thorough and complete.

When it is mentioned in the specification that one element is on another element, it means that the first element may be directly formed on the second element or a third element may be interposed between the first element and the second element. Further, in the drawings, the thicknesses of the membrane and areas are exaggerated for efficient description of the technical contents.

Further, in the various embodiments of the present specification, the terms such as first, second, and third are used to describe various elements, but the elements are not limited to the terms. The terms are used only to distinguish one element from another element. Accordingly, an element mentioned as a first element in one embodiment may be mentioned as a second element in another embodiment. The embodiments illustrated here include their complementary embodiments. Further, the term "and/or" in the specification is used to include at least one of the elements enumerated in the specification.

In the specification, the terms of a singular form may include plural forms unless otherwise specified. Further, the terms "including" and "having" are used to designate that the features, the numbers, the steps, the elements, or combinations thereof described in the specification are present, and are not to be understood as excluding the possibility that one or more other features, numbers, steps, elements, or combinations thereof may be present or added. In addition, the term "connection" used herein may include the meaning of indirectly connecting a plurality of components, and directly connecting a plurality of components.

Further, in the following description of the present invention, a detailed description of known functions or configurations incorporated herein will be omitted when it may make the subject matter of the present invention unnecessarily unclear.

The biomaterial detection sensor according to the first embodiment will be described with reference to FIGS. 1 to 12D, the biomaterial detection sensor according to the second embodiment will be described with reference to FIGS. 13 to 23, and the biomaterial detection sensor according to the third embodiment will be described with reference to FIGS. 24 to 32B.

In this case, the biomaterial detection sensor according to the first and second embodiments may be a sensor for detecting fibrinogen, and the biomaterial detection sensor according to the third embodiment may be a sensor for detecting bio-stress hormone.

Hereinafter, the biomaterial detection sensor according to the first and second embodiments will be called a fibrinogen detection sensor, and the biomaterial detection sensor according to the third embodiment will be called a bio-stress detection sensor.

FIG. 1 is a flowchart for explaining a method for fabricating a fibrinogen detection sensor according to the first embodiment of the present invention, FIGS. 2A to 2D are views showing a process of fabricating a fibrinogen detection sensor according to the first embodiment of the present invention, FIGS. 3A and 3B are enlarged views showing A and B of FIGS. 2B and 2C, and FIG. 4 is a sectional view showing T-T' of FIG. 2C.

Referring to FIG. 1, FIG. 2A, FIG. 2B, a substrate 100 and a metal nanoparticle 200 may be prepared (S100). According to one embodiment, the substrate 100 may be a glass substrate. For example, the substrate 100 may be a cover glass having a diameter of 12 mm. A type of the substrate 100 may be not limited.

The substrate 100 may be washed. For example, the substrate 100 may be washed in a piranha solution containing sulfuric acid ($H_2SO_4$) and hydrogen peroxide ($H_2O_2$) at a ratio of 3:1 for 30 minutes, washed with distilled water, reacted with 4% 3-aminopropyltrimethoxysilane (APTMS) for 30 minutes, and washed again with distilled water.

According to one embodiment, the preparing of the metal nanoparticle 200 may include preparing a surfactant and mixing the surfactant with a metal seed solution. For example, the surfactant may include trisodium citrate ($Na_3C_6H_6O_7$). For example, the metal seed solution may include hydrogen tetrachloroauric(III) acid ($HAuCl_4$). Accordingly, the metal nanoparticle 200 may include a gold (Au) nanoparticle. In addition, the metal nanoparticle 200 may be prepared as a type of AuNP solution.

More specifically, a trisodium citrate solution having a volume of 150 mL and a concentration of 2.2 rm may be heated up to a temperature of 100° C., after which hydrogen tetrachloroauric(III) acid having a volume of 1 mL and a concentration of 25 mM may be added into the heated trisodium citrate solution and subjected into a reaction, and then the reacted solution may be cooled down to a temperature of 90° C. In addition, hydrogen tetrachloroauric(III) acid having a volume of 1 mL and a concentration of 25 mM may be added into a solution at a lower temperature and subjected into a reaction for 30 minutes, after which hydrogen tetrachloroauric(III) acid having a volume of 1 mL and a concentration of 25 mM may be added once again and subjected into a reaction for 30 minutes, so as to prepare the metal nanoparticles 200.

After being prepared, the substrate 100 and the metal nanoparticles 200 may be subjected into a reaction, so that the metal nanoparticles 200 may be deposited on the substrate 100 (S200). For example, a solution containing the substrate 100 and the metal nanoparticles 200 may be reacted in a 24-well plate for one hour, so that the metal nanoparticles 200 may be deposited on the substrate 100. Accordingly, the metal nanoparticle 200 may be disposed on the substrate 100 as shown in FIG. 3A.

After that, an erythrocyte membrane (EM) may be extracted from an erythrocyte (S300). The extracting of the erythrocyte membrane (EM) (S300) may be performed apart from above S100 and above S200. In other words, the extracting of the erythrocyte membrane (EM) (S300) may be performed after above S100 and above S200, and may be performed even before above S100 and above S200.

According to one embodiment, the extracting of the erythrocyte membrane (EM) may include separating blood plasma from whole blood and crushing an erythrocyte in the plasma to remove cytoplasm therefrom. More specifically, plasma may be separated from the whole blood through centrifugation, after which hemolysis may be caused by using phosphate buffered saline (PBS) so as to crush the erythrocyte, and then the cytoplasm may be removed from the plasma having the erythrocyte crushed through centrifugation so as to extract the erythrocyte membrane (EM).

Referring to FIG. 1 and FIG. 2C, the erythrocyte membrane (EM) may be provided on the substrate 100 where the metal nanoparticle 200 is deposited after extracting the erythrocyte membrane (EM), so as to form a detection probe 300 on the substrate 100 (S400). For example, the substrate 100 where the metal nanoparticle 200 is deposited, and the erythrocyte membrane (EM) may be reacted in a 24-well plate for one hour, so as to form the detection probe 300.

Referring to FIG. 2D, the detection probe 300 may selectively react with fibrinogen (FB). In other words, if the detection probe (300) reacts with fibrinogen (FB) and a plurality of substances, the detection probe (300) may react with fibrinogen (FB), but may not react with other substances except fibrinogen (FB). For example, if the detection probe 300 reacts with fibrinogen (FB), human serum albumin (HSA) and y-globulin, the detection probe 300 may react with fibrinogen (FB), but may not react with HAS and y-globulin.

If the detection probe 300 selectively reacts with fibrinogen (FB), a local surface plasmon resonance signal of the substrate 100 may be changed. Accordingly, the fibrinogen detection sensor according to the above embodiment may be configured to sense fibrinogen (FB) by measuring a change in the local surface plasmon resonance signal. Specifically, after dropping 10 μL of fibrinogen into the fibrinogen detection sensor according to the above embodiment, fibrinogen (FB) may be sensed through a method of measuring a change in the local surface plasmon resonance signal by using a spectrometer and a light source.

According to one embodiment, the fibrinogen detection sensor according to the above embodiment may sense fibrinogen (FB) having a concentration of 0.001 mg/mL or more. In addition, the fibrinogen detection sensor according to the above embodiment may linearly sense fibrinogen (FB) in a concentration range of 0.001 to 10 mg/mL.

Referring to FIG. 2C, FIG. 3B, and FIG. 4, in the detection probe 300, the erythrocyte membrane (EM) may conformally cover the metal nanoparticle 200. According to one embodiment, the erythrocyte membrane (EM) may conformally cover both the substrate 100 and the metal nanoparticle 200. Accordingly, one region (EA1) of the erythrocyte membrane (EM) may be disposed to be spaced apart from the substrate 100 by a predetermined distance with the metal nanoparticle (200) interposed therebetween. In contrast, the other region (EA2) of the erythrocyte membrane (EM) may be disposed to come into direct contact with the substrate 100.

In this case, the metal nanoparticle 200 may be fixed on the substrate 100 by the erythrocyte membrane (EM). In addition, as the metal nanoparticle 200 is fixed on the substrate 100, even when the detection probe 300 reacts with fibrinogen (FB), the position of the metal nanoparticle 200 may not change, so as to enhance the accuracy of sensing fibrinogen (FB). In other words, among the plurality of detection probes 300, a distance (d) between first and second metal nanoparticles 200a and 200b adjacent to each other before reacting with fibrinogen (FB) is the same as a distance (d) between the first and second metal nanoparticles 200a and 200b after reacting with the fibrinogen (FB). Accordingly, a change in the local surface plasmon resonance signal of the substrate 100 may constantly occur, so as to enhance the sensing accuracy of the fibrinogen detection sensor according to the above embodiment.

In contrast, if the erythrocyte membrane (EM) fails to conformally cover the metal nanoparticles 200, or if the erythrocyte membrane (EM) fails to cover both the substrate 100 and the metal nanoparticle 200, the position of the metal nanoparticle 200 may not be fixed. In other words, the position of the metal nanoparticle 200 may be subject to change in a process where the detection probe 300 reacts with fibrinogen (FB). In this case, a change in the local surface plasmon resonance signal of the substrate 100 may become unstable, so as to cause a problem in that the sensing accuracy of the fibrinogen detection sensor is deteriorated.

According to one embodiment, a thickness of the erythrocyte membrane (EM) may be controlled to be 2 nm or less. For this purpose, a concentration of the erythrocyte membrane (EM) provided on the substrate 100 where the metal nanoparticle 200 is deposited may be controlled to be 0.05 v/v % in the forming of a detection probe (S400). As a thickness of the erythrocyte membrane (EM) is controlled to be 2 nmor less, the sensing efficiency of the fibrinogen detection sensor according to the above embodiment may be enhanced. In contrast, if a thickness of the erythrocyte membrane (EM) is more than 2 nm, a change in the local surface plasmon resonance signal may not easily occur, and thus the sensing efficiency of the fibrinogen detection sensor may be deteriorated.

The fibrinogen detection sensor according to the embodiment of the present invention may include the substrate 100 and the detection probe 300 including the metal nanoparticle 200 deposited on the substrate 100, and an erythrocyte membrane (EM) conformally covering the metal nanoparticle 200, in which the detection probe 300 may selectively react with fibrinogen (FB). In addition, a local surface plasmon resonance signal of the substrate 100 may vary if the detection probe 300 selectively reacts with the fibrinogen (FB). Accordingly, the fibrinogen detection sensor according to the above embodiment may detect fibrinogen with high sensitivity through a simple method for measuring a change in the local surface plasmon resonance signal without an additional marker.

The fibrinogen detection sensor and the method for fabricating the same according to an embodiment of the present invention have been described above. Hereinafter, specific experimental embodiments and the results of evaluating properties will be described with regard to the fibrinogen detection sensor according to an embodiment of the present invention and the method for fabricating the same.

Fabricating of Gold Nanoparticle According to an Embodiment

A trisodium citrate solution having a volume of 150 mL and a concentration of 2.2 mM was heated up to a temperature of 100° C., after which the heated solution was mixed with hydrogen tetrachloroauric (III) acid having a volume of 1 mL and a concentration of 25 mM and the mixed solution was cooled down to a temperature of 90° C.

Then, the resulting mixed solution was reacted with hydrogen tetrachloroauric(III) acid having a volume of 1 mL and a concentration of 25 mM for 30 minutes, after which the resulting mixture was reacted again with hydrogen tetrachloroauric(III) acid having a volume of 1 mL and a concentration of 25 mM for 30 minutes, so as to fabricate gold nanoparticles according to the above embodiment.

Preparing Erythrocyte Membrane According to an Embodiment

Plasma was separated from whole blood through centrifugation, after which hemolysis was caused by using phosphate buffered saline (PBS) so as to crush erythrocytes, and then cytoplasm was removed from the plasma having the erythrocytes crushed through centrifugation, so as to prepare an erythrocyte membrane (EM).

Fabricating of Fibrinogen Detection Sensor According to an Embodiment

A cover glass having a diameter of 12 mm may be prepared as a substrate. The prepared cover glass was washed in a piranha solution containing sulfuric acid and hydrogen peroxide at a ratio of 3:1 for 30 minutes, washed with distilled water, reacted with ethanol-based 4% 3-aminopropyltrimethoxysilane for 30 minutes, and washed again with distilled water.

The washed cover glass was heat-treated at a temperature of 60° C. for two hours, after which the heat-treated cover glass was reacted with gold nanoparticles according to the above embodiment in a 24-well plate for one hour, and thus the gold nanoparticles were deposited on the cover glass.

After that, the cover glass where the gold nanoparticles were deposited was reacted with the erythrocyte membrane according to the above embodiment in a 24-well plate for one hour, so as to fabricate a fibrinogen detection sensor according to the above embodiment.

FIG. 5 is a picture showing a substrate where gold particles are deposited according to a first embodiment of the present invention, and FIGS. 6A to 7B are pictures showing a fibrinogen detection sensor according to a first embodiment of the present invention.

Referring to FIG. 5, a substrate where gold nanoparticles are deposited according to the first embodiment was shown through scanning electron microscopy (SEM) photographing. Referring to FIG. 6A, a state in which fibrinogen is reacted to the fibrinogen detection sensor according to the above embodiment was shown through the SEM photographing. And, referring to FIG. 6B, the fibrinogen detection sensor according to the above embodiment was shown through the SEM photographing. As can be understood from FIGS. 5 to 6B, it might be confirmed for the fibrinogen detection sensor according to the above embodiment that gold nanoparticles are disposed on the substrate and the erythrocyte membrane covers the substrate and the gold nanoparticles. In addition, it might be confirmed that fibrinogen adheres to the gold nanoparticle covered with the erythrocyte membrane when reacting with fibrinogen.

Referring to FIG. 7A, the substrate where gold nanoparticles are deposited according to the first embodiment was shown through atomic force microscope (AFM) photographing. Referring to FIG. 7B, the fibrinogen detection sensor according to the first embodiment was shown through the AFM photographing. When comparing FIGS. 7A and 7B, it might be confirmed that an overall height is increased. In other words, it might be confirmed that the erythrocyte membrane covers the gold nanoparticles, and thus an overall height is increased.

FIGS. 8A and 8B are pictures and graphs showing property changes according to a deposition time of gold nanoparticles in a process of fabricating a fibrinogen detection sensor according to a first embodiment of the present invention.

Referring to FIG. 8A, in a process of fabricating the fibrinogen detection sensor according to the first embodiment, a time in which the gold nanoparticles react with the substrate was controlled to be 30 minutes (30 min), 1 hour (1 h), and 2 hours (2 h), and each case is shown through general photographing. Referring to FIG. 8B, in a process of fabricating the fibrinogen detection sensor according to the above embodiment, a time in which the gold nanoparticles react with the substrate was controlled to be 30 minutes (30 min), 1 hour (1 h), and 2 hours (2 h), and a local surface plasmon resonance signal of the fibrinogen detection sensor fabricated under each of the above conditions was measured and shown.

As can be understood from FIGS. 8A and 8B, it might be confirmed that, when the substrate and the gold nanoparticles are reacted for 30 minutes, the gold nanoparticles are not easily deposited on the substrate and a change in the local surface plasmon resonance signal also slightly occurs. In addition, it might be confirmed that, when the substrate and the gold nanoparticles are reacted for two hours, the gold nanoparticles are easily deposited on the substrate, but an amount of deposition is too large to make a clear change in the local surface plasmon resonance signal. In contrast, it might be confirmed that, when the substrate and the gold nanoparticles are reacted for one hour, the gold nanoparticles are easily deposited on the substrate, and a change in the local surface plasmon resonance signal also clearly occurs.

FIGS. 9A to 9D are graphs showing a measured surface plasmon resonance signal of each step in a process of fabricating a fibrinogen detection sensor according to a first embodiment of the present invention.

Referring to FIGS. 9A to 9D, a surface plasmon resonance signal was represented by measuring the surface plasmon resonance signal with respect to a substrate used in a process of fabricating the fibrinogen detection sensor according to the first embodiment, a substrate provided with gold nanoparticles, a substrate provided with gold nanoparticles covered with an erythrocyte membrane, and a substrate provided with gold nanoparticles covered with an erythrocyte membrane reacted with fibrinogen, respectively. As can be understood from FIGS. 9A to 9D, it might be confirmed for the fibrinogen detection sensor according to the above embodiment that the surface plasmon resonance signal varies as the sensor reacts with fibrinogen.

FIGS. 10A to 12D are graphs showing a property of a fibrinogen detection sensor according to a first embodiment of the present invention.

Referring to FIG. 10A, in a process of fabricating the fibrinogen detection sensor according to the first embodiment, the concentration of the erythrocyte membrane reacting with the substrate where gold nanoparticles are deposited was controlled to be 10 v/v %, 0.5 v/v %, and 0.05 v/v %, and an amount of change in the surface plasmon resonance signal ($\Delta\lambda_{max}$, nm) was measured and shown with regard to the fibrinogen detection sensor fabricated under each of the conditions.

As can be understood from FIG. 10A, it might be confirmed that the fibrinogen detection sensor fabricated by reacting an erythrocyte membrane having a concentration of 0.05 v/v % with a substrate where gold nanoparticles are deposited shows a significantly high change in the plasmon resonance signal in comparison with the fibrinogen detection sensor fabricated by reacting an erythrocyte membrane having a concentration of 10 v/v % and 0.5 v/v % with a substrate where gold nanoparticles are deposited.

Referring to (b) of FIG. 10, an amount of change in the surface plasmon resonance signal ($\Delta\lambda_{max}$, nm) was measured and shown with regard to the fibrinogen detection sensor according to the first embodiment after reacting with fibrinogen having a concentration of 10, 1, 0.1, 0.01, and 0.001 mg/ml, respectively.

As can be understood from FIG. 10B, it might be confirmed for the fibrinogen detection sensor according to the first embodiment that an amount of change in the surface plasmon resonance signal is also linearly decreased as the concentration of the reacted fibrinogen is lowered to 10, 1, 0.1, 0.01, and 0.001 mg/ml.

Referring to FIG. 11A, an amount of change in the surface plasmon resonance signal ($\Delta\lambda_{max}$, %) was measured and shown with the fibrinogen detection sensor according to the first embodiment after reacting with fibrinogen, human serum albumin (HSA), and y-globulin, respectively. As can be understood from FIG. 11A, it might be confirmed that the fibrinogen detection sensor according to the first embodiment shows a remarkable amount of change in the surface plasmon resonance signal when reacting with fibrinogen, but shows almost no change in the surface plasmon resonance signal when reacting with human serum albumin (HSA) and y-globulin. Accordingly, it may be understood that the fibrinogen detection sensor according to the first embodiment selectively reacts with fibrinogen.

Referring to (b) of FIG. 11, an amount of change in the surface plasmon resonance signal ($\Delta\lambda_{max}$, nm) was measured and shown with regard to the fibrinogen detection sensor according to the first embodiment after reacting with fibrinogen having each of different concentrations, respectively. As can be understood from FIG. 11B, it might be confirmed that the fibrinogen detection sensor according to the first embodiment may sense fibrinogen in a wide concentration range of 0.001 to 10 mg/mL.

FIGS. 12A to 12D are graphs showing a specific property of a fibrinogen detection sensor according to a first embodiment of the present invention depending on the presence of an erythrocyte membrane.

Referring to FIG. 12A, each height was measured and shown with regard to an AuNP substrate where gold nanoparticles according to the first embodiment are deposited on the substrate and an EM-AuNP substrate where an erythrocyte membrane covers a substrate where gold nanoparticles are deposited. As can be understood from FIG. 12A, it might be confirmed that the height is high with regard to the EM-AuNP substrate where an erythrocyte membrane covers the substrate where gold nanoparticles are deposited in comparison with the AuNP substrate where gold nanoparticles are deposited on the substrate.

Referring to FIG. 12B, FT-IR spectra were shown with regard to each of an amine substrate where an amine group is deposited, an AuNP substrate where an erythrocyte membrane and gold nanoparticles are deposited, and an EM-AuNP substrate where gold nanoparticles are deposited and covered with an erythrocyte membrane. As can be understood from FIG. 12B, it might be confirmed that the EM-AuNP substrate where gold nanoparticles are deposited and covered with an erythrocyte membrane shows a highest transmittance (a.u.) depending on a wavenumber ($cm^{-1}$).

Referring to FIGS. 12C and 12D, a surface plasmon resonance signal was measured for each of the AuNP substrate where gold nanoparticles according to the first embodiment are deposited on the substrate and the EM-AuNP substrate where an erythrocyte membrane covers the substrate where gold nanoparticles are deposited. As can be understood from FIGS. 12C and 12D, it might be confirmed that the EM-AuNP substrate where an erythrocyte membrane covers the substrate where gold nanoparticles are deposited shows a clear surface plasmon resonance signal in comparison with the AuNP substrate where gold nanoparticles are deposited on the substrate.

As can be understood from FIGS. 10A to 12D, it might be confirmed that the detection sensor including a substrate and a detection probe having a metal nanoparticle deposited on the substrate, and an erythrocyte membrane conformally covering the metal nanoparticle may selectively react with fibrinogen to show a change in the surface plasmon resonance signal, thereby detect fibrinogen through a simple method of measuring the change.

The first embodiment has been described above. Hereinafter, the second embodiment will be described with reference to FIGS. 13 to 23.

FIG. 13 is a flowchart for explaining a method for fabricating a fibrinogen detection sensor according to a second embodiment of the present invention, and FIGS. 14 to 23 are views for explaining S140 of the present invention.

Referring to FIG. 14, the method for fabricating the fibrinogen detection sensor may include: extracting an erythrocyte (S110); crushing the erythrocyte (S120); separating an erythrocyte membrane (S130); and forming an erythrocyte membrane coating layer (S140). Hereinafter, each of the steps will be described in detail.

Step S110

An erythrocyte may be extracted in S110.

Specifically, the erythrocyte may be extracted from blood.

According to one embodiment, the blood may be centrifuged to extract the erythrocyte from the blood. For example, 1,000 g of the blood may be centrifuged at 4° C. for five minutes.

Accordingly, the erythrocyte and plasma were separated from the blood so as to extract the erythrocyte.

According to one embodiment, the extracted erythrocyte may be washed before performing a subsequent step (S120). For example, the erythrocyte may be washed at 4° C. with phosphate buffer saline (1×PBS, pH 7.4, Gibco) three times.

Step S120

In S120, the extracted erythrocyte may be crushed.

Specifically, the erythrocyte may be crushed and subjected into hemolysis. For example, the erythrocyte may be subjected into hemolysis at 4° C. with 0.25×PBS for 20 minutes. Accordingly, hemoglobin, peripheral membrane protein, etc., may be released from the erythrocyte.

Step S130

In S130, an erythrocyte membrane may be separated from the crushed erythrocyte.

According to one embodiment, the crushed erythrocyte may be centrifuged to separate hemoglobin, peripheral membrane protein, etc., released from the erythrocyte membrane and the crushed erythrocyte. For example, the crushed erythrocyte may be centrifuged for five minutes.

Accordingly, it may be possible to separate hemoglobin, peripheral membrane proteins, etc., released from the erythrocyte membrane and the crushed erythrocyte.

According to one embodiment, the separated erythrocyte membrane may be washed before performing a subsequent step (S140). For example, the erythrocyte membrane may be washed twice at 4° C. with 1×PBS.

Step S140

In S140, an erythrocyte membrane coating layer 200 may be formed on an electrode 100.

Specifically, prior to forming the erythrocyte membrane coating layer 200, the electrode 100 may be prepared as shown in FIGS. 14 and 15A. For example, the electrode 100 may be made of gold (Au). More specifically, for example, the electrode 100 may be formed of circular gold having a diameter of 0.18 cm and an area of 0.03 $cm^2$.

Referring to FIG. 15A, the electrode 100 may be a working electrode WE. In other words, the fibrinogen detection sensor according to an embodiment of the present invention may include a working electrode WE, a counter electrode CE, and a reference electrode RE as components, in which the electrode 100 may be the working electrode WE.

Meanwhile, referring to FIG. 15B, when the electrode 100 is gold, it can be confirmed that a charge transfer resistance (Rct) corresponding to a Nyquist Plot semicircle of the electrode 100 is low.

According to one embodiment, the prepared electrode 100 may be washed before forming the erythrocyte membrane coating layer 200. For example, the electrode 100 may be washed with a 0.5 M $H_2SO_4$ solution.

Accordingly, a surface of the electrode 100 on which the erythrocyte membrane coating layer 200 is to be formed may be not only washed, but also activated.

After that, referring to FIGS. 16 and 17A, the erythrocyte membrane separated in S130 may be provided on the washed electrode 100. Accordingly, the erythrocyte membrane coating layer 200 may be formed on the electrode 100.

Specifically, the erythrocyte membrane may be provided on the electrode 100, and then maintained at a predetermined temperature for a predetermined time, in order to form the erythrocyte membrane coating layer 200 on the electrode 100.

For example, referring to FIG. 18, the erythrocyte membrane may be provided on the electrode 100 and maintained at 50° C. for 20 minutes or more.

In the graph shown in FIG. 18, an increase in the charge transfer resistance (Rct) value for a period of less than 20 minutes may mean that the erythrocyte membrane is being deposited on the electrode 100.

Meanwhile, a non-increase in the charge transfer resistance value for a period of time after 20 minutes may mean that the erythrocyte membrane is completely deposited on the electrode 100 and thus the erythrocyte membrane coating layer 200 is formed.

Thus, unlike the embodiment of the present invention, if the erythrocyte membrane is provided on the electrode 100 and maintained at 50° C. for less than 20 minutes, it may be difficult to form the erythrocyte membrane coating layer 200 on the electrode 100 from the provided erythrocyte membrane. Alternatively, it may be difficult to form the erythrocyte membrane coating layer 200 completely covering one surface of the electrode 100 from the provided erythrocyte membrane.

This may be probably because the above-described period of less than 20 minutes is insufficient to form the erythrocyte membrane coating layer 200 by providing the erythrocyte membrane on the electrode 100.

However, according to the embodiment of the present invention, the erythrocyte membrane coating layer 20 completely covering one surface of the electrode 10 may be formed by providing the erythrocyte membrane on the electrode 100 and maintaining for 20 minutes or longer.

According to one embodiment, the erythrocyte membrane coating layer 200 formed on the electrode 100 may be a single erythrocyte membrane.

This may be probably because the erythrocyte membrane has a property of being deposited as a single layer. Accordingly, the erythrocyte membrane coating layer 200 may be stopped from being formed, after the erythrocyte membrane coating layer 200 is formed on the electrode 100 as a single erythrocyte membrane.

Meanwhile, referring to FIG. 17B, it can be confirmed that, as the erythrocyte membrane coating layer 200 is formed on the electrode 100, the charge transfer resistance corresponding to the Nyquist flat semicircle of the electrode 100 on which the erythrocyte membrane coating layer 200 is formed is increased slightly more than that of the electrode 100 described above with reference to FIG. 15B.

As a result, it can be understood from the slight increase in the charge transfer resistance that the erythrocyte membrane coating layer 200 is formed on the electrode 100.

As described above, the erythrocyte membrane coating layer 200 was formed on the electrode 100, and thus the charge transfer resistance was slightly increased, but the slight increase in the charge transfer resistance may be at a level in which charge transfer is easily performed through the erythrocyte membrane coating layer 200. Thus, the fibrinogen detection sensor 1000 according to one embodiment including the erythrocyte membrane coating layer 200 formed on the electrode 100 may easily detect fibrinogen (F).

According to one embodiment, the erythrocyte membrane coating layer 200 may be washed and dried after being formed on the electrode 100. For example, the erythrocyte membrane coating layer 200 may be formed on the electrode 100, then washed with distilled water, and then dried in a pure air atmosphere.

Accordingly, the erythrocyte membrane coating layer 200 may be formed on the electrode 100, and thus the fibrinogen detection sensor 1000 according to one embodiment may be fabricated.

The erythrocyte membrane coating layer 200 of the fibrinogen detection sensor 1000 may have a fibrinogen receptor 210 as shown in FIGS. 19 and 20A.

Accordingly, the fibrinogen detection sensor 1000 may selectively detect fibrinogen (F) by the fibrinogen receptor 210 of the erythrocyte membrane coating layer 200.

Meanwhile, referring to FIG. 20B, if fibrinogen (F) is provided to the fibrinogen detection sensor 1000, the fibrinogen receptor 210 of the fibrinogen detection sensor 1000 binds with the fibrinogen (F), and thus it can be confirmed that the charge transfer resistance corresponding to the Nyquist flat semicircle of the fibrinogen detection sensor 1000 is increased greatly more than before binding with the fibrinogen (F) described with reference to FIGS. 15B and 17B.

Accordingly, it can be understood that the fibrinogen detection sensor 1000 may easily detect the fibrinogen (F) by using an increase in the charge transfer resistance described above.

According to one embodiment, the fibrinogen detection sensor 1000 may provide a charge transfer resistance value that varies depending on a reaction between the fibrinogen receptor 210 and the fibrinogen (F). In other words, the fibrinogen receptor 210 of the fibrinogen detection sensor 1000 may provide a charge transfer resistance value that varies depending on a concentration of the fibrinogen (F).

Specifically, referring to FIG. 21A, it can be confirmed that the Nyquist flat semicircle of the fibrinogen detection sensor 1000 increases as a concentration of the fibrinogen (F) increases in the fibrinogen (F) concentration range of 0.0001 to 5 mg/mL.

In addition, referring to FIG. 21B, it can be confirmed that a charge transfer resistance value of the fibrinogen detection sensor 1000 linearly varies depending on the fibrinogen (F) concentration in the fibrinogen (F) concentration range of 0.0001 to 5 mg/mL.

Accordingly, the fibrinogen detection sensor 1000 may easily predict the concentration of fibrinogen (F) simply by measuring the charge transfer resistance value, considering that the charge transfer resistance value linearly varies depending on the concentration of fibrinogen (F).

Meanwhile, referring to FIG. 22, it is possible to confirm the ability of the fibrinogen detection sensor 1000 to detect fibrinogen (F) in an actual environment, that is, in serum.

In the actual environment, it can be confirmed that the charge transfer resistance value of the fibrinogen detection sensor 1000 linearly varies depending on the fibrinogen (F) concentration in the fibrinogen (F) concentration range of 0.001 to 5 mg/mL.

The above range is slightly smaller than the fibrinogen (F) concentration range of 0.0001 to 5 mg/mL described above with reference to FIG. 21B. The above result may be caused by other proteins present in the serum.

Thus, it can be understood that the fibrinogen detection sensor 1000 may predict the fibrinogen (F) concentration in an actual environment through the charge transfer resistance value that linearly varies depending on the fibrinogen (F) concentration in the fibrinogen (F) concentration range of 0.001 to 5 mg/mL.

According to one embodiment, the fibrinogen (F) concentration range of 0.0001 to 5 mg/mL described above with reference to FIG. 21B may be a range including deficiency and excess of fibrinogen (F). In other words, it means that the fibrinogen detection sensor 1000 according to an embodiment of the present invention may detect both a deficiency and an excess of fibrinogen (F).

In contrast, referring to <Table 1> below, unlike the embodiment of the present invention, fibrinogen detection sensors according to conventional comparative examples may detect only the deficiency or only the excess of fibrinogen (F).

TABLE 1

|  | Fibrinogen detector | Detection limit (µg/mL) | Detection range (µg/mL) |
|---|---|---|---|
| Embodiment | Erythrocyte membrane | 0.049 | 0.1 to 5000 |
| Comparative Example 1 | Antibody immobilized gold electrode | 500 | 500 to 4500 |
| Comparative Example 2 | Hemin | 0.00024 | 0.002 to 0.034 |
| Comparative Example 3 | IgM | 500 | 500 to 2500 |
| Comparative Example 4 | COOH-magnetic beads | 0.044 | 0.15 to 6.18 |
| Comparative Example 5 | SNP-antibody | 0.024 | 0.067 to 1.67 |
| Comparative Example 6 | GNP-antibody | 0.001 | 0.027 to 1.07 |

In other words, the fibrinogen detection sensor 1000 according to an embodiment of the present invention may be efficient by simply detecting both the deficiency and the excess of fibrinogen (F) without using a separate device for detecting the deficiency or the excess of fibrinogen (F).

Meanwhile, referring to <Table 1>, it can be confirmed that the fibrinogen detection sensor 1000 detects a change in the charge transfer resistance at a fibrinogen (F) concentration of 0.049 µg/mL or more.

Referring to FIG. 23, the fibrinogen detection sensor 1000 may be inhibited from non-specifically binding to proteins other than fibrinogen (F). Specifically, the fibrinogen detection sensor 1000 may be inhibited from non-specifically binding to proteins other than fibrinogen (F) through selective binding of the fibrinogen receptor 210 to fibrinogen (F).

Accordingly, as shown in FIG. 23, it can be confirmed that the fibrinogen detection sensor 1000 (w/EM) selectively binds with fibrinogen (F) by including the erythrocyte membrane coating layer 200, and thus is inhibited from binding with proteins other than fibrinogen (F), for example, y-globulin and human serum albumin (HSA).

Thus, it can be confirmed that the ability of the fibrinogen detection sensor 1000 (w/EM) including the erythrocyte membrane coating layer 200 to detect fibrinogen (F) is increased compared to the fibrinogen detection sensor (w/o EM) not including the erythrocyte membrane coating layer 200 as shown in FIG. 23.

The method for fabricating the fibrinogen detection sensor 1000 according to the second embodiment of the present invention has been described above.

The method for fabricating the fibrinogen detection sensor 1000 may include: extracting an erythrocyte from blood (S110); crushing the extracted erythrocyte (S120); separating an erythrocyte membrane from the crushed erythrocyte (S130); and providing the erythrocyte membrane on an electrode so as to form an erythrocyte membrane coating layer 200 having a fibrinogen receptor 210 (S140).

The fibrinogen detection sensor 1000 according to an embodiment of the present invention fabricated by the method for fabricating the fibrinogen detection sensor 1000 may include an electrode 100 and an erythrocyte membrane coating layer 200 formed on the electrode 100 and made of an erythrocyte membrane having a fibrinogen receptor 210.

Accordingly, the fibrinogen detection sensor 1000 may detect fibrinogen (F) selectively binding to the fibrinogen receptor 210.

In addition, the fibrinogen detection sensor 1000 may provide a charge transfer resistance value that varies depending on a reaction of fibrinogen (F), in which the charge transfer resistance value may linearly vary depending on a fibrinogen (F) concentration in a fibrinogen (F) concentration range of 0.1 to 5000 µg/mL.

Accordingly, the fibrinogen detection sensor 1000 has an advantage of being simple and efficient by predicting a concentration of fibrinogen (F) simply through measurement of charge-transfer resistance values.

In addition, the fibrinogen detection sensor 1000 may be efficient by simply detecting both the deficiency and the excess of fibrinogen (F) without using a separate device for detecting the deficiency or the excess of fibrinogen (F).

The second embodiment has been described above. Hereinafter, a third embodiment of the present invention will be described with reference to FIGS. 24 to 32B.

FIG. 24 is a flowchart for explaining a method for fabricating a biohormone detection sensor according to a third embodiment of the present invention, FIG. 25 is a flowchart for explaining a step of preparing metal nanoparticles in a method for fabricating a biohormone detection sensor according to a third embodiment of the present invention, FIG. 26 is a view showing a biohormone detection sensor according to a third embodiment of the present invention, and FIG. 27 is an enlarged view showing A of FIG. 26.

Referring to FIGS. 24 to 27, a substrate 110 may be prepared (S100). According to one embodiment, the substrate 110 may be a glass substrate. For example, the substrate 110 may be a cover glass having a diameter of 12 mm. A type of the substrate 110 may be not limited.

A metal nanoparticle 122 having a size controlled may be prepared (S200). For example, the metal nanoparticle 122 may include a gold (Au) nanoparticle. According to one embodiment, the preparing of the metal nanoparticle 122 having a size controlled may include preparing a metal seed solution (S210); reacting the metal seed solution with a metal seed material (S220); extracting a predetermined amount from a solution in which the metal seed solution is reacted with the metal seed material (S230); and mixing the extracted solution with a surfactant so as to fabricate a metal nanoparticle (S240). For example, the metal seed material may include hydrogen tetrachloroauric(II) acid ($HAuCl_4$). For example, the surfactant may include trisodium citrate ($Na_3C_6H_5O_7$).

More specifically, the preparing of the metal seed solution (S210) may be performed through a method of heating a trisodium citrate solution having a volume of 150 mL and a concentration of 2.2 mM up to a temperature of 100° C., then mixing the heated solution with hydrogen tetrachloroauric(III) acid having a volume of 1 mL and a concentration of 25 mM, and then cooling the mixed solution down to a temperature of 90° C. The reacting of the metal seed solution with the metal seed material (S220) may be performed through a method of reacting the metal seed solution prepared in above S210 with hydrogen tetrachloroauric (III) acid having a volume of 1 mL and a concentration of 25 mM. The extracting of a predetermined amount from the solution in which the metal seed solution is reacted with the metal seed material (S230) may be performed through a method of extracting the solution reacted in above S220 in a volume of 55 mL. The preparing of the metal nanoparticle 122 by mixing the extracted solution with the surfactant (S240) may be performed through a method of mixing the solution extracted in above S230 with a trisodium citrate solution having a volume of 2 mL and a concentration of 60 mM and tertiary distilled water having a volume of 53 mL.

According to one embodiment, the reacting of the metal seed solution with the metal seed material (S220), the extracting (S230), and the mixing with the surfactant (S240) may be formed as a unit process. The unit process may be performed a plurality of times. According to one embodiment, as the number of repeating the unit process increases, a size of the metal nanoparticle 122 may increase. Accordingly, the metal nanoparticle 122 having a size controlled may be prepared.

After being prepared, the substrate 110 and the metal nanoparticle 122 may be subjected into a reaction, so that the metal nanoparticle 122 may be deposited on the substrate 110 (S300). For example, the substrate 100 and the metal nanoparticle 122 may be reacted for one hour.

An aptamer 124 may be provided on the substrate 100 where the metal nanoparticle 200 is deposited so as to form a detection probe 120 in which the metal nanoparticle 122 on the substrate 110 is linked to the aptamer 124 (S400). Specifically, it may be performed through a method of providing an aptamer having a volume of 1 mL and a concentration of 100 nM based on a Tris-EDTA buffer solution on the substrate 110 where the metal nanoparticle 122 is deposited. In addition, a size of the aptamer 124 linked to the metal nanoparticle 122 may be 85 mer.

Accordingly, the biohormone detection sensor 100 according to the third embodiment may be fabricated. In other words, the biohormone detection sensor 100 according to the third embodiment may include the substrate 110 and the detection probe 120 provided on the substrate 110, in which the detection probe 120 may include the metal nanoparticle 122 and the aptamer 124 linked to the metal nanoparticle 122.

The biohormone detection sensor 100 according to the third embodiment may selectively react with cortisol. Specifically, the detection probe 120 included in the biohormone detection sensor 100 may selectively react with cortisol. In other words, when a plurality of substances including cortisol are mixed, the biohormone detection sensor 100 may not react with the plurality of substances, but may react with cortisol only. Accordingly, the biohormone detection sensor 100 can easily detect cortisol from a biomaterial containing biohormone, such as saliva or blood.

According to one embodiment, when the detection probe 120 selectively reacts with cortisol, a local surface plasmon resonance signal of the substrate 110 may be changed. Accordingly, the biohormone detection sensor 100 according to the above embodiment may sense cortisol by measuring a change in the local surface plasmon resonance signal.

According to one embodiment, in the biohormone detection sensor 100, a plurality of detection probes 120 may be disposed on the substrate 110, in which the plurality of detection probes 120 may be spaced apart from each other as shown in FIG. 27. For this purpose, a size of the metal nanoparticle 122 may be 80 nm or more. More specifically, as described above, when a size of the aptamer 124 linked to the metal nanoparticle 122 is 85 mer, a size of the metal nanoparticle 122 may be controlled to be 80 nm or more, and thus the plurality of detection probes 120 disposed on the substrate 110 may be spaced apart from each other. In addition, the biohormone detection sensor 100 may have cortisol sensing efficiency improved as the plurality of detection probes 120 are disposed to be spaced apart from each other. Specifically, the biohormone detection sensor 100 may sense cortisol even at a concentration of 1 nM.

In contrast, when a size of the metal nanoparticles 122 is less than 80 nm, a phenomenon in which the plurality of detection probes 120 are aggregated may occur. Specifically, when a size of the metal nanoparticle 122 is less than 80 nm, the aptamers 124 of the detection probes 120 adjacent to each other may be linked to each other, and thus the detection probes 120 adjacent to each other may be aggregated. When the plurality of detection probes 120 are aggregated, there may be a problem in that cortisol sensing efficiency is deteriorated.

According to the third embodiment of the present invention, the biohormone detection sensor 100 may include the substrate 110 and the detection probe 120 including the metal nanoparticle 122 deposited on the substrate 110, and the aptamer 124 linked to the metal nanoparticle 122. Accordingly, the biohormone detection sensor 100 according to the above embodiment may easily sense cortisol even in saliva, blood and the like as the detection probe 120 selectively reacts with cortisol. In addition, in the biohormone detection sensor 100 according to the above embodiment, a size of the metal nanoparticle 122 may be controlled to be 80 nm or more. Accordingly, cortisol sensing efficiency of the biohormone detection sensor 100 may be improved.

The biohormone detection sensor according to the third embodiment of the present invention and the method for fabricating the same have been described above. Hereinafter, specific experimental embodiments and the results of evaluating properties will be described with regard to the biohormone detection sensor according to the third embodiment of the present invention and the method for fabricating the same.

Fabricating of Gold Nanoparticle According to an Embodiment

A trisodium citrate solution having a volume of 150 mL and a concentration of 2.2 mM was heated up to a temperature of 100° C., after which the heated solution was mixed with hydrogen tetrachloroauric(III) acid having a volume of 1 mL and a concentration of 25 mM and the mixed solution was cooled down to a temperature of 90° C., so as to prepare a gold seed solution.

The prepared gold seed solution was reacted with hydrogen tetrachloroauric(III) acid having a volume of 1 mL and a concentration of 25 mM, so as to extract the reacted solution in a volume of 55 mL. After that, the extracted solution was mixed with trisodium citrate solution having a volume of 2 mL and a concentration of 60 mM and tertiary distilled water having a volume of 53 mL so as to prepare gold nanoparticles according to the embodiment, in which reacting a gold seed solution and hydrogen tetrachloroauric (III) acid, extracting, and reacting with trisodium citrate solution were performed as a unit process while varying the number of repeating the unit process, so as to prepare a gold nanoparticle according to Example 1 having a size of 20 nm, a gold nanoparticle according to Example 2 having a size of 40 nm, a gold nanoparticle according to Example 3 having a size of 60 nm, and a gold nanoparticle according to Example 4 having a size of 80 nm.

Preparing a Biohormone Detection Sensor According to an Embodiment

A cover glass having a diameter of 12 nm was provided. The prepared cover glass was washed in a piranha solution containing sulfuric acid and hydrogen peroxide at a ratio of 3:1 for 30 minutes, washed with distilled water, reacted with ethanol-based 4% 3-aminopropyltrimethoxysilane for 30 minutes, and washed again with distilled water.

The washed cover glass was heat-treated at a temperature of 60° C. for two hours, after which the heat-treated cover glass was reacted with gold nanoparticles according to above Examples 1 to 4 in a 24-well plate for one hour, and thus the gold nanoparticles according to above Examples 1 to 4 were deposited on the cover glass, respectively.

After that, each of the cover glasses where gold nanoparticles according to above Examples 1 to 4 are deposited was reacted with 1 mL of 100 nM aptamer based on a Tris-EDTA buffer solution for six hours, and thus each of gold nanoparticles according to above Examples 1 to 4 was linked to the aptamer. Accordingly, the biohormone detection sensors according to above Examples 1 to 4 provided with detection probes including gold nanoparticles according to above Examples 1 to 4 and the aptamer on the cover glass were prepared.

FIGS. 28A to 28D are general pictures showing a biohormone detection sensor according to a third embodiment of the present invention, and FIGS. 29A to 29D are optical pictures showing a biohormone detection sensor according to a third embodiment of the present invention.

Referring to FIGS. 28A to 28D, the biohormone detection sensors according to above Examples 1 to 4 were shown through general photographing. As can be understood from FIGS. 28A to 28D, it might be confirmed that the biohormone detection sensor according to the above embodiment shows a deeper color as a size of the gold nanoparticles disposed on the cover glass increases. This may be determined as a phenomenon that occurs since the absorption wavelength becomes larger as the size of the gold nanoparticle increases.

Referring to FIGS. 29A to 29D, the biohormone detection sensors according to above Examples 1 to 4 were shown through scanning electron microscope (SEM) photographing. As can be understood from FIGS. 28A to 28D, it might be confirmed for the biohormone detection sensor according to the above embodiment that the number of particles disposed in the same area decreases as the size of the gold nanoparticle increases.

FIGS. 30A to 30D are graphs showing a local surface plasmon resonance signal of a biohormone detection sensor according to embodiments of the present invention.

Referring to FIGS. 30A to 30D, absorbance (a.u.) according to wavelength (nm) was shown for each of the case where gold nanoparticles are deposited on the cover glass according to above Examples 1 to 4 (AuNP 20 nm, 40 nm, 60 nm, 80 nm), and the biohormone detection sensors (aptamer) according to above Examples 1 to 4.

As can be understood from FIGS. 30A to 30D, in the case of the cover glass where the gold nanoparticles according to above Examples 1 to 4 are deposited, it might be confirmed that a peak value of the spectrum is red shifted to the right at the x-axis wavelength and also rises upward at the y-axis absorbance as the size of the deposited gold nanoparticles increases.

In addition, as can be understood from FIG. 30A, in the case of the biohormone detection sensor according to above Example 1, it might be confirmed that a signal increases at a wavelength of 600 nm compared to the cover glass where the gold nanoparticles according to above Example 1 are deposited. As can be understood from FIG. 30B, in the case of the biohormone detection sensor according to above Example 2, it might be confirmed that a signal increases at a wavelength of 680 nm compared to the cover glass where the gold nanoparticles according to above Example 2 are deposited. As can be understood from FIG. 30C, in the case of the biohormone detection sensor according to above Example 3, it might be confirmed that a signal increases at a wavelength of 750 nm compared to the cover glass where the gold nanoparticles according to above Example 1 are deposited. In contrast, as can be understood from FIG. 30D, in the case of the biohormone detection sensor according to above Example 4, it might be confirmed that there is no section where a signal increases compared to the cover glass where the gold nanoparticles according to Example 4 are deposited.

When the wavelength of the biohormone detection sensor according to the above embodiment is compared with the wavelength of the cover glass where the gold nanoparticles according to above embodiment are deposited, it can be determined that a section where a signal increases is shown as the plurality of detection probes are aggregated. Accordingly, in the case of the biohormone detection sensors according to above Examples 1 to 3, it may be determined that an aggregation phenomenon occurs among the plurality of detection probes. As a result, in the case of fabricating the biohormone detection sensor according to the above embodiment, it may be understood that the size of the gold nanoparticles needs to be controlled to be 80 nm or more in order to prevent an agglomeration phenomenon from occurring among a plurality of detection probes.

FIGS. 31A and 31B are graphs showing a performance and a selective binding of a biohormone detection sensor according to an embodiment of the present invention.

Referring to FIG. 31A, the biohormone detection sensor according to above Example 4 was reacted with cortisols having different concentrations (nM), after which $\Delta\lambda_{max}$ (nm) according to cortisol concentrations was measured and shown. As can be understood from FIG. 31A, it might be confirmed that the biohormone detection sensor according to above Example 4 may detect cortisol in a wide range of 0.1 nm to 1000 nM.

Referring to FIG. 31B, the biohormone detection sensor according to above Example 4 was reacted with cortisol, cortisone (CS), corticosterone (CC), progesterone (Prog), triamcinolone (TA), respectively, after which Relative $\Delta\lambda_{max}$ (%) was measured and shown. As can be understood from FIG. 8B, it might be confirmed that the biohormone detection sensor according to above Example 4 may selectively react with cortisol.

FIGS. 32A and 32B are graphs showing a property of a biohormone detection sensor according to an embodiment of the present invention.

Referring to FIG. 32A, the biohormone detection sensor according to above Example 4 was reacted with a reaction solution having a cortisol concentration of 100 nM, 10 nM, 1 nM, 0.1 nM, and 0 nM, after which Relative $\Delta\lambda_{max}$ (%) was measured and shown. The reaction solution was prepared by diluting a person's saliva with phosphate buffer saline (PBS) to make a solution having a saliva concentration of 10%, and then mixing with cortisol.

As can be understood from FIG. 32A, it might be confirmed that the biohormone detection sensor according to above Example 4 may sense cortisol even at a concentration of 0.1 nm present in saliva.

Referring to FIG. 32B, the biohormone detection sensor according to Example 4 was reacted with a reaction solution having a cortisol concentration of 100 nM, 10 nM, 1 nM, 0.1 nM, and 0 nM, after which Relative $\Delta\lambda_{max}$ (%) was measured and shown. The reaction solution was prepared by mixing a solution having human serum albumin (HSA) dispersed in PBS with cortisol.

As can be understood from FIG. 32B, it might be confirmed that the biohormone detection sensor according to above Example 4 may sense cortisol even at a concentration of 0.1 nm present in blood.

In other words, as can be understood from specific experimental embodiments and the results of evaluating properties with regard to the fibrinogen detection sensor and the method for fabricating the same according to the third embodiment, it may be confirmed for the biohormone detection sensor according to the above embodiment that controlling a size of the gold nanoparticle deposited on the cover glass to be 80 nm is a method for enhancing cortisol sensing efficiency. In addition, it can be understood that the biohormone detection sensor fabricated through the gold nanoparticle having a size of 80 nm or more may selectively react with cortisol and also sensitively sense even at a concentration of 0.1 nM.

Although the invention has been described in detail with reference to exemplary embodiments, the scope of the present invention is not limited to a specific embodiment and should be interpreted by the attached claims. In addition, those skilled in the art should understand that many modifications and variations are possible without departing from the scope of the present invention.

The invention claimed is:

1. A biomaterial detection sensor comprising:
a substrate; and
a detection probe including a metal nanoparticle deposited on the substrate, and an erythrocyte membrane conformally covering the metal nanoparticle,
wherein the detection probe sensitively reacts with fibrinogen,
wherein the biomaterial detection sensor is configured to linearly sense the fibrinogen in a concentration range of 0.001 to 10 mg/mL, and
wherein an amount of change in a surface plasmon resonance signal of the substrate that changes when the detection probe selectively reacts with the fibrinogen decreases linearly as the concentration of the fibrinogen decreases.

2. The biomaterial detection sensor of claim 1, wherein a plurality of detection probes are disposed on the substrate, in which, among the plurality of detection probes, a distance between first and second metal nanoparticles adjacent to each other before reacting with the fibrinogen is same as a distance between the first and second metal nanoparticles after reacting with the fibrinogen.

3. The biomaterial detection sensor of claim 1, wherein the erythrocyte membrane conformally covers both the substrate and the metal nanoparticle.

4. The biomaterial detection sensor of claim 3, wherein one region of the erythrocyte membrane is disposed to be spaced apart from the substrate by a predetermined distance with the metal nanoparticle interposed therebetween, and an other region of the erythrocyte membrane is disposed to come into direct contact with the substrate.

5. The biomaterial detection sensor of claim 1, wherein a thickness of the erythrocyte membrane is 2 nm or less.

6. A method for fabricating a biomaterial detection sensor, comprising:
preparing a substrate and a metal nanoparticle;
depositing the metal nanoparticle on the substrate;
extracting an erythrocyte membrane from an erythrocyte; and
providing the erythrocyte membrane on the substrate where the metal nanoparticle is deposited, so as to form a detection probe including the metal nanoparticle on the substrate and the erythrocyte membrane conformally covering the metal nanoparticle,
wherein the detection probe sensitively reacts with fibrinogen,
wherein the biomaterial detection sensor is configured to linearly sense the fibrinogen in a concentration range of 0.001 to 10 mg/mL, and
wherein an amount of change in a surface plasmon resonance signal of the substrate that changes when the detection probe selectively reacts with the fibrinogen decreases linearly as the concentration of the fibrinogen decreases.

7. The method of claim 6, wherein a concentration of the erythrocyte membrane provided on the substrate where the metal nanoparticle is deposited is 0.05 v/v % or less.

\* \* \* \* \*